United States Patent [19]
Davis et al.

[11] Patent Number: 5,958,935
[45] Date of Patent: Sep. 28, 1999

[54] SUBSTITUTED 2-ANILINOPYRIMIDINES USEFUL AS PROTEIN KINASE INHIBITORS

[75] Inventors: Peter David Davis, Aston Rowant; David Festus Charles Moffat, Maidenhead; Jeremy Martin Davis; Martin Clive Hutchings, both of Wokingham, all of United Kingdom

[73] Assignee: Celltech Therapeutics Limited, Berkshire, United Kingdom

[21] Appl. No.: 08/753,041

[22] Filed: Nov. 19, 1996

[30] Foreign Application Priority Data

Nov. 20, 1995 [GB] United Kingdom ............... 9523675

[51] Int. Cl.$^6$ ............... A61K 31/505; C07D 239/28
[52] U.S. Cl. ............... 514/275; 544/323; 544/325; 544/332
[58] Field of Search ............... 544/332, 323, 544/325; 514/275

[56] References Cited

U.S. PATENT DOCUMENTS

| | | | |
|---|---|---|---|
| 4,012,495 | 3/1977 | Schmiechen et al. | 424/274 |
| 4,015,017 | 3/1977 | Gazave | 424/331 |
| 4,153,713 | 5/1979 | Hutch et al. | 424/274 |

(List continued on next page.)

FOREIGN PATENT DOCUMENTS

| | | |
|---|---|---|
| 0 233 461 A2 | 8/1987 | European Pat. Off. . |
| 0 295 210 A1 | 12/1988 | European Pat. Off. . |
| 0 337 943 A2 | 10/1989 | European Pat. Off. . |
| 0 393 500 A1 | 10/1990 | European Pat. Off. . |
| 0 490 823 A1 | 6/1991 | European Pat. Off. . |
| 0 470 805 A1 | 2/1992 | European Pat. Off. . |
| 0 497 564 A1 | 8/1992 | European Pat. Off. . |
| 0 511 865 A1 | 11/1992 | European Pat. Off. . |
| 0 537 742 A2 | 4/1993 | European Pat. Off. . |
| 0 564 409 A1 | 10/1993 | European Pat. Off. . |
| 2 545 356 A1 | 11/1984 | France . |
| 250 1443 | 7/1975 | Germany . |
| 3-77872 | 4/1991 | Japan . |
| 3-77923 | 4/1991 | Japan . |
| 1588639 | 4/1981 | United Kingdom . |
| WO 87/06576 | 11/1987 | WIPO . |
| WO 91/15451 | 10/1991 | WIPO . |
| WO 91/16892 | 11/1991 | WIPO . |
| WO 92/00968 | 1/1992 | WIPO . |
| WO 92/06085 | 4/1992 | WIPO . |
| WO 92/06963 | 4/1992 | WIPO . |
| WO 92/07567 | 5/1992 | WIPO . |
| WO 92/12961 | 8/1992 | WIPO . |
| WO 92/19594 | 11/1992 | WIPO . |
| WO 92/19602 | 11/1992 | WIPO . |
| WO 93/10118 | 5/1993 | WIPO . |
| WO 93/19748 | 10/1993 | WIPO . |
| WO 94/02465 | 2/1994 | WIPO . |
| WO 94/10118 | 5/1994 | WIPO . |
| WO 94/12461 | 6/1994 | WIPO . |
| WO 94/13661 | 6/1994 | WIPO . |
| WO 94/14742 | 7/1994 | WIPO . |
| WO 94/20446 | 9/1994 | WIPO . |
| WO 94/20455 | 9/1994 | WIPO . |
| WO 95/04046 | 2/1995 | WIPO . |
| WO 95/09847 | 4/1995 | WIPO . |
| WO 95/09851 | 4/1995 | WIPO . |
| WO 95/09852 | 4/1995 | WIPO . |
| WO 95/09853 | 4/1995 | WIPO . |
| WO 95/17386 | 6/1995 | WIPO . |
| WO 95/31451 | 11/1995 | WIPO . |
| WO 95/33727 | 12/1995 | WIPO . |
| WO 95/35281 | 12/1995 | WIPO . |
| WO 95/35283 | 12/1995 | WIPO . |
| WO 96/14843 | 5/1996 | WIPO . |
| WO 97/09297 | 3/1997 | WIPO . |

OTHER PUBLICATIONS

Ashton, "Selective Type IV Phosphodiesterase Inhibitors as Antiasthmatic Agents. The Syntheses and Biological Activities of 3–(Cyclopentyloxy)–4–methyoxybenzamides and Analogues", *J. Med. Chem.*, 1994, 37, 1696–1703.

Beavo & Reifsnyder, "Primary Sequence of Cyclic Nucleotide Phosphodiesterase Isozymes and the Design of Selective Inhibitors" *TIPS*, 1990, 11, 150–155.

(List continued on next page.)

*Primary Examiner*—Richard L. Raymond
*Attorney, Agent, or Firm*—Woodcock Washburn Kurtz Mackiewicz & Norris LLP

[57] ABSTRACT

2-Anilinopyrimidines, processes for their preparation, pharmaceutical compositions containing them, their use in medicine. In a preferred embodiment, the compounds have the general formula (1):

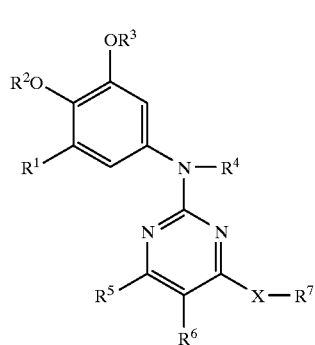

(1)

wherein $R^1$ is preferably methoxy; $R^2$ and $R^3$ are preferably methyl; $R^4$ is preferably a hydrogen atom; $R^5$ is a hydrogen atom or an optionally substituted straight or branched chain alkyl, alkenyl or alkynyl group; $R^6$ is a hydrogen or halogen atom or an amino (—$NH_2$), substituted amino, nitro, carboxyl (—$CO_2H$), esterified carboxyl or —$X^1R^{6a}$ where $X^1$ is a direct bond or a linker atom or group and $R^{6a}$ is an optionally substituted straight or branched chain alkyl, alkenyl or alkynyl group; X is a direct bond or a linker atom or group; and $R^7$ is an optionally substituted aliphatic, cycloaliphatic, heteroaliphatic, heterocycloaliphatic, aromatic or heteroaromatic group. Compounds of the invention are selective protein kinase inhibitors, particularly the kinases p56$^{lck}$, p59$^{fyn}$, ZAP-70 and protein kinase C and are of use in the prophylaxis and treatment of immune diseases, hyperproliferative disorders and other diseases in which inappropriate protein kinase action is believed to have a role.

23 Claims, No Drawings

U.S. PATENT DOCUMENTS

| | | | |
|---|---|---|---|
| 4,193,926 | 3/1980 | Schmiechen et al. | 260/326.5 |
| 4,303,649 | 12/1981 | Jones | 424/177 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,521,184 | 5/1996 | Zimmermann | 514/252 |
| 5,550,137 | 8/1996 | Beeley et al. | 514/354 |
| 5,580,888 | 12/1996 | Warrellow et al. | 514/332 |
| 5,593,997 | 1/1997 | Dow et al. | 514/258 |
| 5,608,070 | 3/1997 | Alexander et al. | 546/270 |
| 5,622,977 | 4/1997 | Warrellow | 514/336 |
| 5,693,659 | 12/1997 | Head et al. | 514/357 |
| 5,723,460 | 3/1998 | Warrellow et al. | 514/247 |
| 5,728,708 | 3/1998 | Zimmermann | 514/252 |
| 5,739,144 | 4/1998 | Warrellow et al. | 514/277 |
| 5,753,663 | 5/1998 | Flippin et al. | 514/257 |

OTHER PUBLICATIONS

Buu–Hoi, N.P. et al., "Bromination of Some 1,2,2–Triarylethylenes" *J. of Organic Chemistry*, 1958, 1261–1263.

Buu–Hoi et al., "New Method for the Synthesis of ω,ω–Diarylacetophenones Aminated in the Aromatic Nucleus. Plynitration of Triarylethylenes", *Chem. Abstr.*, 1964, 61(13), 16006h.

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Chemical Abstracts. Registry Handbook—Number Section. Printed Issues Columbus US *compounds with registry numbers 95992–21–5; 95971–60–1; 90053–37–5; 82668–18–6; 80395–25–1; 49610–49–3, 1972.

Daves, G.D. et al., "Pyrimidines. XIII. 2– and 6–Substituted 4–Pyrimidinecarboxylic Acids", *J. Of Hev. Chem.*, 1964, 1, 130–133.

Dietl, F. et al., "Chinone von Benzo–und Dibenzokronenethern", *Synthesis*, 1985, 626–631.

El–Wakil et al., "Study of the proton magnetic resonance of methoxytamoxifen towards ortho–substitiution", *Chem. Abstr.*, 1992, 116, 255248t.

Geissler, J.F. et al., "Thiazolidine–Diones. Biochemical and Biological Activity of a Novel Class of Tyrosine Protein Kinase Inhibitors", *J. Of Biol. Chem.*, 1990, 265(36), 22255–22261.

Hanks, S.K. et al., "The eukaryotic protein kinase superfamily: kinase (catalytic) domain structure and classification", *FASEB J.*, 1995, 9, 576–596.

Hirose et al., "Styrene Derivatives and Electrophotpgraphic Photoreceptor Containing Them", *Chem. Abstr.*, 1993, 118, 136183z.

Ishikura, M. et al., "An Efficient Synthesis of 3–Heteroarylpyridines via Diethyl–(3–pyridyl)–borane" *Synthesis*, 1984, 936–938.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4(2), 123–132.

Lisle, H. et al., "IL–2–Induced Eosinophilia in the Rat Pleural Cavity: The Effect of Dexamethasone and Indomethacin", *Br. J. Pharmacol.* 1993, 108, 230.

Livi et al., "Cloning and Expression of cDNA for a Human Low–$K_m$3 Rolipram–sensitive Cyclic AMP Phosphodiesterase", *Molecular and Cellular Biol.* 1990, 10(6), 2678–2686.

Manhas et al., "heterocyclic Compounds XII. Quinazoline Derivatives as Potential Antifertility Agents (1)" *J. Heterocyclic Chem.*, 1979, 16, 711–715.

Meyers, A.J. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39(18), 2787–2793.

Mezheritskaya, "Synthesis and properties of carboxonium het=erocyclic systems. VII. Synthesis and properties of 2–benzyl–substituted 1,3–dioxolanium salts", *Chem. Abstr.*, 1980, 93, 95160j, 635.

Mitsunobu, O., "The Use of Diethyl Azodicarboxylate and Triphenylphosphine in Synthesis and Transformation of Natural Products" *Synthesis*, 1981, 1–28.

Newton, A.C., "Protein Kinase C: Structure, Function, Regulation", *J. Biol. Chem.*, 1995, 270(48), 28495–28498.

Nicholson et al., "Differential Modulation of Tissue Function and Therapeutic Potential of Selective Inhibitors of Cyclic Nucleotide Phosphodiesterase Isoenzymes" *TIPS*, 1991, 12, 19–27.

O'Connor et al., "Voltammetry and Controlled Potential Oxidation of 3,4–dimethoxypropenylbenzene at a rotating platinum electrode in unbuffered acetonitrile and in acetonitrile–pyridine solution" *Chem. Abstr.*, 1964, 60(8) #10203.4.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarboline", *J. Heterocyclic Chem.*, 1994, 31, 1311–1315.

Porter et al., "Preparation of 6–phenyl–3–(5–tetrazolyl) pyridin–=2(H)–one Derivatives as Cyclic AMP–dependent Protein Kinase Agonists" *Chem. Abstr.*, 1992, 117(9), 90296n.

Ramalingam, Deshmukh and Sattur, "Synthesis and Pharmacology of 2,5–Disubstituted 1,3,4–Zxadiazoles" *J. Indian Chem. Soc.*, 1981, 58(3), 269–271.

Reddy et al., "Inhibition of Breast Cancer Cell Growth in Vitro by a Tyrosine Kinase Inhibitor" *Cancer Research*, 1992, 52, 3636–3641.

Sánchez, H.I. et al., "Formal Total Syntehsis of β–Pipitzol", *Tetrahedron*, 1985, 41(12), 2355–2359.

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls", *Tetrahedron Lett.*, 1987, 28(43), 5093–5096.

Thompson, W.J. and Gaudino, J., "A General Synthesis of 5–Arylnicotinates" *J. Org. Chem.*, 1984, 49, 5237–5243.

Yeadon et al., "Mechanisms Contributing to Ozone–Induced Bronchial Hyperreactivity in Guinea Pigs", *Pulmonary Pharm.*, 1992, 5, 39–50.

Yoneda et al., "The Antiproliferative Effects of Tyrosine Kinase Inhibitors Tyrphostins on a Human Squamous Cell Carcinoma in Vitro and in Nude Mice" *Cancer Research*, 1991, 51, 4430–4435.

Sakakibara, K. et al., "Preparation of N–pyridyl–4–(benzyloxy)benzamides as Cardiotonics", *Chem. Abstr.*, 1988, 108, No. 131583p.

Tsutsumi, K. et al., "Preparation of (Dialkoxyphosphinoylmethyl)benzamides as Antihyperlipidemics", *Chem. Abstr.*, 1990, 113, No. 6599a.

Chemical Abstracts, Registry No. 2732–15–2, prior to 1967, 1 page.

Chemical Abstracts, Registry No. 4593–13–9, prior to 1967, 1 page.

Bortolus et al., "cis–trans Isomerization of azastilbenes photosensitized by biacetyl", *Mol. Photochem.*, 1970, 2(4), 311–321, CAPLUS accession No. 1971–434722, 2 pages.

Kaiser et al., "Selective metalations of methylated pyridines and quinolines", *J. Org. Chem.*, 1973, 38(1), 71–75, CAPLUS accession No. 1973–71853, 2 pages.

Pickett, W.C. et al., "Modulation of Eicosanoid Biosynthesis by Novel Pyridinylpyrimidines", *Ann. N.Y. Acad. Sci.*, 1994, 744, 299–305.

Spada, A.P. et al., "Small Molecule Inhibitors of Tyrosine Kinase Activity", *Exp. Opin. Ther. Patents*, 1995, 5(8), 805–817.

Yamaguchi, H., "Guanidinobenzene derivatives as anticoagulants", *Chem. Absts.*, 1989, 110, 655 (Abstract No. 94706z).

Zimmermann, J. et al., "Phenylamino–Pyrimidine (PAP) Derivatives: A New Class of Potent and Selective Inhibitors of Protein Kinase C (PKC)", *Arch. Pharm.*, 1996, 329(7), 371–376.

Zimmermann, J. et al, "Phenylamino–Pyrimidine (PAP)—Derivatives: A New Class of Potent and Highly Selective PDGF–Receptor Autophosphorylation Inhibitors", *Bioorg. Med. Chem. Lett.*, 1996, 6(11), 1221–1226.

Zimmermann, J. et al., "Potent and Selective Inhibitors of the ABL–Kinase Phenylamino–Pyrimidine (PAP) Derivatives", *Bioorg. Med. Chem. Lett.*, 1997, 7(2), 187–192.

Kefalas, P. et al., "Signalling by the $p60^{c-src}$ Family of Protein–Tyrosine Kinases", *Int. J. Biochem. Cell Biol.*, 1995, 27(6), 551–563.

Chatterjee, A. et al., "Total Synthesis of Ring–C Aromatic 18–Nor Steroid", *Tetrahedron*, 1980, 36, 2513–2519.

Clayton, S.E. et al., "Direct Aromatic tert–Butylation during the Synthesis of Thiochroman–4–ones", *Tetrahedron*, 1993, 49(4), 939–946.

Collins, R.F. et al., "The Chemotherapy of Schistosomiasis. Part IV. Some Ethers of 4–Amino–2–methoxyphenol", *J. Chem. Soc.*, 1961, 1863–1879.

Degani, I. et al., "Cationi etero–aromatici Nota VI—Sintesi di alcuni derivati del perclorato di tiacromilio", *Boll. Sci. Fac. Chim. Ind. Bologna*, 1966, 24(2–3), 75–91 (English Summary Only).

Geissler et al., "Biochemical and Biological Activity of a Novel Class of Tyrosine Protein Kinase Inhibitors", *J. Biol. Chem.*, 1990, 265(36), 22255–22261.

Griffin, R.W. et al., "1–Methyl–7–halo–2–naphthalenecarboxylic Acid Derivatives", *J. Organic Chem.*, 1964, 29(8), 2109–2116.

Gupta, A.S. et al., "Friedel–Crafts Condensation of Ethyl Allylmalonate with Anisole", *Tetrahedron*, 1967, 23, 2481–2490.

Hart et al., "Alkylation of Phenol with a Homoallylic Halide", *J. Am. Chem. Soc.*, 1963, 85, 3269–3273.

Johnson et al., "Identification of Retinoic Acid Receptor β Subtype Specific Agonists", *J. Med. Chem.*, 1996, 39(26), 5027–5030.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis*, 1987, 1064–1067 (English abstract only).

Meyers, A.I. et al., "The Synthesis of 2–Pyridones from Cyclic Cyano Ketones. A New Aromatization Procedure for Dihydro–2–pyridones", *J. Org. Chem.*, 1964, 29, 1435–1438.

Chemical Abstracts, "Hypoglycemic Pharmaceuticals Containing Manzammide Derivatives", *Chem. Abstr.*, 1983, 99(6), No. 43558Z.

Dent et al., "Inhibition of eosinophil cyclic nucleotide PDE activity and opsonised zymosan–stimulated respiratory burst by 'type IV'–selective PDE inhibitors", *Br. J. Pharmacol.*, 1991, 103, 1339–1346.

Grammaticakis, "Contribution A L'Etude de L'Absortion Dans L'Ultraviolet Moyen Et Le Visible Des N–Aroyl–Arylamines. IV. 2,3–, 3,4– et 2,4–, dimethoxybenzoylarylamines", *Bulletin DeLa Societa Chemique De France*, 1965, 848–858.

Green and Wuts, "Protective Groups in Organic Synthesis", John Wiley & Sons, New York, 1991.

Heaslip et al., "Phosphodiesterase–IV Inhibition, Respiratory Muscle Relaxation and Bronchodilation by WAY–PDA–641", *J. Pharm. Exper. Ther.*, 1993, 268(2), 888–896.

Karlsson et al., "T–Lymphocyte and Inflammatory Cell Research in Asthma", Joller, G. et al. (eds.), Academic Press, 1993, 323–347.

Mathison et al., "Synthesis and Hypotensive Properties of Tetrahydroixoquinolines", *J. Med. Chem.*, 1973, 16(4), 332–336.

Miyaura, N. et al., "The Palladium–Catalyzed Cross–Coupling Reaction of Phenylboronic Acid with Haloarenes in the Presence of Bases", *Synth. Comm.*, 1981, 11, 513–519.

Shioiri et al., "New Methods and Reagents in Organic Synthesis. 3. Diethyl Phosphorocyanidate: A New Reagent for C–Acylation", *J. Org. Chem.*, 1978, 43, 3631–3632.

Takeuchi, I. et al., "On the Antimocrobial Activity and Syntheses of Carbanilide and Salicylanilide Derivatives", *Chem. Abstr.*, 1983, 98, No. 12557y.

Tominaga et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo[3,4-d]pyrimidines, and 5-Aza [2.2.3]cyclazines", *J. Het. Chem.*, 1990, 27, 647–660.

Trost and Fleming (eds.), *Comprehensive Organic Synthesis*, Pergamon Press, New York, 1991, 3, 531–541.

Vidal et al., "Electrophilic Amination: Preparation and Use of N–Boc–3–(4–cyanophenyl)oxaziridine, a New Reagent That Transfers a N–Boc Group to N– and C–Nucleophiles", *J. Org. Chem.*, 1993, 58, 4791–4793.

SUBSTITUTED 2-ANILINOPYRIMIDINES USEFUL AS PROTEIN KINASE INHIBITORS

This invention relates to substituted 2-anilinopyrimidines, to processes for their preparation, to pharmaceutical compositions containing them, and to their use in medicine.

Protein kinases participate in the signalling events which control the activation, growth and differentiation of cells in response to extracellular mediators and to changes in the environment. In general, these kinases fall into two groups; those which preferentially phosphorylate serine and/or threonine residues and those which preferentially phosphorylate tyrosine residues [Hanks, S K, Hunter T, FASEB. J. 9, 576–596 (1995)]. The serine/threonine kinases include for example, protein kinase C isoforms [Newton A C, J. Biol. Chem. 270, 28495–28498 (1995)] and a group of cyclin-dependent kinases such as cdc2 [Pines J, Trends in Biochemical Sciences 18, 195–197 (1995)]. The tyrosine kinases include membrane-spanning growth factor receptors such as the epidermal growth factor receptor [Iwashita S and Kobayashi M. Cellular Signalling 4, 123–132 (1992)], and cytosolic non-receptor kinases such as $p56^{lck}$ $p59^{fyn}$ ZAP-70 and csk kinases [Chan C et al Ann. Rev. Immunol. 12, 555–592 (1994)].

Inappropriately high protein kinase activity has been implicated in many diseases resulting from abnormal cellular function. This might arise either directly or indirectly, for example by failure of the proper control mechanisms for the kinase, related for example to mutation, over expression or inappropriate activation of the enzyme; or by over- or under production of cytokines or growth factors also participating in the transduction of signal upstream or downstream of the kinase. In all of these instances, selective inhibition of the action of the kinase might be expected to have a beneficial effect.

We have now found a series of substituted 2-anilinopyrimidines which are potent and selective inhibitors of protein kinases, especially the kinases $p56^{lck}$, $p59^{fyn}$, ZAP-70 and protein kinase C. The compounds are thus of use in the prophylaxis and treatment of immune diseases, hyper-proliferative disorders and other diseases in which inappropriate protein kinase action is believed to have a role.

Thus, according to one aspect of the invention, we provide a compound of formula (1):

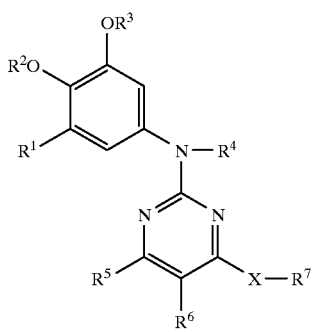

(1)

wherein $R^1$ is a hydrogen or halogen atom or an optionally substituted straight or branched chain alkyl, alkenyl or alkynyl group or a group selected from hydroxyl (—OH), substituted hydroxyl, thiol (—SH), substituted thiol, amino (—NH$_2$), or substituted amino;

$R^2$ and $R^3$, which may be the same or different, is each an optionally substituted straight or branched chain alkyl, alkenyl or alkynyl group;

$R^4$ is a hydrogen atom or a straight or branched chain alkyl group;

$R^5$ is a hydrogen atom or an optionally substituted straight or branched chain alkyl, alkenyl or alkynyl group;

$R^6$ is a hydrogen or halogen atom or an amino (—NH$_2$), substituted amino, nitro, carboxyl (—CO$_2$H) or esterified carboxyl group or a group —X$^1$—R$^{6a}$ where X$^1$ is a direct bond or a linker atom or group and $R^{6a}$ is an optionally substituted straight or branched chain alkyl, alkenyl or alkynyl group;

X is a direct bond or a linker atom or group;

$R^7$ is an optionally substituted aliphatic, cycloaliphatic, heteroaliphatic, heterocycloaliphatic, aromatic or heteroaromatic group;

and the salts, solvates, hydrates and N-oxides thereof.

Halogen atoms represented by the group $R^1$ and/or $R^6$ in compounds of formula (1) include for example fluorine, chlorine, bromine or iodine atoms.

When $R^1$, $R^2$, $R^3$, $R^5$ and/or $R^{6a}$ is an optionally substituted straight or branched chain alkyl, alkenyl or alkynyl group each of said groups may independently be an optionally substituted straight or branched chain $C_{1-6}$ alkyl, e.g. $C_{1-3}$ alkyl, $C_{2-6}$ alkenyl, e.g. $C_{2-4}$ alkenyl, or $C_{2-6}$ alkynyl, e.g. $C_{2-4}$ alkynyl group. Particular examples of such groups include optionally substituted —CH$_3$, —CH$_2$CH$_3$, —(CH$_2$)$_2$CH$_3$, —CH(CH$_3$)$_2$, —(CH$_2$)$_3$CH$_3$, —CH(CH$_3$)CH$_2$CH$_3$, —CH$_2$CH(CH$_3$)$_2$, —C(CH$_3$)$_3$, —(CH$_2$)$_4$CH$_3$, —(CH$_2$)—CHCH$_2$, —CHCHCH$_3$, —CH$_2$CHCH$_2$, —CHCHCH$_2$CH$_3$, —CH$_2$CHCHCH$_3$, —(CH$_2$)$_2$CHCH$_2$, —CCH, —CCCH$_3$, —CH$_2$CCH, —CCCH$_2$CH$_3$, —CH$_2$CCCH$_3$, or —(CH$_2$)$_2$CCH groups. The optional substituents which may be present on these groups include one, two, three or more substituents selected from halogen atoms, e.g. fluorine, chlorine, bromine or iodine atoms, or hydroxyl, $C_{1-6}$ alkoxy, e.g. methoxy or ethoxy, thiol, $C_{1-6}$ alkylthio e.g. methylthio or ethylthio, amino, $C_{1-6}$ alkylamino, e.g. methylamino or ethylamino, or $C_{1-6}$ dialkylamino, e.g. dimethylamino or diethylamino groups.

Substituted hydroxyl groups represented by the group $R^1$ in compounds of formula (1) include —OR$^8$ groups where $R^8$ is an optionally substituted straight or branched $C_{1-6}$ alkyl, e.g. methyl or ethyl, $C_{2-6}$ alkenyl, e.g. allyl, or $C_{2-6}$ alkynyl, e.g. ethynyl group. The optional substituents which may be present on these groups include a phenyl group and/or one, two, three or more of the atoms or groups described above in relation to substituents present on alkyl groups represented by $R^1$.

Substituted thiol groups represented by the group $R^1$ include —SR$^8$ groups, wherein $R^8$ is as just defined.

When $R^1$ and/or $R^6$ is a substituted amino group it may be for example a —NHR$^9$ or —NR$^9$R$^{10}$ group where $R^9$ and $R^{10}$, which may be the same or different, is each a group —R$^8$ or —COR$^8$ where $R^8$ is as just defined.

Esterified carboxyl groups represented by the group $R^6$ include groups of formula —CO$_2$Alk$^1$ wherein —CO$_2$Alk$^1$ is as defined hereinafter in connection with esterified carboxyl groups represented by the group $R^{13}$.

Linker atoms represented by X or X$^1$ in compounds of formula (1) include —O— or —S— atoms. When X or X$^1$ is a linker group it may be for example a —C(O)—, —C(S)—, —S(O)—, —S(O)$_2$—, —N(R$^{11}$)— [where R$^{11}$ is a hydrogen atom or a $C_{1-6}$ alkyl, e.g. methyl or ethyl, group], —CON(R$^{11}$)—, —OC(O)N(R$^{11}$)—, —CSN(R$^{11}$)—, —N(R$^{11}$)CO—, —N(R$^{11}$)C(O)O—, —N(R$^{11}$)CS—, —SON(R$^{11}$), —SO$_2$N(R$^{11}$), —N(R$^{11}$)SO$_2$—, —N(R$^{11}$)CON(R$^{11}$)—, —N(R$^{11}$)CSN(R$^{11}$)—, —N(R$^{11}$)SON(R$^{11}$)— or —N(R$^{11}$)SO$_2$N(R$^{11}$) group.

When $R^7$ in compounds of formula (1) is an optionally substituted aliphatic or cycloaliphatic group it may be an optionally substituted $C_{1-10}$ aliphatic or $C_{3-10}$ cycloaliphatic group. Particular examples include optionally substituted straight or branched chain $C_{1-6}$ alkyl, $C_{2-6}$ alkenyl, or $C_{2-6}$ alkynyl groups or optionally substituted $C_{3-10}$ocycloalkyl, $C_{3-10}$cycloalkenyl or $C_{3-10}$cycloalkynyl groups.

Heteroaliphatic or heterocycloaliphatic groups represented by $R^7$ include the aliphatic or cycloaliphatic groups just described but with each group additionally containing one, two, three or four heteroatoms or heteroatom-containing groups. Particular heteroatoms or groups include atoms or groups —$X^2$— where $X^2$ is as defined above for X when X is a linker atom or group.

Aromatic groups represented by $R^7$ in compounds of formula (1) include for example optionally substituted monocyclic or bicyclic fused ring $C_{6-12}$ aromatic groups, such as optionally substituted phenyl, 1- or 2-naphthyl, 1- or 2-tetrahydronaphthyl, indanyl or indenyl groups.

Heteroaromatic groups represented by $R^7$ include optionally substituted $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms.

In general, when $R^7$ is a heteroaliphatic, heterocycloaliphatic or heteroaromatic group it is attached to the remainder of the molecule of formula (1) through any available heteroatom or group or, preferably, carbon atom.

Particular examples of $R^7$ aliphatic groups include those alkyl, alkenyl or alkynyl groups specifically described above in relation to the groups $R^1$, $R^2$, $R^3$, $R^5$ and $R^6$. Each of these groups may be optionally substituted, and/or optionally interrupted by one or two heteroatoms or heteroatom-containing groups represented by —$X^2$— [where $X^2$ is as previously defined], to yield particular examples of $R^7$ optionally substituted aliphatic or heteroaliphatic groups.

Particular examples of $R^7$ cycloaliphatic and heterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, 2,4-cyclopentadiene-1-yl, 3,5,-cyclohexadiene-1-yl, pyrrolidine, e.g. 2- or 3-pyrrolinyl, pyrrolidinyl, dioxolanyl, e.g. 1 ,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, 1,4-dioxanyl, morpholinyl, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,2-oxadiazinyl groups.

Examples of heteroaromatic groups represented by $R^7$ include optionally substituted pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on any of the above $R^7$ groups in compounds of formula (1) include one, two, three or more substituents, each represented by the group $R^{12}$. The substituent $R^{12}$ may be selected from an atom or group $R^{13}$ or -Alk$(R^{13})_m$, where $R^{13}$ is a halogen atom, or an amino (—$NH_2$), —$NHR^{14}$ [where $R^{14}$ is an -Alk$(R^{13})_m$, heterocycloalkyl, -Alk-heterocycloalkyl, aryl or heteroaryl group], —$N(R^{14})_2$ [where each $R^{14}$ group is the same or different], nitro, cyano, hydroxyl (—OH), —$OR^{14}$, formyl, carboxyl (—$CO_2H$), esterified carboxyl, thiol (—SH), —$SR^{14}$, —$COR^{14}$, —$CSR^{14}$, —$SO_3H$, —$SO_2R^{14}$, —$SO_2NH_2$, —$SO_2NHR^{14}$, $SO_2N[R^{14}]_2$, —$CONH_2$, —$CSNH_2$, —$CONHR^{14}$, —$CSNHR^{14}$, —$CON[R^{14}]_2$, —$CSN[R^{14}]_2$, —$NHSO_2H$, —$NHSO_2R^{14}$, —$N[SO_2R^{14}]_2$, —$NHSO_2NH_2$, —$NHSO_2NHR^{14}$, —$NHSO_2N[R^{14}]_2$, —$NHCOR^{14}$, —$NHCONH_2$, —$NHCONHR^{14}$, —$NHCON[R^{14}]_2$, —$NHCSR^{14}$, —$NHCSNH_2$, —$NHCSNHR^{14}$, —$NHCSN[R^{14}]_2$, —$NHC(O)OR^{14}$, or an optionally substituted cycloalkyl aryl or heteroaryl group; or $R^{12}$ may be an optionally substituted heterocycloalkyl or -Alk-heterocycloalkyl group provided that when $R^{12}$ is a heterocycloalkyl group X in compounds of the invention is either a linker atom or group, or X is a bond and $R^7$ is an optionally substituted aliphatic, cycloaliphatic, heteroaliphatic, heterocycloaliphatic, aromatic or heteroaromatic group other than a pyridyl group; Alk is a straight or branched $C_{1-6}$ alkylene, $C_{2-6}$ alkenylene or $C_{2-6}$ alkynylene chain, optionally interrupted by one, two or three —O— or —S— atoms or S—(O)—, —$S(O)_2$— or —$N(R^{11})$— groups; and m is zero or an integer 1, 2 or 3.

When in the group -Alk$(R^{13})_m$ m is an integer 1, 2 or 3, it is to be understood that the substituent or substituents $R^{13}$ may be present on any suitable carbon atom in -Alk. Where more than one $R^{13}$ substituent is present these may be the same or different and may be present on the same or different atom in -Alk or in $R^7$ as appropriate. Thus for example, $R^7$ may represent a —$CH(R^{13})_2$ group, such as a —CH(OH)Ar group where Ar is an aryl or heteroaryl group as defined below. Clearly, when m is zero and no substituent $R^{13}$ is present the alkylene, alkenylene or alkynylene chain represented by Alk becomes an alkyl, alkenyl or alkynyl group.

When $R^{13}$ is a halogen atom it may be for example a fluorine, chlorine, bromine, or iodine atom.

Esterified carboxyl groups represented by the group $R^{13}$ include groups of formula —$CO_2Alk^1$ wherein $Alk^1$ is a straight or branched, optionally substituted $C_{1-8}$ alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^1$ group include $R^{13}$ substituents described above.

When Alk is present in or as a substituent $R^{12}$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N($R^{11}$)— groups.

Optionally substituted cycloalkyl groups represented by the group $R^{13}$ include optionally substituted $C_{5-7}$ cycloalkyl groups such as optionally substituted cyclopentyl or cyclohexyl groups.

Heterocycloalkyl groups represented by the group $R^{12}$ or $R^{14}$ include optionally substituted heteroC$_{3-6}$cycloalkyl groups containing one or two oxygen, sulphur or nitrogen atoms. Particular examples of such groups include optionally substituted azetidinyl pyrrolidinyl, piperidinyl, piperazinyl, homopiperazinyl, morpholinyl or thiomorpholinyl groups. The heterocycloalkyl group may be attached to the remainder of the molecule through any of its ring carbon atoms, or where present, ring nitrogen atom. Where the group $R^{12}$ is an -Alk-heterocycloalkyl group, Alk may be as defined above and the heterocycloalkyl portion may be as just defined, attached to Alk through any of its ring carbon atoms, or where present, ring nitrogen atom.

Optional subsituents which may be present on $R^{12}$, $R^{13}$ or $R^{14}$ cycloalkyl or heterocycloalkyl groups include one or two $C_{1-6}$ alkyl, e.g. methyl or ethyl, hydroxyl (—OH), hydroxyC$_{1-6}$alkyl, e.g. hydroxymethyl or hydroxyethyl, or $C_{1-6}$ alkoxy, e.g. methoxy or ethoxy groups. The substituent (s) may be present on any available ring carbon or nitrogen atom as appropriate.

Aryl and heteroaryl groups represented by the groups $R^{13}$ or $R^{14}$ include for example optionally substituted monocyclic or bicyclic $C_{6-12}$ aromatic groups, or $C_{1-9}$ heteroaromatic groups such as those described above in relation to the group $R^7$.

Particularly useful atoms or groups represented by $R^{12}$ include fluorine, chlorine, bromine or iodine atoms, or $C_{1-6}$alkyl, $C_{1-6}$ alkylamino, $C_{1-6}$hydroxyalkyl, $C_{1-6}$alkylthiol, $C_{1-6}$alkoxy, hydroxyC$_{1-6}$alkoxy, aminoC$_{1-6}$alkoxy, $C_{1-6}$alkylaminoC$_{1-6}$alkoxy, $C_{1-6}$dialkylaminoC$_{1-6}$alkoxy, optionally substituted $C_{5-7}$cyclo-alkoxy, optionally substituted $C_{5-7}$cycloalkyl, optionally substituted $C_{5-7}$cycloalkylamino, haloC$_{1-6}$alkyl, haloC$_{1-6}$alkoxy, $C_{1-6}$alkylamino, amino (—NH$_2$), aminoC$_{1-6}$alkyl, $C_{1-6}$dialkylamino, hydroxyC$_{1-6}$ alkylamino, aminoC$_{1-6}$alkylamino, $C_{1-6}$alkylaminoC$_{1-6}$alkylamino, $C_{1-6}$dialkylaminoC$_{1-6}$alkylamino, $C_{1-6}$alkylaminoC$_{1-6}$dialkylamino, $C_{1-6}$dialkylaminoC$_{1-6}$dialkylamino, nitro, cyano, hydroxyl (—OH), formyl [HC(O)—], carboxyl (—CO$_2$H), —CH$_2$CO$_2$H, —OCH$_2$CO$_2$H, —CO$_2$Alk$^1$ [where Alk$^1$ is as defined above], —CH$_2$CO$_2$Alk$^1$, $C_{1-6}$alkoxycarbonylC$_{1-6}$alkoxy, $C_{1-6}$ alkanoyl, optionally substituted phenyl $C_{1-6}$alkanoyl, thiol (—SH), thioC$_{1-6}$alkyl, —SC(NH)NH$_2$, sulphonyl (—SO$_3$H), $C_{1-6}$alkylsulphonyl, optionally substituted phenylsulphonyl, aminosulphonyl (—SO$_2$NH$_2$), $C_{1-6}$alkylaminosulphonyl, $C_{1-6}$dialkylaminosulphonyl, optionally substituted phenylamino-sulphonyl, carboxamido (—CONH$_2$), $C_{1-6}$alkylaminocarbonyl, $C_{1-6}$dialkylaminocarbonyl, optionally substituted phenylaminocarbonyl, aminocarbonylmethyl, $C_{1-6}$alkylaminocarbonylmethyl, optionally substituted benzylaminocarbonylmethyl, —NHC(S)NH$_2$, sulphonylamino (—NHSO$_2$H), $C_{1-6}$alkylsulphonylamino, $C_{1-6}$dialkylsulphonylamino, optionally substituted phenylsulphonylamino, aminosulphonylamino (—NHSO$_2$NH$_2$), $C_{1-6}$alkylaminosulphonylamino, $C_{1-6}$dialkylaminosulphonylamino, optionally substituted phenylaminosulphonylamino, aminocarbonylamino, $C_{1-6}$alkylaminocarbonylamino $C_{1-6}$dialkylaminocarbonylamino, phenylaminocarbonylamino, $C_{1-6}$alkanoylamino, aminoC$_{1-6}$alkanoylamino, optionally substituted pyridylcarboxyamino, $C_{1-6}$alkanoylaminoC$_{1-6}$alkyl, $C_{1-6}$alkoxycarbonylamino, optionally substituted heteroC$_{3-6}$ cycloalkyl, piperidinyl, piperazinyl, 4-methyl-piperazinyl, homopipeprazinyl, or morpholinyl, optionally substituted heteroC$_{3-6}$cycloalkylC$_{1-6}$alkyl, piperidinylC$_{1-6}$alkyl, piperazinylC$_{1-6}$alkyl or morpholinylC$_{1-6}$alkyl, optionally substituted heteroC$_{3-6}$alkylC$_{1-6}$alkylamino, optionally substituted heteroC$_{3-6}$cycloalkylamino, tetrazolyl, optionally substituted phenylamino, optionally substituted benzylamino, optionally substituted benzyloxy, or optionally substituted pyridiylmethylamino group.

Where desired, two $R^{12}$ substituents may be linked together to form a cyclic group such as a cyclic ether, e.g. a $C_{1-6}$alkylenedioxy group such as a methylenedioxy or ethylenedioxy group.

Especially useful $R^{12}$ substituents include for example fluorine, chlorine, bromine or iodine atoms, or a methylamino, ethylamino, hydroxymethyl, hydroxyethyl, methylthiol, ethylthiol, methoxy, ethoxy, n-propoxy, 2-hydroxyethoxy, 3-hydroxypropoxy, 4-hydroxybutoxy, 2-aminoethoxy, 3-aminopropoxy, 2-(methylamino)ethoxy, 2-(dimethylamino)ethoxy, 3-(dimethylamino)propoxy, cyclopentyloxy, cyclohexyl, cyclohexylamino, 2-hydroxycyclohexylamino, trifluoromethyl, trifluoromethoxy, methylamino, ethylamino, amino (—NH)$_2$, aminomethyl, aminoethyl, dimethylamino, diethylamino, ethyl(methyl)amino, propyl(methyl)amino, 2-hydroxyethylamino, 3-hydroxypropylamino, 4-hydroxybutylamino, 2-aminoethylamino, 3-aminopropylamino, 4-aminobutylamino, 2-(methylamino)ethylamino, 2-(ethylamino)ethylamino, 2-(i-propylamino)ethylamino, 3-(i-propylamino)-propylamino, 2-(dimethylamino)ethylamino, 3-(dimethylamino)propylamino, 2-(diethylamino)ethylamino, 3-(diethylamino)propylamino, 2-(methylamino)-ethyl(methyl)amino, 3-(methylamino) propyl(methyl)amino, 2-(dimethylamino)ethyl(methyl) amino, 2-(dimethylamino)ethyl(ethyl)amino, nitro, cyano, hydroxyl (—OH), formyl [HC(O)-], carboxyl (—CO$_2$H), —CH$_2$CO$_2$H, —OCH$_2$CO$_2$H, —CO$_2$CH$_3$, —CO$_2$CH$_2$CH$_3$, —CH$_2$CO$_2$CH$_3$, —CH$_2$CO$_2$CH$_2$CH$_3$, —CH$_2$CO$_2$CH$_2$phenyl, t-butoxycarbonylmethoxy, acetyl, phenylacetyl, thio (—SH), thiomethyl, thioethyl, —SC(NH)NH$_2$, sulphonyl (—SO$_2$ H), methylsulphonyl, methylaminosulphonyl, ethylaminosulphonyl, dimethylaminosulphonyl, diethylaminosulphonyl, carboxamido (—CONH$_2$), methylaminocarbonyl, ethylaminocarbonyl, dimethylaminocarbonyl, diethylaminocarbonyl, methylaminocarbonylmethyl, —NHC(S)NH$_2$, sulphonylamino (—NHSO$_2$H), methylsulphonylamino ethylsulphonylamino, dimethylsulphonylamino, ethylsulphonylamino, sulphonylamino (—HHSO$_2$NH$_2$), methylaminosulphonylamino, ethylaminosulphonylamino, dimethylaminosulphonylamino, diethylaminosulphonylamino, methylaminocarbonylamino, ethylaminocarbonylamino, dimethylaminocarbonylamino diethylaminocarbonylamino, acetylamino, aminomethylcarbonylamino, acetylaminomethyl, methoxycarbonylamino, ethoxycarbonylamino, t-butoxycarbonylamino, pyrrolidinyl, piperidinyl, piperazinyl, 4-methylpiperazinyl, homopipeprazinyl, morpholinyl, pyrrolidinyl$C_{1-6}$alkyl, piperidinyl$C_{1-6}$alkyl, piperazinyl$C_{1-6}$alkyl, morpholinyl$C_{1-6}$alkyl, 2-pyrrolidinylethylamino, 2-(1-methylpyrrolidinyl) ethylamino, 1-ethylpyrrolidinylmethylamino, piperidinylamino, 1-benzylpiperidinylamino, 4-(methoxy) phenylamino, 4-(3-hydroxypropyl)phenylamino, benzylamino, benzyloxy, pyridiylmethylamino group.

It will be appreciated that where two or more $R^{12}$ substituents are present, these need not necessarily be the same atoms and/or groups.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

It will be appreciated that depending on the nature of the substituents $R^1$–$R^3$ and $R^5$–$R^7$ the compounds of formula (1) may exist as geometrical isomers and/or may have one or more chiral centres so that enantiomers or diasteromers may exist. It is to be understood that the invention extends to all such isomers of the compounds of formula (1), and to mixtures thereof, including racemates.

In one class of compounds of formula (1) the groups $R^1$, $R^2$, $R^3$, $R^4$, $R^5$, $R^7$ and X are as defined for formula (1), as is the group $R^6$ except it is not an amino, substituted amino, nitro, carboxyl or esterified carboxyl group.

One particular class of compounds according to the invention has the formula (1) wherein $R^2$ and $R^3$ is each an optionally substituted methyl or ethyl group. Particular examples of groups of these types include methyl, ethyl, halomethyl, e.g. —$CH_2F$, —$CH_2Cl$, —$CHF_2$, —$CHCl_2$, —$CF_3$, —$CCl_3$, or haloethyl groups. In general however, $R^2$ and $R^3$ is each preferably a methyl group. In compounds of this class and in general in compounds of formula (1) $R^1$ may in particular be an optionally substituted methoxy group. Particular examples of such $R^1$ groups include —$OCH_2F$, —$OCH_2Cl$, —$OCHF_2$, —$OCHCl_2$, —$OCF_3$, —$OCCl_3$ or, especially, methoxy groups.

In a further preferred class of compounds of formula (1) $R^4$ is preferably a hydrogen atom.

The groups $R^5$ and $R^6$ in compounds of formula (1) are each preferably a hydrogen atom.

In yet another preference, X in compounds of formula (1) is a direct bond, an oxygen or sulphur atom or a —$N(R^{11})$— group. Especially useful compounds of this type are those wherein X is a direct bond, a sulphur atom or a —$N(R^{11})$—, particularly a —NH—, group.

$R^7$ in compounds of formula (1) is preferably an optionally substituted aromatic or heteroaromatic group.

A further class of compounds according to the invention has the formula 1(a):

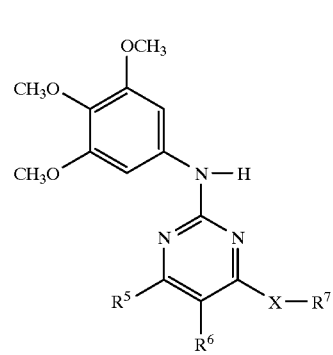

1(a)

wherein $R^5$ and $R^6$ are as defined for formula (1), X is a direct bond, an oxygen or sulphur atom, or a group —$N(R^{11})$— and $R^7$ is an optionally substituted aromatic or heteroaromatic group, and the salts, solvates, hydrates and N-oxides thereof.

In these compounds, $R^5$ is preferably a hydrogen atom. $R^6$ is preferably a group —$X^1R^{6a}$ where $X^1$ is as defined for formula (1) and $R^{6a}$ is an optionally substituted straight or branched chain alkyl group, or $R^6$ is especially a hydrogen atom.

X in compounds of formula (1a) is preferably a direct bond, a sulphur atom, or a —$N(R^{11})$— group, particularly a —NH— group.

The aromatic or heteroaromatic $R^7$ group in compounds of formulae (1) or 1 (a) in general may be as defined previously for compounds of formula (1). In one preference, however, $R^7$ is an optionally substituted phenyl, 1- or 2-naphthyl or heteroaromatic group containing one or two oxygen, sulphur and/or nitrogen atoms. Thus in particular $R^7$ may be an optionally substituted phenyl, 1- or 2-naphthyl, pyrrolyl, furyl, thienyl, indolyl, pyrazolyl, thiazolyl, [2,3-dihydro]benzofuryl, benzothiazolyl, 2-pyridyl, 3-pyridyl or 4-pyridyl group. Particularly useful groups include optionally substituted phenyl, 2-pyridyl, 3-pyridyl or 4-pyridyl groups. The aromatic or heteroaromatic group may in particular be attached to the remainder of the compound of formula (1) through any available ring carbon atom.

In general, the optional substituents which may be present on aromatic or heteroaromatic $R^7$ groups in compounds of formulae (1) or (1a) include one, two, or three $R^{12}$ substituents as generally and particularly described above and hereinafter in the Examples. Particularly useful $R^{12}$ substituents include —$NHR^{14}$, -Alk$NH_2$, -Alk$NHR^{14}$, —$OR^{14}$, -Alk$CO_2H$ or -Alk$CO_2Alk^1$ groups where $R^{14}$, Alk and $Alk^1$ are as generally and particularly defined above. Useful members of these substituents include those wherein $R^{14}$ is an -Alk, -Alk$NH_2$ or -Alk-heterocycloalkyl group. In t hese, and the other preferred substituents just mentioned, Alk and $Alk^1$ when present is each preferably a $C_{1-6}$alkyl group.

Particularly useful compounds according to the invention include: N,N'-Bis(3,4,5-Trimethoxyphenyl)-2,4-pyrimidinediamine;

4-(2-(2-Dimethylaminoethylamino)pyridin-5-yl)-N-(3,4,5-trimethoxyphenyt)-2-pyrimidineamine;

4-(2-(4-Hydroxybutylamino)pyridin-5-yl)-N-(3,4,5-trimethoxyphenyl)-2-pyrimidineamine;

4-(3-(3-Aminopropoxy)phenyl)-N-(3,4,5-trimethoxyphenyl)-2-pyrimidineamine;

N4-(3,4-Dimethoxyphenyl)-N2-(3,4,5-trimethoxyphenyl)-2,4-pyrimidinediamine;
4-(4-(2-Hydroxyethoxy)phenyl)-N-(3,4,5-trimethoxyphenyl)-2-pyrimidineamine;
4-(2-(3-(Morpholino)propylamino)pyridin-5-yl)-N-(3,4,5-trimethoxyphenyl)-2-pyrimidineamine;
4-(2-(2-(1-Methylpyrrolidin-2-yl)ethylamino)pyridin-5-yl)-N-(3,4,5-trimethoxyphenyl)-2-pyrimidineamine;
N4-(4-(Ethoxycarbonylmethyl)phenyl)-N2-(3,4,5-trimethoxyphenyl)-2,4-pyrimidinediamine;
N4-(4-Hydroxyphenyl)-N2-(3,4,5-trimethoxyphenyl)-2,4-pyrimidinediamine and
N4-(4-(3-Aminopropoxy)phenyl)-N2-(3,4,5-trimethoxyphenyl)-2,4-pyrimidinediamine;
and the salts, solvates, hydrates and N-oxides thereof.

Compounds according to the invention are potent and selective inhibitors of protein kinases as demonstrated by differential inhibition of enzymes such as EGFr kinase, p56$^{lck}$ kinase, ZAP-70 kinase, Csk kinase and p59$^{fyn}$ kinase. The ability of the compounds to act in this way may be simply determined by employing tests such as those described in the Examples hereinafter.

The compounds according to the invention are thus of particular use in the prophylaxis and treatment of diseases in which inappropriate protein tyrosine kinase action plays a role, for example in autoimmune diseases such as rheumatoid arthritis, multiple sclerosis, and systemic lupus erythematosus, in transplant rejection, in graft v host disease, in hyperproliferative disorders such as tumours, psoriasis, in pannus formation in rheumatoid arthritis, restenosis following angioplasty and atherosclerosis, and in diseases in which cells receive pro-inflammatory signals such as asthma, inflammatory bowel disease and pancreatitis.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $R^1$–$R^7$ and X when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1981]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) wherein X is a direct bond may be prepared by reaction of a guanidine of formula (2):

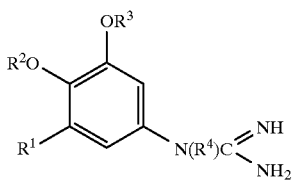

(2)

or a salt thereof with an enaminone of formula (3):

$$R^7COC(R^6)C(R^5)N(R^{15})(R^{16}) \quad (3)$$

where $R^{15}$ and $R^{16}$, which may be the same or different is each a $C_{1-6}$ alkyl group.

The reaction may be performed in a solvent, for example a protic solvent such as an alcohol, e.g. ethanol, methoxyethanol or propanol, optionally in the presence of a base e.g. an alkali metal base, such as sodium hydroxide or potassium carbonate, at an elevated temperature, e.g. the reflux temperature.

Salts of the compounds of formula (2) include acid salts such as inorganic acid salts e.g. hydrochlorides or nitrates.

Intermediate guanidines of formula (2) may be prepared by reaction of the corresponding aniline of formula (4):

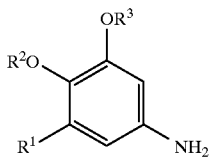

(4)

with cyanamide at an elevated temperature.

The reaction may be performed in a solvent such as ethanol at an elevated temperature, e.g. up to the reflux temperature. Where it is desired to obtain a salt of a guanidine of formula (2), the reaction may be performed in the presence of a concentrated acid, e.g. hydrochloric or nitric acid.

The anilines of formula (4) are either known compounds or may be obtained by conventional procedures, for example by hydrogenation of the corresponding nitro derivatives using for example hydrogen in the presence of a metal catalyst in a suitable solvent, for example as more particularly described in the interconversion reactions discussed below or by use of the corresponding nitro derivative and a reducing agent such as a sodium hydrosulphite in a solvent such as ethanol at an elevated temperature such as the reflux temperature. The nitrobenzenes for this particular reaction are either known compounds or may be prepared using similar methods to those used for the preparation of the known compounds, for example by treatment of the corresponding benzene with nitric acid in the presence of an acid such as acetic acid at around ambient to the reflux temperature.

Intermediate enaminones of formula (3) may be prepared by reaction of an acetyl derivative $R^7COCH_2R^6$ with an acetal $(R^{16})(R^{15})NCR^5(OCH_3)_2$ at an elevated temperature. The starting materials for this reaction are either known compounds of may be prepared by methods analogous to those used for the preparation of the known compounds.

In another process according to the invention, a compound of formula (1) where X is a linker atom or group may be prepared by reaction of an intermediate of formula (5)

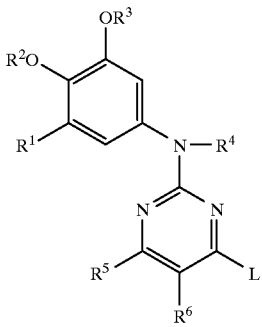

(5)

where L is a leaving atom or group, with a reagent $R^7X^2H$ where X2 is a linking atom or group as defined above.

Particular leaving atoms or groups represented by L include for example halogen atoms, e.g. bromine, iodine or chlorine atoms, and sulphonyloxy groups, e.g. alkylsulphonyloxy groups, such as trifluoromethylsulphonyloxy, and arylsulphonyloxy groups, such as p-toluenesulphonyloxy.

The reaction may be performed in the presence of a base, for example an organic base such as an organic amine, e.g. triethylamine or an inorganic base, for example a hydride such as sodium hydride, an alkoxide such as potassium t-butoxide, or a carbonate such as caesium or potassium carbonate, where necessary in the presence of a dipolar aprotic solvent such as an ether, e.g. a cyclic ether such as tetrahydrofuran, or an amide, e.g. a substituted amide such as dimethylformamide, at a suitable temperature e.g. from around room temperature to around 90° C.

Intermediates of formula (5) may be prepared by reaction of the corresponding pyrimidinones (where —N═C(L)— in formula (5) is —NH—C(O)—) with a halide using standard procedures, for example by reaction with a reagent $PO(Hal)_3$ (where Hal is a halogen atom), e.g. $POCl_3$, or $RSO_2Hal$ (where R is an optionally substituted alkyl or aryl group) where necessary at an elevated temperature.

The starting pyrimidinones may be prepared by reaction of a guanidine of formula (2) or a salt thereof with a β-ketoester [for example a compound $CH_3CH_2C(O)OCH(R^6)C(O)R^5$ (where $R^5$ is an optionally substituted alkyl, alkenyl or alkynyl group)] or a functional analogue thereof where it is desired to obtain compounds wherein $R^5$ is a hydrogen atom, in the presence of a base, for example an alkoxide such as sodium methoxide in a solvent, for example a protic solvent, such as an alcohol, e.g. methanol at an elevated temperature, e.g. up to around the reflux temperature.

In a further process according to the invention, a compound of formula (1) may be prepared by displacement of a leaving atom or group in a pyrimidine of formula (6):

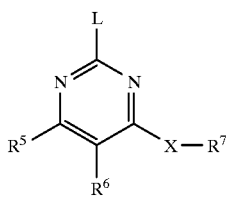

(6)

[where L is a leaving atom or group as defined above] with an aniline of formula (4).

The reaction may be performed at an elevated temperature, for example the reflux temperature, where necessary in the presence of a solvent, for example a ketone such as acetone, an alcohol such as ethanol or 2-ethoxyethanol or an aromatic hydrocarbon such as toluene, optionally in the presence of a base, for example an organic amine such as triethylamide or pyridine, or an acid, for example an inorganic acid such as hydrochloric acid.

Intermediate pyrimidines of formula (6) may be prepared by displacement of a leaving group from a pyrimidine of formula (7):

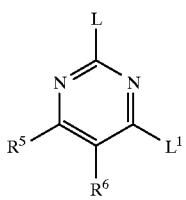

(7)

[where $L^1$ is a leaving atom or group as described above for the group L] using a nucleophilic reagent $R^7XH$. The reaction may be performed as just described in relation to the preparation of compounds of formula (1) from the intermediate pyrimidines of formula (6).

The pyrimidines of formula (7) and the nucleophilic reagents $R^7XH$ are either known compounds or may be prepared using methods analogous to those used for the preparation of the known compounds.

In another process according to the invention, a compound of formula (1) wherein X is a —C(O)— group may be prepared by treating a carboxamide of formula (8):

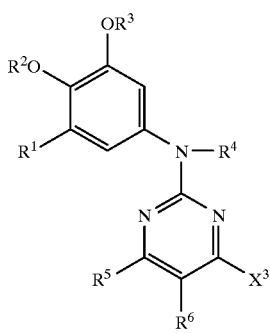

(8)

[where $X^3$ is a carboxamide group] with a reagent $R^7MHal^1$ (where M is a metal atom such as an zinc atom and $Hal^1$ is a halogen atom such as a bromine atom).

The group $X^3$ in intermediates of formula (8) may be for example a group —$CONR^{15}R_{16}$ or —$CON(R^{15})(OR^{16})$.

The reaction may be performed in a solvent such as an ether, e.g. a cyclic ether such as a tetrahydrofuran, at a low temperature, e.g. around –78° C.

Intermediate carboxamides of formula (8) may be prepared by reaction of the corresponding acid of formula (9):

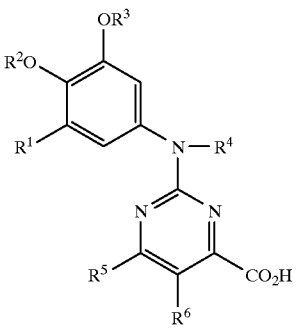

(9)

or a reactive derivative thereof with a reagent $R^{15}R^{16}NH$ or $R^{15}R^{16}ONH$ in the presence of a base e.g. an organic amine such as triet hylamine in a solvent such as dichloromethane at a low temperature, e.g. around –20° to 0° C.

Intermediate acids of formula (9) may be prepared by heating the corresponding nitrile in the presnce of a base such as sodium hydroxide in a solvent such as ethanol. The nitrile starting material may be prepared by heating 2-chloro-4-cyano-pyrimidine with the appropriate aniline in the presence of a base such as triethylamine in a solvent such as ethanol at the reflux temperature.

Acidss of formula (9) may also be used to generate compounds of formula (1) wherein X is a —NHC(O)O— group by reaction with an azide, for example diphenylphosphorylazide, and an alcohol $R^7OH$ in the presence of a base such as triethylamine at an elevated temperature, e.g. the reflux temperature.

Compounds of formula (1) may also be prepared by interconversion of other compounds of formula (1) and it is to be understood that the invention extends to such interconversion processes. Thus, for example, standard substitution approaches employing for example alkylation, arylation, acylation, thioacylation, sulphonylation, formylation or coupling reactions may be used to add new substituents to and/or extend existing substituents in compounds of formula (1). Alternatively existing substituents in compounds of formula (1) may be modified by for example oxidation, reduction or cleavage reactions to yield other compounds of formula (1).

The following describes in general terms a number of approaches which can be employed to modify existing $R^1$, $R^2$, $R^3$, $R^4$, $R^5$ and/or $R^6$ groups in compounds of formula (1). It will be appreciated that each of these reactions may only be possible where an appropriate functional group exists in a compound of formula (1). Equally, any of the following reactions may be used to generate appropriately substituted intermediates of formulae (2), (4), (5), (6) and (7) for use in the preparation of compounds of formula (1).

Thus, for example alkylation or arylation of a compound of formula (1) may be achieved by reaction of the compound with a reagent $R^4L$, AlkL or ArL, where $R^4$, Alk, Ar and L are as previously defined.

The alkylation or arylation reaction may be carried out in the presence of a base, e.g. an inorganic base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at around 0° C. to around 40° C.

In a variation of this process the leaving group L may be alternatively part of the compound of formula (1) and the reaction performed with an appropriate nucleophilic reagent in a solvent such as an alcohol, e.g. ethanol, at an elevated temperature, e.g. the reflux temperature.

In another general example of an interconversion process, a compound of formula (1) may be acylated or thioacylated. The reaction may be performed for example with an acyl halide or anhydride in the presence of a base, such as a tertiary amine e.g. triethylamine in a solvent such as a halogenated hydrocarbon, e.g. dichloromethane or carbon tetrachloride, or an alcohol, e.g. methanol at for example ambient temperature, or by reaction with a thioester in an inert solvent such as tetrahydrofuran at a low temperature such as around 0° C. The reaction is particularly suitable for use with compounds of formula (1) containing primary or secondary amino groups.

In a further general example of an interconversion process, a compound of formula (1) may be formylated, for example by reaction of the compound with a mixed anhydride $HCOOCOCH_3$ or with a mixture of formic acid and acetic anhydride.

Compounds of formula (1) may be prepared in another general interconversion reaction by sulphonylation, for example by reaction of the compound with a reagent $AlkS(O)_2L$, or $ArS(O)_2L$ in the presence of a base, for example an inorganic base such as sodium hydride in a solvent such as an amide, e.g. a substituted amide such as dimethylformamide at for example ambient temperature. The reaction may in particular be performed with compounds of formula (1) possessing a primary or secondary amino group.

In further examples of interconversion reactions according to the invention compounds of formula (1) may be prepared from other compounds of formula (1) by modification of existing functional groups in the latter.

Thus in one example, ester groups —$CO_2Alk^1$ in compounds of formula (1) may be converted to the corresponding acid [—$CO_2H$] by acid- or base-catalysed hydrolysis or by catalytic hydrogenation depending on the nature of the group $Alk^1$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol. Catalytic hydrogenation may be carried out using for example hydrogen in the presence of a metal catalyst, for example palladium on a support such as carbon in a solvent such as an ether, e.g. tetrahydrofuran or an alcohol, e.g. methanol. Similarly, base-catalysed hydrolysis with for example an alkali metal hydroxide such as sodium hydroxide in a solvent such as an alcohol e.g. ethanol may be used to convert a >$NSO_2Alk$ or >$NSO_2Ar$ group to a >N-H group.

In a second example, —$OAlk^2$ [where $Alk^2$ represents an alkyl group such as a methyl group] groups in compounds of formula (1) may be cleaved to the corresponding alcohol [—OH] by reaction with boron tribromide in a solvent such as a halogenated hydrocarbon, e.g. dichloromethane at a low temperature, e.g. around −78° C.

Alcohol [—OH] groups may also be obtained by hydrogenation of the corresponding —$OCH_2Ar$ group using for example hydrogen in the presence of a metal catalyst, for example palladium on a support such as carbon in a solvent such as ethanol in the presence of ammonium formate. In another example, —OH groups may be generated from the corresponding ester [—$CO_2Alk$] by reduction using for example a complex metal hydride such as lithium aluminium hydride.

In a further example, alcohol —OH groups in compounds of formula (1) may be converted to a corresponding —OAlk or —OAr group by coupling with a reagent AlkOH or ArOH in a solvent such as tetrahydrofuran in the presence of a phosphine, e.g. triphenylphosphine and an activator such as diethyl-, diisopropyl-, or dimethylazodicarboxylate.

In another example of an interconversion reaction, amines of formula (1) may be alkylated using a reductive alkylation process employing an aldehyde and a borohydride, for example sodium triacetoxyborohydride, in a solvent such as dichloromethane, in the presence of an acid such as acetic acid at around ambient temperature.

Aminosulphonylamino [—$NHSO_2NH_2$] groups in compounds of formula (1) may be obtained, in another example, by reaction of a corresponding amine [—$NH_2$] with sulphamide in the presence of an organic base such as pyridine at an elevated temperature, e.g. the reflux temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation as just described, or by chemical reduction using for example a metal, e.g. tin or iron, in the presence of an acid such as hydrochloric acid, optionally in a solvent such as an alcohol, e.g. methanol.

In a further example of an interconversion process, a tetrazole substituent may be obtained from the corresponding nitrile by treatment of the latter with an azide, e.g. sodium azide, in a solvent such as a substituted amine, e.g. dimethylformamide at an elevated temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C to 80° C., or alternatively by reaction with a peracid such as peracetic acid or 3-chloroperoxybenzoic acid in a solvent, e.g. dichloromethane, at ambient temperature.

Where salts of compounds of formula (1) are desired, these may be prepared by conventional means, for example by reaction of a compound of formula (1) with an appropriate acid or base in a suitable solvent or mixture of solvents, e.g. an organic solvent such as an ether, e.g. diethylether, or an alcohol, e.g. ethanol.

The following Examples illustrated the invention. In the Examples all $^1$Hnmr were run at 300 MHz unless specified otherwise. All temperatures are in 0° C. The following abbreviations are used: DMSO—dimethylsulphoxide; DMF—dimethylformamide; THF—tetrahydrofuran.

EXAMPLE 1

4-Phenyl-N-(3,4,5-trimethoxyphenyl)-2-pyrimidineamine

To a solution of 3,4,5-(trimethoxyphenyl)guanidine nitrate (1.89 g, 6.57 mmol) and 3-dimethylamino-1-phenyl-2-propen-1-one (1.15 g, 6.57 mmol) in propan-2-ol (20 ml) was added powdered sodium hydroxide (289 mg, 7.23 mmol) and the mixture refluxed for 18 h. On cooling (0°) the resulting precipitate was collected and washed with propan-2-ol and water, and then subjected to column chromatography [methanol-CH$_2$CH$_2$] to afford the title compound (730 mg) after recrystallisation from ethyl acetate as a yellow solid m.p. 146°. δ$_H$ (CDCl$_3$) 3.85 (3H, s), 3.91 (6H, s), 7.07 (2H, s), 7.17 (1H, d, J 5.2 Hz), 7.18 (1H, s, NH), 7.46–7.50 (3H, m), 8.10 (2H, m), and 8.46 (1H, d, J 5.2 Hz).

The guanidine starting material was prepared by heating a mixture of 3,4,5-trimethoxyaniline (5.49 g, 30.0 mmol), cyanamide [Aldrich, 50% solution in water w/v] (3.50 ml, 45.0 mmol) and concentrated nitric acid (2.10 ml, 300 mmol) in ethanol (30 ml). The solid which formed on cooling to room temperature was collected by filtration, washed with ethanol and dried in vacuo to give the desired product (4.60 g) as a grey solid m.p. 187°. δ$_H$ (d$^6$DMSO) 3.65 (3H, s), 3.77 (6H, s), 6.54 (2H, s), 7.27 (4H, br s), and 9.46 (1H, s).

The following compounds of Examples 2–35 were prepared in a similar manner using the above guanidine starting material and the appropriate enaminone:

EXAMPLE 2

4-(3-Pyridyl)-N-(3,4,5-trimethoxyphenyl)-2-pyrimidineamine from 3,4,5-(trimethoxyphenyl)guanidine nitrate (1.33 g, 4.60 mmol), 3-dimethylamino-1-(3-pyridyl)-2-propen-1-one (812 mg, 4.60 mmol) and sodium hydroxide (203 mg, 5.07 mmol) to give the title compound (290 mg) as a green solid m.p. 155°. δ$_H$ (CDCl$_3$) 3.63 (3H, s), 3.78 (6H, s), 7.28 (2H, s), 7.47 (1H, d, J 5.1 Hz), 7.56 (1H, m), 8.49 (1H, m), 8.58 (1H, d, J 5.1 Hz), 8.71 (1 H, dd, J 4.8,1.5 Hz), 9.35 (1 H, d, J 2.0 Hz) and 9.61 (1H, s).

EXAMPLE 3

4-(4-Pyridyl)-N-(3,4,5-trimethoxyphenyl)-2-pyrimidineamine from 3,4,5-(trimethoxyphenyl)guanidine nitrate (1.44 g, 5.0 mmol), 3-dimethylamino-1-(4-pyridyl)-2-propene-1-one (880 mg, 5.0 mmol) and sodium hydroxide (220 mg, 5.5 mmol) to give the title compound (765 mg) as a green solid m.p. 205°. δ$_H$ (d$^6$DMSO) 3.63 (3H, s), 3.79 (6H, s), 7.27 (2H, s), 7.49 (1H, d, J 5.1 Hz), 8.08 (2H, dd, J 4.5, 1.6 Hz), 8.64 (1H, d, J 5.1 Hz), 8.76 (2H, dd, J 4.5,1.6 Hz), and 9.66 (1H, br s).

EXAMPLE 4

4-(2-Furyl)-N-3,4,5-(trimethoxyphenyl)-2-pyrimidineamine from 3,4,5-(trimethoxyphenyl)guanidine nitrate (1.66 g, 5.75 mmol), 3-dimethylamino-1-(2-furyl)-2-propen-1-one) (950 mg, 5.75 mmol) and sodium hydroxide (253 mg, 6.33 mmol) to give the title compound (350 mg) as a yellow solid m.p. 139°. δ$_H$ (CDCl$_3$) 3.83 (3H, s), 3.90 (6H, s), 6.56 (1H, m), 7.01 (2H, s), 7.06 (1H, d, J 5.1 Hz), 7.18 (1H, m), 7.25 (1H, s), 7.58 (1H, d, J 2.3 Hz), and 8.42 (1H, d, J 5.1 Hz).

EXAMPLE 5

4-(3,4,5-Trimethoxyphenyl)-N-(3,4,5-trimethoxyphenyl)-2-pyrimidineamine from 3,4,5-(trimethoxyphenyl)guanidine nitrate (1.08 g, 3.77 mmol), 3-dimethylamino-1-(3,4,5-trimethoxyphenyl)-2-propen-1-one (1.0 g, 3.77 mmol) and sodium hydroxide (166 mg) to give the title compound (67 mg) as a colourless solid m.p. 187°. δ$_H$ (CDCl$_3$) 3.83 (3H, s), 3.88 (6H, s), 3.92 (3H, s), 3.94 (6H, s), 6.99 (2H, s), 7.09 (1H, d, J 5.2 Hz), 7.23 (1H, br s), 7.32 (2H, s) and 8.45 (1H, d, J 5.2 Hz).

EXAMPLE 6

4-(5-(2,3-Dihydrobenzofuryl))-N-(3,4,5-trimethoxyphenyl)-2-pyrimidineamine from 3,4,5-(trimethoxyphenyl)guanidine nitrate (1.19 g, 4.14 mmol), 1-(5-(2,3-dihydrobenzofuryl)-3-dimethylamino-2-propen-1-one (900 mg, 4.14 mmol) and sodium hydroxide (182 mg, 4.56 mmol) to give the title compound (450 mg) as a yellow solid m.p.160°.δ$_H$ (CDCl$_3$) 3.26 (2H, t, J 8.7 Hz), 3.83 (3H, s), 3.90 (6H, s), 4.66 (2H, t, J 8.7 Hz), 6.86 (1H, d, J 8.3 Hz), 7.06 (3H, m), 7.17 (1H, s), 7.88 (1H, d, J 8.3 Hz), 8.02 (1H, s), and 8.38 (1H, d, J 5.3 Hz).

EXAMPLE 7

4-(1-Phenylsulphonylindol-3-yl)-N-(3,4,5-trimethoxyphenyl)-2-pyrimidineamine from 3,4,5-(trimethoxyphenyl)guanidine nitrate (820 mg, 2.84 mmol), 3-dimethylamino-1-(1-phenylsulphonylindol-3-yl)-2-propen-1-one (1.0 g, 2.84 mmol), and sodium hydroxide (125 mg, 3.12 mmol) to give the title compound (380 mg) as a yellow solid m.p. 202°. δ$_H$ (d$^6$DMSO) 3.30 (3H, s), 3.63 (6H, s), 7.19 (2H, s), 7.33 (1H, t, J 7.3Hz), 7.44 (2H, m), 7.61 (2H m), 7.71 (1H, m), 7.99 (1H, d, J 8.3 Hz), 8.09 (2H, d, J 7.4 Hz), 8.49 (1H, d, J 5.2 Hz), 8.60 (1H, d, J 7.9 Hz), 8.74 (1H, s) and 9.46 (1H, s).

EXAMPLE 8

4-(2-Thiazolyl)-N-(3,4,5-trimethoxyphenyl)-2-pyrimidineamine from 3,4,5-(trimethoxyphenyl)guanidine nitrate (1.27 g, 4.40 mmol), 3-dimethylamino-1-(2-thiazolyl)-2-propen-1-one (802 mg, 4.40 mmol), and sodium hydroxide (194 mg, 4.84 mmol) to give the title compound (520 mg) as a green solid m.p. 159°. δ$_H$ (d$^6$DMSO) 3.63 (3H, s), 3.82 (6H, s), 7.24 (2H, s), 7.45 (1H, d, J 4.9 Hz), 8.07 (1H, d, J 3.0 Hz), 8.62 (1H, d, J 4.8 Hz) and 9.70 (1H, s).

EXAMPLE 9

4-(3-Thienyl)-N-(3,4,5-Trimethoxyphenyl)-2-pyrimidineamine from 3,4,5-(trimethoxyphenyl)guanidine nitrate (1.27 g, 4.41 mmol), 3-dimethylamino-1-(3-thienyl)-2-propen-1-one (0.80 g, 4.41 mmol) to give the title compound (365 mg) as a yellow solid m.p. 163°. δ$_H$ (d$^6$DMSO) 3.62 (3H, s), 3.78 (6H, s), 7.26–7.27 (3H, m), 7.68–7.71 (1H, m), 7.78 (1H, d, J 4.9 Hz), 8.34–8.36 (1H, m), 8.47 (1H, d, J 5.0 Hz) and 9.44 (1H, s).

EXAMPLE 10

4-(2-Naphthyl)-N-(3,4,5-trimethoxyphenyl)-2-pyrimidineamine from 3,4,5-(trimethoxypheny)guanidine nitrate (1.02 g, 3.55 mmol), 3-dimethylamino-1-(2-naphthyl)-2-propen-1-one (800 mg, 3.55 mmol) and sodium hydroxide (156 mg, 3.90 mmol) to give the title compound (310 mg) as a yellow solid m.p. 156°. $\delta_H$ (d⁶DMSO) 3.64 (3H, s), 3.82 (6H, s), 7.36 (2H, s), 7.53 (1H, d, J 6.2 Hz), 7.58–7.61 (2H, m), 7.97–8.07 (3H, m), 8.29 (1H, d, J 8.5 Hz), 8.58 (1H, d, J 5.1 Hz), 8.76 (1H, s), and 9.58 (1H, br s).

EXAMPLE 11

4-(3-Nitrophenyl)-N-(3,4,5-trimethoxyphenyl)-2-pyrimidineamine from 3,4,5-(trimethoxyphenyl)guanidine nitrate (3.93 g, 13.63 mmol), 3-dimethylamino-1-(3-nitrophenyl)-2-propen-1-one (3.0 g, 13.63 mmol) and sodium hydroxide (545 mg, 13.63 mmol) to give the title compound (250 mg) as a yellow solid. m.p. 184–185°. MS m/z 383 (M+H)⁺.

EXAMPLE 12

4-(4-Nitrophenyl)-N-(3,4,5-trimethoxyphenyl)-2-pyrimidineamine from 3,4,5-(trimethoxyphenyl)guanidine nitrate (1.3 g, 4.5 mmol), 3-dimethylamino-1-(4-nitrophenyl)-2-propen-1-one (1.0 g, 4.5 mmol) and sodium hydroxide (200 mg) to give the title compound (550 mg) as an orange solid m.p. 196°. MS m/z 383 (M+H)⁺.

EXAMPLE 13

4-(3-Bromophenyl)-N-(3,4,5-trimethoxyphenyl)-2-pyrimidineamine from 3,4,5-(trimethoxyphenyl)guanidine nitrate (1.63 g, 5.66 mmol), 1-(3-bromophenyl)-3-dimethylamino-2-propen-1-one (1.5 g, 5.66 mmol) and sodium hydroxide (250 mg, 6.23 mmol) to give the title compound (785 mg) as a yellow solid m.p. 145°. MS m/z 418 (M+H)⁺.

EXAMPLE 14

4-(Pyrrol-2-yl)-N-(3,4,5-trimethoxyphenyl)-2-pyrimidineamine from 3,4,5-(trimethoxyphenyl)guanidine nitrate (1.15 g, 4.0 mmol), 3-dimethylamino-1-(pyrrol-2-yl)-2-propen-1-one (656 g, 4.0 mmol) and sodium hydroxide (176 mg, 4.4 mmol) to give the title compound (10 mg) as a yellow solid m.p. 150°. MS m/z 327 (M+H)⁺.

EXAMPLE 15

4-(3,4,-Methylenedioxyphenyl)-N-(3,4,5-trimethoxyphenyl)-2-pyrimidineamine from 3,4,5-(trimethoxyphenyl)guanidine nitrate (1.15 g, 4.0 mmol), 3-dimethylamino-1-(3,4-methylenedioxyphenyl)-2-propen-1-one (8.76 g, 4.0 mmol) and sodium hydroxide (176 mg) to give the title compound (160 mg) as a yellow solid m.p. 180°. MS m/z 382 (M+H)⁺.

EXAMPLE 16

4-(Pyrazin-2-yl)-N-(3,4,5-trimethoxyphenyl)-2-pyrimidineamine from 3,4,5-(trimethoxyphenyl)guanidine nitrate (1.15 g, 4.0 mmol), 3-dimethylamino-1-(pyraz-2-yl)-2-propen-1-one (708 mg, 4.0 mmol) and sodium hydroxide (176 mg) to give the title compound (254 mg) as a yellow solid. m.p. 181–182°. MS m/z 340 (M+H)⁺.

EXAMPLE 17

4-(tert-Butyl)-N-(3,4,5-trimethoxyphenyl)-2-pyrimidineamine from 3,4,5-(trimethoxyphenyl)guanidine nitrate (1.2 g, 4.2 mmol), 1-terf-butyl-3-dimethylamino-2-propen-1-one (650 mg, 4.2 mmol) and sodium hydroxide (185 mg) to give the title compound (90 mg) as a white solid m.p. 122°. MS m/z 318 (M+H)⁺.

EXAMPLE 18

4-(1,2,3,4-Tetrahydronaphthalen-6-yl)-N-(3,4,5-trimethoxyphenyl)-2-pyrimidineamine from 3,4,5-(trimethoxyphenyl)guanidine nitrate (1.0 g, 435 mmol), 3-dimethylamino-1-(1,2,3,4-tetrahydronaphthalen-6-yl)-2-propen- 1-one (801 mg, 3.5 mmol) and sodium hydroxide (155 mg, 3.85 mmol) to give the title compound (120 mg) as a yellow solid m.p. 150–151°. MS m/z 392 (M+H)⁺.

EXAMPLE 19

4-(2,2-Dimethyl-3,4-dihydro-2H-benzo[b]oxin-6-yl)-N-(3,4,5-trimethoxyphenyl)-2-pyrimidineamine from 3,4,5-(trimethoxyphenyl)guanidine nitrate (1.15 g, 4.0 mmol), 3-dimethylamino-1-(2,2-dimethyl-3,4-dihydro-2H-benzo[b]oxin-6-yl)-2-propen-1-one (1.04 g, 4.0 mmol) and sodium hydroxide (180 mg, 4.4 mmol) to give the title compound (120 mg) as a pale yellow solid m.p. 149–150°. MS m/z 422.3 (M+H)⁺.

EXAMPLE 20

4-(Benzothiazol-2-yl)-N-(3,4,5-trimethoxyphenyl)-2-pyrimidineamine from 3,4,5-(trimethoxyphenyl)guanidine nitrate (1.72 g, 6.0 mmol), 1-(benzothiazol-2-yl)-3-dimethylamino-2-propen-1-one (1.39 g, 6.0 mmol) and sodium hydroxide (270 mg, 6.6 mmol) to give the title compound (420 mg) as a yellow solid m.p. 182–183°. MS m/z 395 (M+H)⁺.

EXAMPLE 21

4-(2-Nitrothien-5-yl)-N-(3,4,5-trimethoxyphenyl)-2-pyrimidineamine from 3,4,5-(trimethoxyphenyl)guanidine nitrate (1.27 g, 4.4 mmol), 3-dimethylamino-1-(2-nitrothien-5-yl)-2-propen-1-one (1.0 g, 4.4 mmol) and sodium hydroxide (186 mg, 4.9 mmol) to give the title compound (540 mg) as a dark red solid m.p. 182–183°. MS m/z 389 (M+H)⁺.

EXAMPLE 22

4-(3-Methoxyphenyl)-N-(3,4,5-trimethoxyphenyl)-2-pyrimidineamine from 3,4,5-(trimethoxyphenyl)guanidine nitrate (1.41 g, 4.84 mmol), 3-dimethylamino-1-(3-methoxyphenyl)-2-propen-1-one (1.0 g, 4.88 mmol) and sodium hydroxide (216 mg, 5.4 mmol) to give the title compound (275 mg) as a yellow solid m.p. 155–156°. MS m/z 368 (M+H)⁺.

EXAMPLE 23

4-(2-Pyridyl)-N-(3,4,5-trimethoxyphenyl)-2-pyrimidineamine from 3,4,5-(trimethoxyphenyl)guanidine nitrate (1.99 g, 6.9lmmol), 3-dimethylamino-1-(2-pyridyl)-2-propen-1-one (1.229, 6.91 mmol) and sodium hydroxide (276 mg, 6.9 mmol) to give the title compound (154 mg) as a yellow solid m.p. 185°. MS m/z 33 9 (M+H)+.

EXAMPLE 24

4-(4-tert-Butoxycarbonylaminophenyl)-N-(3,4,5-trimethoxyphenyl)-2-pyrimidineamine from 3,4,5-(trimethoxyphenyl)guanidine nitrate (10.9 g, 37.8 mmol), 1-(4-tert-butoxycarbbonylaminophenyl)-3-dimethylamino-2-propen-1-one (10.0 g, 34.4 mmol) and sodium hydroxide (1.52 g, 37.8 mmol) to give the title compound (5.4 g) as a yellow solid m.p. 158–159°. MS m/z 453 (M+H)+.

EXAMPLE 25

4-(3-Hydroxyphenyl)-N-(3,4,5-trimethoxyphenyl)-2-pyrimidineamine from 3,4,5-(trimethoxyphenyl)guanidine nitrate (4.72 g, 16.4 mmol), 1-(3-tert-butyldimethylsilyloxyphenyl)-3-dimethylamino-2-propen- 1-one (5.0 g, 16.4 mmol) and sodium hydroxide (655 mg, 16.4 mmol) to give the title compound (2.0 g) as a light yellow solid m.p. 191–192°. MS m/z 354 (M+H)+.

EXAMPLE 26

4-(5-Thiazolyl)-N-(3,4,5-trimethoxyphenyl)-2-pyrimidineamine from 3,4,5-(trimethoxyphenyl)guanidine nitrate (634 mg, 2.2 mmol), 3-dimethylamino-1-(5-thiazolyl)-2-propen-1-one (330 g, 1.81 mmol) and sodium hydroxide (88 mg, 2.2 mmol) to give the title compound (42 mg) as a yellow solid m.p. 171°. MS m/z 345 (M+H)+.

EXAMPLE 27

4-(4-Cyanophenyl)-N-(3,4,5-trimethoxyphenyl)-2-pyrimidineamine from 3,4,5-(trimethoxyphenyl)guanidine nitrate (17.0 g, 59.0 mmol), 1-(4-cyanophenyl)-3-dimethylamino-2-propen-1-one (11.82 g, 58.0 mmol) and sodium hydroxide (2.36 mg, 59.0 mmol) to give the title compound (11.66 g) as a green solid m.p. 183°. MS m/z 363 (M+H)+.

EXAMPLE 28

4-(4-Ethoxycarbonylphenyl)-N-(3,4,5-trimethoxyphenyl)-2-pyrimidineamine from 3,4,5-(trimethoxyphenyl)guanidine nitrate (11.66 g, 40.5 mmol), 3-dimethylamino-1-(4-ethoxycarbonylphenyl)-2-propen-1-one (10.0 g, 40.5 mmol) and sodium hydroxide (1.62 g, 40.5 mmol) to give the title compound (3.21 g) as a yellow solid m.p. 181–182°. MS m/z 410 (M+H)+.

EXAMPLE 29

4-(1-Naphthyl)-N-(3,4,5-trimethoxyphenyl)-2-pyrimidineamine from 3,4,5-(trimethoxyphenyl)guanidine nitrate (2,94 g, 10.22 mmol), 3-dimethylamino-1-(1-naphthyl)-2-propen-1-one (2.30 g, 10.22 mmol) and sodium hydroxide (409 mg, 10.22 mmol) to give the title compound (750 mg) as a yellow solid m.p. 130–133°. MS m/z 444 (M+H)+.

EXAMPLE 30

4(4,5-Dimethylthiazol-2-yl)-N-(3,4,5-trimethoxyphenyl)-2-pyrimidineamine from 3,4,5-(trimethoxyphenyl)guanidine nitrate (4.99 g, 6.91 mmol), 3-dimethylamino-1-(4,5-dimethylthiazol-2-yl)-2-propen-1-one (3.64 g, 17.3 mmol) and sodium hydroxide (720 mg, 18 mmol) to give the title compound (490 mg) as a yellow solid m.p. 207°. MS m/z 373 (M+H)+.

EXAMPLE 31

4-(4-Methoxyphenyl)-N-(3,4,5-trimethoxyphenyl)-2-pyrimidineamine from 3,4,5-(trimethoxyphenyl)guanidine nitrate (8.16 g, 28.3 mmol), 3-dimethylamino-1-(4-methoxyphenyl)-2-propen-1-one (5.5 g, 28.3 mmol) and sodium hydroxide (1.13 g, 28.3 mmol) to give the title compound (3.4 g) as an orange solid m.p. 148–150°. MS m/z 368 (M+H)+.

EXAMPLE 32

4-(4-Benzyloxyphenyl)-N-(3,4,5-trimethoxyphenyl)-2-pyrimidineamine from 3,4,5-(trimethoxyphenyl)guanidine nitrate (9.0 g, 31.25 mmol), 1-(4-benzyloxyphenyl)-3-dimethylamino-2-propen-1-one (8.88 g, 31.25 mmol) and sodium hydroxide (1.25 g, 31.25 mmol) to give the title compound (1 1.0 g) as a yellow solid m.p. 171–172°. MS m/z 444 (M+H)+.

EXAMPLE 33

4-(5-(2-Hydroxyethyl)-4-methylthiazol-2-yl)-N-(3,4,5-trimethoxyphenyl)-2-pyrimidineamine from 3,4,5-(trimethoxyphenyl)guanidine nitrate (1.22 g, 4.23 mmol), 1-(5-(2-tert-butyldimethylsilyloxyethyl)-4-methylthiazol-2-yl)-3-dimethylamino-2-propen-1-one (1.50 g, 4.23 mmol) and sodium hydroxide (200 mg, 5.0 mmol) to give the title compound (210 mg) as an orange solid m.p. >190° (decomp). MS m/z 403 (M+H)+.

EXAMPLE 34

4-(4-Bromophenyl)-N-(3,4,5-trimethoxyphenyl)-2-pyrimidineamine from 3,4,5-(trimethoxyphenyl)guanidine nitrate (2.26 g, 7.80 mmol), 1-(4-bromophenyl)-3-dimethylamino-2-propen-1-one (2.0 g, 7.80 mmol) and sodium hydroxide (346 mg, 8.60 mmol) to give the title compound (1.0 g) as a green solid m.p. 179°. MS m/z 416 (M+H)+.

EXAMPLE 35

4-(2-Chloropyridin-5-yl)-N-(3,4,5-trimethoxyphenyl)-2-pyrimidineamine from 3,4,5-(trimethoxyphenyl)guanidine nitrate (16.42 g, 22.3 mmol), 1-(2-chloropyridin-5-yl)-3-dimethylamino-2-propen-1-one (4.70 g, 22.3 mmol) and sodium hydroxide (895 mg) to give the title compound (1.43 g) as a yellow solid m.p. 191–192°. MS m/z 373.2 (M+H)+.

EXAMPLE 36

4-(1-H-Indol-3-yl)-N-(3,4,5-trimethoxyphenyl)-2-pyrimidineamine

The compound of Example 7 (400 mg, 0.78 mmol) was suspended in ethanol (5 ml) and 4M sodium hydroxide (5

EXAMPLE 37

N-Methyl-4-(4-pyridyl)-N-(3,4,5-trimethoxyphenyl)-2-pyrimidineamine

A solution of the compound of Example 3 (650 mg, 1.92 mmol) in DMF (5ml) was added dropwise to a stirred suspension of 60% NaH (76 mg, 1.92 mmol) in DMF (5ml), cooled to 0° C. After 0.5 h iodomethane (0.13 ml, 2.11 mmol) was added dropwise and the resulting mixture was left to warm to room temperature over 20 h. The reaction was concentrated under reduced pressure and the resulting residue subjected to column chromatography to give the title compound (159 mg) as a pale green solid m.p. 139°. MS m/z 353 (M+H)+.

EXAMPLE 38

4-(2-Aminothien-5-yl)-N-(3,4,5-trimethoxyphenyl)-2-pyrimidineamine

A solution of the compound of Example 21 (380 mg, 0.98 mmol) was treated with ammonium formate (200 mg, 6.34 mmol) and 10% palladium on carbon (200 mg) at 650 for 24 h. On cooling, the catalyst was filtered off on a pad of celite and the filtrate concentrated under reduced pressure to give the title compound (100 mg) as a green solid m.p. 161–162°. MS m/z 389 (M+H)+.

The compounds of Examples 39 and 40 were prepared in a similar manner to the compound of Example 38:

EXAMPLE 39

4-(4-Aminophenyl)-N-(3,4,5-trimethoxyphenyl)-2-pyrimidineamine from the compound of Example 12 (800 mg, 2.09 mmol), ammonium formate (660 mg, 10.5 mmol) and 10% palladium on carbon (80 mg) to give the title compound (253 mg) as a yellow solid m.p. 195°. MS m/z 353 (M+H)+.

EXAMPLE 40

4-(3-Aminophenyl)-N-(3,4,5-trimethoxyphenyl)-2-pyrimidineamine from the compound of Example 11 (150 mg, 0.39 mmol), ammonium formate (150 mg, 2.38 mmol) and 10% palladium on carbon (100 mg) to give the title compound (120 mg) as a yellow solid m.p. 166–167°. MS m/z 353 (M+H)+.

EXAMPLE 41

4-(3-Acetamidophenyl)-N-(3,4,5-trimethoxyphenyl)-2-pyrimidineamine

To a solution of the compound of Example 40 (0.25 g, 0.71 mmol) in dry $CH_2Cl_2$ (40 ml) and triethylamine (0.11 ml) was added acetyl chloride (0.06 ml, 0.78 mmol) and the resulting mixture stirred at room temperature for 4 h. After washing with water (100 ml) and saturated aqueous $NaHCO_3$ (100 ml), the organic layer was dried ($MgSO_4$) and concentrated under reduced pressure. The residue was subjected to column chromatography [silica-ethyl acetate] to give after recrystallisation from ethyl acetate-hexane the title compound (163 mg) as a yellow solid. m.p. 162–164°. MS m/z 395 (M+H)+.

The compounds of Examples 42–44 were prepared in a similar manner to the compound of Example 41:

EXAMPLE 42

4-(4-Acetamidophenyl)-N-(3,4,5-trimethoxyphenyl)-2-pyrimidineamine from the compound of Example 39 (300 mg, 0.85 mmol), triethylamine (0.13 ml, 0.94 mmol) and acetyl chloride (0.07 ml, 0.94 mmol) to give the title compound (178 mg) as a yellow solid m.p. 239°. MS m/z 395 (M+H)+.

EXAMPLE 43

N-(3-(2-(3,4,5-Trimethoxyphenylamino)pyrimidin-4-yl)phenyl)-5-methylisoxazole-3-carboxamide from the compound of Example 40 (150 mg, 0.43 mmol), 5-methylisoxazole-3-carbonyl chloride (68 mg, 0.47 mmol) and triethylaminie (0.1 ml, 0.7 mmol) to give the title compound (7 mg) as a yellow solid m.p. 173–175°. MS m/z 462 (M+H)+.

EXAMPLE 44

N-(3-(2-(3,4,5-Trimethoxyphenylamino)pyrimidin-4-yl)phenyl)pyridine-3-carboxamide from the compound of Example 40 (250 mg, 0.71 mmol), nicotinoyl chloride hydrochloride (139 mg, 0.78 mmol), and triethylamine (0.2 ml, 2.3 mmol) to give the title compound (155 mg) as a yellow solid m.p. 140–143°. MS m/z 458 (M+H)+.

EXAMPLE 45

4-(3-(3-Phthalimidopropoxy)phenyl)-N-(3,4,5-trimethoxyphenyl)-2-pyrimidineamine

To a suspension of caesium carbonate (462 mg, 1.4 mmol) in dry DMF (10 ml) under a nitrogen atmosphere were added the compound of Example 25 (500 mg, 1.4 mmol) and 3-bromopropylphthalimide (380 mg, 1.4 mmol). The resulting mixture was stirred at room temperature for 4.5 h, followed by the addition of water (50 ml). The resulting precipitate was collected, washed with diethyl ether and recrystallised from ethyl acetate-hexane to give the title compound (620 mg) as an off-white solid m.p. 209°. MS m/z 541 (M+H)+.

The following compound was prepared in a similar manner:

EXAMPLE 46

4-(3-Propoxyphenyl)-N-(3,4,5-trimethoxyphenyl)-2-pyrimidineamine from the compound of Example 25 (350 mg, 0.99 mmol), iodopropane (168 mg, 0.99 mmol) and caesium carbonate (322 mg, 0.99 mmol) to give the title compound (187 mg) as an off-white solid m.p. 107°. MS m/z 396 (M+H)+.

EXAMPLE 47

4-(3-(2-Hydroxyethoxy)phenyl)-N-(3,4,5-trimethoxyphenyl)-2-pyrimidineamine

To a suspension of 60% NaH (dispersion in oil) (62 mg, 1.6 mmol) in DMF (15 ml) under a nitrogen atmosphere were added the compound of Example 25 (500 mg, 1.4 mmol) and ethylene carbonate (137 mg, 1.6 mmol). The resulting mixture was heated at 130° for 6 h. On cooling the reaction was diluted with water (30 ml), extracted with $CH_2Cl_2$ (3×25 ml), dried ($MgSO_4$) and concentrated under reduced pressure. The resulting residue was subjected to column chromatography [silica-ethyl acetate] to give the title compound (260 mg) as a yellow solid m.p. 70°. MS m/z 398 $(M+H)^+$.

EXAMPLE 48

4-(3-(3-Aminopropoxy)phenyl)-N-(3,4,5-trimethoxyphenyl)-2-pyrimidineamine dihydrochloride The compound of Example 45 (500 mg, 0.9 mmol) was suspended in ethanol (30 ml) containing hydrazine monohydrate (0.14 ml, 2.8 mmol) and the resulting mixture heated at reflux for 18 h. On cooling the resulting precipitate was filtered off and the filtrate concentrated under reduced pressure. The residue was suspended in $CH_2Cl_2$ (30 ml), extracted with 2N hydrochloric acid (2×30 ml) Combined acid layers were taken to pH 11 with 6N NaOH and extracted with $CH_2Cl_2$ (3×30 ml), the organic layers were dried ($MgSO_4$), and concentrated under reduced pressure. The residue was dissolved in ethanol (10 ml) and the solution saturated with HCl (g). The resulting precipitate was collected to give the title compound (137 mg) as an orange solid m.p. 236°. $\delta H$ ($d^6$-DMS)O 9.62 (1H, s), 8.54 (1H, d, J 5.2 Hz), 8.05 (2H, br s), 7.75 (2H, m), 7.45 (2H, m), 7.29 (2H, s), 7.14 (1H, d, J 7.3 Hz), 4.14 (2H, t, J 6.0Hz), 3.79 (6H, s), 3.62 (3H, s), 2.95 (2H, m) and 2.06 (2H, m). MS mz 411 $(M+H)^+$.

EXAMPLE 49

4-(4-Hydroxyphenyl)-N-(3,4,5-trimethoxyphenyl)-2-pyrimidineamine

A solution of the compound of Example 32 (1.06 g, 2.37 mmol) in ethanol (100 ml) was treated with ammonium formate (750 mg, 12.0 mmol) and 10% palladium on carbon (100 mg) and stirred at room temperature for 18 h, followed by heating at reflux for 18 h. On cooling the catalyst was removed by filtration through Celite® and the filtrate concentrated under reduced pressure. The resulting residue was recrystallised from ethyl acetate to give the title compound (760 mg) as a cream solid m.p. 200–202°. MS m/z 354 $(M+H)^+$.

EXAMPLE 50

4-(4-(3-Phthalimidopropoxy)phenyl)-N-(3,4,5-trimethoxyphenyl)-2-pyrimidineamine

To a supension of 60% NaH (dispersion in oil) (55 mg, 1.36 mmol) in DMF (10 ml) was added the compound of Example 49 (480 mg, 1.36 mmol) and 3-bromopropylphthalimide (365 mg, 1.36 mmol). The resulting mixture was stirred at room temperature for 6 h. After this time the reaction was concentrated under reduced pressure, the residue dissolved in ethyl acetate (50 ml), washed with water (50 ml), and dried ($MgSO_4$). The solvent was removed under reduced pressured to give the title compound (700 mg) as a buff solid . MS m/z 541 $(M+H)^+$.

EXAMPLE 51

4-(4-(3-Aminopropoxy)phenyl)-N-(3,4,5-trimethoxyphenyl)-2-pyrimidineamine

The compound was prepared in a manner analogous to the preparation of the compound of Example 48 from the compound of Example 50 (830 mg, 1 .54 mmol) and hydrazine monohydrate (0.23 ml, 4.62 mmol) to give the title compound (63 mg) as a white solid m.p. 161–162°. MS m/z 411 $(M+H)^+$.

EXAMPLE 52

4-(4-(2-Hydroxyethoxy)phenyl)-N-(3,4,5-trimethoxyphenyl)-2-pyrimidineamine

The compound was prepared in a manner analogous to the preparation of the compound of Example 47 from the compound of Example 49 (250 mg, 0.71 mmol), ethylene carbonate (70 mg, 6.78 mmol) and 60% sodium hydride (dispersion in oil) (30 mg, 0.78 mmol) to give the title compound (140 mg) as a yellow solid m.p 145–146°. MS m/z 398 $(M+H)^+$.

EXAMPLE 53

4-(4-(2-N,N-Dimethylaminoethoxy)phenyl)-N-(3,4,5-trimethoxyphenyl)-2-pyrimidineamine The compound of Example 49 (250 mg, 0.71 mmol), N,N-dimethylaminoethanol (69 mg, 0.78 mmol) and triphenylphosphine (205 mg, 0.78 mmol) were dissolved in dry THF (20 ml) under a nitrogen atmosphere and the mixture stirred for 0.5 h. Diethylazodicarboxylate (136 mg, 0.78 mmol) in THF (10 ml) was added dropwise and the reaction stirred for 48 h, after which time the solvent was removed under reduced pressure. The residue was dissolved in ethyl acetate (40 ml), washed with water (2×100 ml), dried ($MgSO_4$) and the solvent evaporated. The resulting solid was subjected to column chromatography [silica-ethyl acetate] to give the title compound (75 mg) as white crystals m.p. 140–147°. MS m/z 425 $(M+H)^+$.

The following compound was prepared in a similar manner:

EXAMPLE 54

4-(4-(3-N,N-Dimethylaminopropoxy)phenyl)-N-(3,4,5-trimethoxyphenyl)-2-pyrimidineamine from the compound of Example 49 (250 mg, 0.71 mmol), N,N-dimethylaminopropanol (88 mg, 0.85 mmol), triphenylphosphine (223 mg, 0.85 mmol) and diethylazodicarboxylate (148 mg, 0.85 mmol) to give the title compound (20 mg) as a white solid m.p. 161–164°. MS m/z 439 $(M+H)^+$.

EXAMPLE 55

4-(3-(3-Hydroxypropylamino)phenyl)-N-(3,4,5-trimethoxyphenyl)-2-pyrimidineamine

The compound of Example 40 (250 mg, 0.71 mmol) and 3-bromopropanol were heated at 85° in DMF for 72 h. The solvent was removed under reduced pressure and the residue subjected to column chromatography [silica-ethyl acetate] to give the title compound (33 mg) as a yellow solid m.p. 92–95°. MS m/z 411 $(M+H)^+$.

The following compound was prepared in a similar manner:

EXAMPLE 56

4-(4-(3-Hydroxypropylamino)phenyl)-N-(3,4,5-trimethoxyphenyl)-2-pyrimidineamine from the compound of Example 39 (750 mg, 2.13 mmol) and 3-bromopropanol (3.55 mg, 2.56 mmol) to give the title compound (24 mg) as a yellow solid m.p. 86–90°. MS m/z 411 $(M+H)^+$.

EXAMPLE 57

4-(3-(3-Pyridylmethyl)aminophenyl)-N-(3,4,5-trimethoxyphenyl)-2-pyrimidineamine To a solution of the compound of Example 40 (250 mg, 0.71 mmol) in $CH_2Cl_2$ (20 ml) was added 3-pyridinecarboxaldehyde (69 mg, 0.65 mmol), sodium triacetoxyborohydride (226 mg, 1.07 mmol) and acetic acid (0.1 ml), and the resulting mixture stirred at ambient temperature for 48 h. The reaction was washed with water (2×100 ml), dried ($MgSO_4$), concentrated under reduced pressure, and the residue columned [silica-ethyl acetate] to give the title compound (100 mg) as a yellow solid m.p. 78–80°. MS m/z 444 $(M+H)^+$.

The following compound was prepared in a similar manner:

EXAMPLE 58

4-(4-(3-Pyridylmethyl)aminophenyl)-N-(3,4,5-trimethoxphenyl)-2-pyrimidineamine from the compound of Example 39 (250 mg, 0.71 mmol), 3-pyridinecarboxaldehyde (69 mg, 0.65 mmol), sodium triacetoxyborohydride (226 mg, 1.67 mmol) and acetic acid (0.1 ml) to give the title compound (134 mg) as a yellow solid m.p. 189–190°. MS m/z 444 $(M+H)^+$.

EXAMPLE 59

4-(4-(Aminomethyl)phenyl)-N-(3,4,5-trimethoxyphenyl)-2-pyrimidineamine

To a suspension of $LiAlH_4$ (628 mg, 16.56 mmol) in dry THF (100 ml) at 0° was added dropwise a solution of the compound of Example 27 in THF (10 ml) and when addition was complete the reaction was heated at reflux for 3 h. On cooling a saturated solution of aqueous ammonium chloride (25 ml) was added and the organic solvent removed under reduced pressure. The aqueous solution was extracted with ethyl acetate (2×200 ml) and the combined organic layers dried ($MgSO_4$) followed by evaporation under reduced pressure. The residue was subjected to column chromatography [silica-ethyl acetate] to give the title compound (330 mg) as a yellow solid m.p. 143–144°. MS m/z 367 $(M+H)^+$.

EXAMPLE 60

4-(4-(1H-1,2,3,4-Tetrazol-5-yl)phenyl)-N-(3,4,5-trimethoxyphenyl)-2-pyrimidineamine To a solution of the compound of Example 27 (500 mg, 1.38 mmol) in DMF (15 ml) was added sodium azide (897 mg, 13.8 mmol) and ammonium chloride (738 mg, 13.8 mmol) and the mixture heated at 130° for 18 h. On cooling, water (45 ml) was added, the resulting precipitate collected and recrystallised from ethyl acetate to give the title compound (333 mg) as a yellow solid m.p. 246–247°. δH 9.60 (1H, br s), 8.59 (1H, d, J 5.0 Hz), 8.39 (2H, d, J 8.4), 8.19 (2H, d, J 8.4 Hz), . 7.47 (1H, d, J 5.3 Hz), 7.31 (2H, s), 3.80 (6H, s) and 3.62 (3H, s). MS m/z 406.2 $(M+H)^+$.

EXAMPLE 61

4-(1-Oxopyrid-4-yl)-N-(3,4,5-trimethoxyphenyl)-2-pyrimidineamine

In a manner analogous to the preparation of the compound of Example 1, from 3,4,5-trimethoxyphenylguanidine nitrate (2.25 g, 7.81 mmol), 3-dimethylamino-1-(1-oxopyrid-4-yl)-2-propen-1-one (880 mg, 7.81 mmol) and sodium hydroxide (344 mg, 8.6 mmol) to give the title compound (1.2 g) as a green solid m.p. 220°. MS m/z 355 (M+H). The 3-dimethylamino-1-(1-oxopyrid-4-yl)-2-propen-1-one used as starting material was prepared by heating a solution of 4-acetylpyridine-N-oxide (2.5 g, 18.2 mmol) in dimethylformamide diethylacetal (30 ml) at reflux for 0.5 h. On cooling the resulting solid was collected and washed with diethyl ether to give the desired product (3.18 g) as an orange solid m.p. 181°. The 4-acetylpyridine-N-oxide was prepared by treating a solution of 4-acetylpyridine (3.0 g, 24.8 mmol) in $CH_2Cl_2$ with 3-chloro-peroxybenzoic acid [Aldrich 57–86%] (8.4 g) at room temperature for 12 h. The reaction was filtered, the filtrate concentrated under reduced pressure and the resulting residue subjected to column chromatography [silica 10% methanol-ethyl acetate] to give the desired product (3.2 g) as a white solid m.p. 101°.

EXAMPLE 62

4-(4-(Hydroxymethyl)phenyl)-N-(3,4,5-trimethoxyphenyl)-2-pyrimidineamine

To a suspension of $LiAlH_4$ (560 mg, 14.64 mmol) in dry THF (50 ml) at 0° was added dropwise to a solution of the compound of Example 28 in THF (100 ml) and the reaction heated at reflux for 18 h. On cooling an aqueous saturated solution of ammonium chloride (70 ml) was added and the organic solvent removed under reduced pressure. The aqueous solution was extracted with $CH_2Cl_2$ (300 ml), and this was dried ($MgSO_4$) and evaporated under reduced pressure. The residue was subjected to column chromatography [silica-ethyl acetate] to give title compound (212 mg) as a pale yellow solid m.p. 171–172°. MS m/z 368 $(M+H)^+$.

EXAMPLE 63

4-(2-(3-Hydroxypropylamino)pyridin-5-yl)-N-(3,4,5-trimethoxyphenyl)-2-pyrimidineamine The compound of Example 35 (200 mg, 0.54 mmol) and 3-amino-1-propanol (1.0 ml, 13.05 mmol) were heated at 100° for 3.5 h. On cooling the reaction was concentrated under reduced pressure, water (15 ml) added and the resulting precipitate collected. After washing with water, drying under vacuum and recrystallisaiton from ethanol the title compound (105 mg) was obtained as a yellow solid m.p. 168–160°. δH ($d^6$ DMSO) 9.40 (1H, s), 8.83 (1H, s), 8.38 (1H, d, J 5.3 Hz), 8.12 (1H, br dm, J 7.0 Hz), 7.26 (2H, s), 7.22 (1H, d, J 5.2 Hz), 7.16 (1H, br t, J 3.0 Hz), 6.54 (1H, d, J 8.8 Hz), 4.53 (1H, t, J 5.0 Hz), 3.76 (6H, s), 3.60 (3H, s), 3.47 (2H, q, J 5.4 Hz), 3.32 (2H, m) and 1.68 (2H, m). MS m/z 412 $(M+H)^+$.

The compounds of Examples 64–87 were prepared in a similar manner to the compound of Example 63 using the compound of Example 35 and the amine shown:

EXAMPLE 64

4-(2-(2-Aminoethylamino)pyridin-5-yl)-N-(3,4,5-trimethoxyphenyl)-2-pyrimidineamine from the compound of Example 35 (200 mg, 0.54 mmol) and ethylenediamine (1 ml, 14.96 mmol) to give the title compound (105 mg) as a yellow solid m.p. 117–118° δH ($d^6$ DMSO) 9.35 (1H, s), 8.83 (1H, d, J 2.2 Hz), 8.38 (1H, d, J 5.3 Hz), 8.13 (1H, dd, J 8.9, 2.4 Hz), 7.27 (2H, s), 7.22 (1H, d, J 5.3 Hz), 7.11 (1H, br t, J 5.0 Hz), 3.77 (6H, s), 3.62 (3H, s), 3.29 (2H, q, J 6.3 Hz), 2.71 (2H, t, J 6.3 Hz) and 1.60 (2H, br s). MS m/z 397 (M+H).

EXAMPLE 65

4-(2-(2-Hydroxyethylamino)pyridin-5-yl)-N-(3,4,5-trimethoxyphenyl)-2-pyrimidineamine from the compound of Example 35 (300 mg, 0.81 mmol) and ethanolamine (1.0 ml, 16.56 mmol) to give the title compound (190mg) as an off-white solid m.p. 123°. δH (d$^6$ DMSO) 9.35 (1H, s), 8.82 (1H, d, J 2.2 Hz), 8.38 (1H, d, J 5.3 Hz), 8.12 (1H, dd, J 8.8, 2.4 Hz), 7.26 (2H, s), 7.22 (1H, d, J 6.3 Hz), 7.11 (1H, br t, J 5.0 Hz), 6.59 (1H, d, J 8.8 Hz), 4.73 (1H, br s), 3.77 (6H, s), 3.62 (3H, s), 3.57–3.52 (2H, m) and 3.45–3.38 (2H, m). MS m/z 398 (M+H)$^+$.

EXAMPLE 66

4-(2-(3-Aminopropylamino)pyridin-5-yl)-N-(3,4,5-trimethoxyphenyl)-2-pyrimidineamine from the compound of Example 35(250 mg, 0.68 mmol) and 1,3-diaminopropane (1.0 ml, 11.89 mmol) to give the title compound (120 mg) as a yellow solid m.p. 152–153°. δH (d$^6$ DMSO) 9.34 (1H, s), 8.83–(1H, d, J 2.2 Hz), 8.37 (1H, d, J 5.3 Hz), 8.12 (1H, dd J 8.8, 2.4 Hz), 7.26 (2H, s), 7.21 (1H, d, J 5.3 Hz), 7.14 (1H, bt, J 5.5 Hz), 6.53 (1H, d, J 8.8 Hz), 3.77 (6H, s), 3.62 (3H, s), 3.34 (2H, q, J 7.0 Hz), 2.61 (2H, t, J 6.7 Hz), 2.40 (2H, br s) and 1.65–1.56 (2H, m). MS m/z 411 (M+H)$^+$.

EXAMPLE 67

4-(2-(2-Dimethylaminoethylamino)pyridin-5-yl)-N-(3,4,5-trimethoxyphenyl)-2-pyrimidineamine from the compound of Example 35 (250 mg, 0.68 mmol) and N,N-dimethylethylenediamine (0.75 mol, 14.17 mmol) to give the title compound (85 mg) as an off-white solid m.p. 110–111°. MS m/z 425.5 (M+H)$^+$.

EXAMPLE 68

4-(2-(4-Hydroxybutylamino)pyridin-5-yl)-N-(3,4,5-trimethoxyphenyl)-2-pyrimidineamine from the compound of Example 35 (250 mg, 0.68 mmol) and 4-amino-1-butanol (0.750 mg, 8.43 mmol) to give the title compound (255 mg) as a yellow solid m.p. 170–171°. MS m/z 4216 (M+H)$^+$.

EXAMPLE 69

4-(2-(2-(Pyrrolidin-1-yl)ethylamino)pyridin-5-yl)-N-(3,4,5-trimethoxyphenyl)-2-pyrimidineamine from the compound of Example 35 (250 mg, 0.68 mmol) and N-(2-aminoethyl)pyrrolidine (0.75 ml, 7.31 mmol) to give the title compound (191 mg) as a yellow solid m.p. 165–166°. MS m/z 451 (M+H)$^+$.

EXAMPLE 70

4-(2-(2-Methylamino)ethyl(methyl)amino)pyridin-5-yl)-N-(3,4,5-trimethoxyphenyl)-2-pyrimidineamine from the compound of Example 35 (300 mg, 0.81 mmol) and N,N'-dimethylethylenediamine (0.61 ml, 5.68 mmol) to give the title compound (60 mg) as a buff solid m.p. 115–116°. MS m/z 425 (M+H).

EXAMPLE 71

4-(2-(3-Isopropylaminopropylamino)pyridin-5-yl)-N-(3,4,5-trimethoxyphenyl)-2-pyrimidineamine from the compound of Example 35 (300 mg, 0.81 mmol) and N-isopropyl-1,3-propanediamine (0.51 ml, 4.0 mmol) to give the title compound (208 mg) as a pale yellow solid m.p. 124–125°. MS m/z 453 (M+H)$^+$.

EXAMPLE 72

4-(2-(1-Benzylpiperid-4-ylamino)pyridin-5-yl)-N-(3,4,5-trimethoxyphenyl)-2-pyrimidineamine from the compound of Example 35 (500 mg, 1.35 mmol) and 4-amino-1-benzylpiperidine (514 mg, 2.7 mmol) to give the title compound (370 mg) as a yellow solid m.p. 113–114°. MS m/z 527 (M+H)$^+$.

EXAMPLE 73

4-(2-(3-(Morpholino)propylamino)pyridin-5-yl)-N-(3,4,5-trimethoxyphenyl)-2-pyrimidineamine from the compound of Example 35 (300 mg, 0.81 mmol) and 3-(aminopropyl)morpholine (0.59 ml, 4 mmol) to give the title compound (300 mg) as a white solid m.p. 165–166°. MS m/z 481 (M+H)$^+$.

EXAMPLE 74

4-(2-(4-Methoxyphenylamino)pyridin-5-yl)-N-(3,4,5-trimethoxyphenyl)-2-pyrimidineamine from the compound of Example 35 (300 mg, 0.81 mmol) and para-anisidine (200 mg, 1.62 mmol) to give the title compound (170 mg) as a yellow solid m.p. 209–210°. MS m/z 459 (M+H)$^+$.

EXAMPLE 75

4-(2-(3-Methylaminopropyl(methyl)amino)pyridin-5-yl)-N-(3,4,5-trimethoxyphenyl)-2-pyrimidineamine In a manner analogous to Example 63 from the compound of Example 35 (500 mg) and N,N'-dimethyl-1,3-propanediamine (1.62 ml, 13.0 mmol) to give the title compound (31 mg) as a yellow solid. m.p. °. MS m/z 439 (M+H)$^+$.

EXAMPLE 76

4-(2-(2-Hydroxycyclohexylamino)pyridin-5-yl)-N-(3,4,5-trimethoxyphenyl)-2-pyrimidineamine from the compound of Example 35 (300 mg, 0.81 mmol), trans-2-aminocyclohexanol hydrochloride (614 mg, 4.05 mmol) and triethylamine (0.56 ml, 4.05 mmol) to give the title compound (147 mg) as a yellow solid m.p. 147–148°. MS m/z 452 (M+H).

EXAMPLE 77

4-(2-(3-Dimethylamino-2,2-dimethylpropylamino)pyridin-5-yl)-N-(3,4,5-trimethoxyphenyl)-2-pyrimidineamine from the compound of Example 35 (300 mg, 0.81 mmol) and N,N,2,2-tetramethyl-1,3-propanediamine (527 mg, 4.05 mmol) to give the title compound (147 mg) as a white solid m.p. 125°. MS m/z 467 (M+H)$^+$.

EXAMPLE 78

4-(2-(3-Dimethylaminopropylamino)pyridin-5-yl)-N-(3,4,5-trimethoxyphenyl)-2-pyrimidine from the compound of Example 35 (300 mg, 0.81 mmol) and 3-dimethylaminopropylamine (248 mg, 2.43 mmol) to give the title compound (201 mg) as a buff solid m.p. 170°. MS m/z 439 (M+H)$^+$.

EXAMPLE 79

4-(2-(2-Diethylaminoethyl(methyl)amino)pyridin-5-yl)-N-(3,4,5-trimethoxyphenyl)-2-pyrimidine from the compound of Example 35 (300 mg, 0.81 mmol) and N,N-diethy-N'-methylethylenediamine (316 mg, 2.43 mmol) to give the title compound (372 mg) as a buff solid m.p. 111°. MS m/z 467 (M+H)$^+$.

EXAMPLE 80

4-(2-(3-Diethylaminopropylamino)pyridin-5-yl)-N-(3,4,5-trimethoxyphenyl)-2-pyrimidineamine from the compound of Example 35 (300 mg, 0.81 mmol) and N,N-diethylaminopropylamine (282 mg, 2.43 mmol) to give the title compound (146 mg) as a yellow solid m.p. 67°. MS m/z 453 (M+H)$^+$.

EXAMPLE 81

4-(2-(2-(1-Methylpyrrolidin-2-yl)ethylamino)pyridin-5-yl)-N-(3,4,5-trimethoxyphenyl)-2-pyrimidineamine from the compound of Example 35 (300 mg, 0.81 mmol) and 2-(2-aminoethyl)-1-methylpyrrolidine (512 mg, 4.0 mmol) to give the title compound (190 mg) as a yellow solid m.p. 176–177°. MS M/z 465 (M+H)$^+$.

EXAMPLE 82

4-(2-(1-(Ethylpyrrolidin-2-yl)methylamino)pyridin-5-yl)-N-(3,4,5-trimethoxy-phenyl)-2-pyrimidineamine from the compound of Example 35 (300 mg), 0.81 mmol) and 2-(aminomethyl)-1-ethylpyrrolidine (5.3 mg, 4.0 mmol) to give the title compound (240 mg) as a yellow solid m.p. 81–82°. MS m/z 465 (M+H)$^+$.

EXAMPLE 83

4-(2-(2-Dimethylaminoethyl(ethyl)amino)pyridin-5-yl)-N-(3,4,5-trimethoxyphenyl)-2-pyrimidineamine.

from the compound of Example 35 (300 mg, 0.81 mmol) and N,N-dimethyl-N'-ethylethylenediamine (282 mg, 2.43 mmol) to give the title compound (193 mg) as a yellow solid, m.p. 90°. MS m/z 453 (M+H)$^+$.

EXAMPLE 84

4-(2-(4-Aminobutylamino)pyridin-5-yl)-N-(3,4,5-trimethoxyphenyl)-2-pyrimidineamine from the compound of Example 35 (300 mg, 0.81 mmol) and 1,4-butanediamine (705 mg, 8.0 mmol) as a yellow solid m.p. 209–201°. δH (d$^6$ DMSO) 9.35 (1H, s), 8.82 (1H, d, J 2.3 Hz), 8.37 (1H, d, J 5.3 Hz), 8.11 (1H, dd, J 8.9, 2.3 Hz), 7.26 (2H, s), 7.21 (1H, d, J 5.3 Hz), 7.15 (1H, br t, NH), 6.53 (1H, d, J 8.9 Hz), 3.77 (6H, s), 3.61 (3H, s), 3.28 (2H, q, J 6.0 Hz), 2.58 (2H, t, J 6.9 Hz), 1.58–1.53 (2H, m) and 1.97–1.39 (2H, m). MS m/z 425 (M+H)$^+$.

EXAMPLE 85

4-(2-(2-Diethylaminoethylamino)pyridin-5-yl)-N-(3,4,5-trimethoxyphenyl)-2-pyrimidineamine from the compound of Example 35 (300 mg, 0.81 mmol) and N,N-diethylethylenediamine (282 mg, 2.43 mmol) to give the title compound (50 mg) as a yellow solid m.p. 67°. MS m/z 453 (M+H)$^+$.

EXAMPLE 86

4-(2-(3-(4-Methylpiperazin-1-yl)propylamino)pyridin-5-yl)-N-(3,4,5-trimethoxyphenyl)-2-pyrimidineamine from the compound of Example 35 (350 mg, 0.94 mmol) and 1-(3-aminopropyl)-4-methylpiperazine (629 mg, 4.0 mmol) to give the title compound (238 mg) as a white solid m.p. 183–184°. MS m/z 494 (M+H)$^+$.

EXAMPLE 87

4-(2-(2-Dimethylaminoethyl(methyl)amino)pyridin-5-yl)-N-(3,4,5-trimethoxyphenyl)pyrimidine-2-amine from the compound of Example 35 (30 mg, 0.81 mmol) and N,N,N'-trimethylethylenediamine (400 mg, 4.0 mmol) to give the title compound (310 g) as a yellow solid m.p. 97–98°. MS m/z 439 (M+H)$^+$.

EXAMPLE 88

4-(2-(Piperid-4-ylamino)pyridin-5-yl)-N-(3,4,5-trimethoxyphenyl)-2-pyrimidineamine acetate To a solution of the compound of Example 72 (90 mg, 0.15 mmol) as the acetate salt in ethanol (10 ml) was added cyclohexadiene (0.095 ml, 1.0 mmol) and 10% palladium on charcoal (100 mg) and the reaction heated at reflux for 1 h. On cooling the reaction was filtered through a pad of Celite® and the filtrate concentrated under reduced pressure to give the title compound (20 mg) as a yellow solid m.p.87–88°. MS m/z 437 (M+H)$^+$.

EXAMPLE 89

N4-Phenyl-N2-(3,4,5-trimethoxyphenyl)-2,4-pyrimidinediamine

A solution of N-phenyl-2-chloro-4-pyrimidineamine (1.83 g, 8.91 mmol) and 3,4,5-trimethoxyaniline (1.83 g, 10.0 mmol) in acetone (10 ml) and water (15 ml) containing concentrated hydrochloric acid (0.2 ml) was heated at reflux for 10 h. On cooling the acetone was removed under reduced pressure, and the reaction taken to pH10 with 4N NaOH and extracted with ethyl acetate (2×75 ml). The combined organic layers were dried (MgSO$_4$), concentrated under reduced pressure and the residue crystallised from ethyl acetate to give the title compound (2.41 g) as a colourless solid m.p. 191°. δH (CDCl$_3$) 8.04 (1H, d, J 5.8 Hz), 7.37–7.34 (4H, m), 7.16–7.10 (1H, m), 7.05 (1H, br s), 6.85 (2H, s), 6.68 (1H, br s), 6.16 (1H, d, J 5.8 Hz), 3.82 (3H, s) and 3.81 (6H, s). MS m/z 353 (M+H)$^+$. The pyrimidineamine used as starting material was prepared by heating a solution of 2,4-dichloropyrimidine (4.0 g, 26.8 mmol), aniline (2.46 ml, 27.0 mmol) and triethylamine (4.3 ml, 30.0 mmol) in ethanol (50 ml) at reflux for 2 h. On cooling a white precipitate was collectd which was washed with cold ethanol (100 ml) and recrystallised from ethyl acetate to give the desired product (6.0 g) as a colourless solid m.p. 186°. MS/mz 206 (M+H)$^+$.

The compounds of Examples 90–110 were prepared in a similar manner to the compound of Example 89 using the starting material shown. In each case the pyrimidineamine starting material was prepared from the available compounds shown in a similar manner to the pyrimidineamine starting material of Example 89:

EXAMPLE 90

N4-(4-(2-Hydroxyethoxy)phenyl)-N2-(3,4,5-trimethoxyphenyl)2,4-pyrimidineamine from 2-chloro-N-(4-(2-hydroxyethoxy)phenyl)-4-pyrimidineamine (187 mg, 0.70 mmol) and 3,4,5-trimethoxyaniline (146 mg, 0.8 mmol) to give the title compound (18 mg) as a colourless solid m.p. 212°. δH (d$^6$ DMSO) 9.09 (1H, br s), 8.89 (1H, br s), 7.94 (1H, d, J 5.8 Hz), 7.53 (2H, d, J 8.6 Hz), 7.10 (2H, s), 6.86 (2H, d, J 8.6 Hz), 6.10 (1H, d, J 5.8 Hz), 4.83 (1H, t, J 5.6 Hz),. 3.95 (2H, t, J 4.9 Hz), 3.71–3.68 (2H, m), 3.65 (6H, s) and 3.60 (3H,s). MS m/z 413 (M+H). The pyrimidineamine starting material was prepared from 4-(2-hydroxyethoxy)aniline (481 mg, 3.14 mmol) 2,4-dichloropyrimidine (468 mg, 3.14 mmol) and triethylamine (0.46 ml, 3.25 mmol) to give the desired product as a yellow solid m.p. 169°. MS m/z 266(M+H)$^+$.

EXAMPLE 91

N4-(3,4-Methylenedioxyphenyl)-N2-(3,4,5-trimethoxyphenyl)-2,4-pyrimidinediamine from 2-chloro-N-(3,4-methylenedioxyphenyl)-4-pyrimidineamine (200 mg, 0.85 mmol) and 3,4,5-trimethoxyaniline (1 56 mg, 0.85 mmol) to give the title compound (187 mg) as a buff solid m.p. 199°. MS m/z 397 (M+H)$^+$. The pyrimidineamine starting material was prepared from 3,4-methylenedioxyaniline (219 mg, 1.60 mmol) 2,4-dichloropyrimidine (250 mg, 1.60 mmol) and triethylamine (0.25 ml, 1.80 mmol) to give the desired product (215 mg) as a buff solid m.p. 148°. MS m/z 250 (M+H)$^+$.

EXAMPLE 92

N4-(3-Methoxyphenyl)-N2-(3,4,5-trimethoxyphenyl)-2,4-pyrimidinediamine from 2-chloro-N4-(3-methoxyphenyl)-4-pyrimidineamine (195 mg, 0.83 mmol) and 3,4,5-trimethoxyaniline (152 mg, 0.83 mmol) to give the title compound (189 mg) as a white solid m.p. 78°. MS m/z 383 ((M+H). The pyrimidineamine starting material was prepared from meta-anisidine (0.18 mg, 1.6 mmol), 2,4-dichloropyrimidine (250 mg, 1.6 mmol) and triethylamine (0.25 mg, 1.8 mmol) to give the desired product (200 mg) as a white solid m.p. 107°. MS m/z 236 (M+H)$^+$.

EXAMPLE 93

N4-(3-(2-Hydroxyethyl)phenyl)-N2-(3,4,5-trimethoxyphenyl)-2,4-pyrimidinediamine from 2-chloro-N-(4-(2-hydroxyethyl)phenyl)-4-pyrimidineamine (250 mg, 1.0 mmol) and 3,4,5-trimethoxyaniline (184 mg, 1.0 mmol) to give the title compound (257 mg) as a white solid m.p. 72°. MS m/z 397 (M+H). The pyrimidineamine starting material was prepared from 2-(4-aminophenyl)ethanol (219 mg, 1.6 mmol) 2,4-dichloropyrimidine (250 mg, 1.6 mmol) and triethylamine (0.25 ml, 1.8 mmol) to give the desired product (289 mg) as an orange solid m.p. 163°.

EXAMPLE 94

N4-(4-(Diethylamino)phenyl)-N2-(3,4,5-trimethoxyphenyl)-2,4-pyrimidinediamine from 2-chloro-N-(4-(diethylamino)phenyl)-4-pyrimidineamine (250 mg, 0.9 mmol) and 3,4,5-trimethoxyaniline (166 mg, 0.9 mmol) to give the title compound (80 mg) as a green solid m.p. 87°. MS m/z 424.5 (M+H)$^+$. The pyrimidineamine starting material was prepared from N,N-diethyl-1,4-phenyldiamine (263 mg, 1.6 mmol), 2,4-dichloropyrimidine (250 mg, 1.6 mmol) and triethylamine (0.25 ml, 1.8 mmol) to give the desired prdocut (410 mg) as a green solid m.p. 212°. MS m/z 277 (M+H)$^+$.

EXAMPLE 95

N4-(4-(3-Hydroxypropoxy)phenyl)-N2-(3,4,5-trimethoxyphenyl)-2,4-pyrimidinediamine from 2-chloro-N-(4-(3-hydroxypropoxy)phenyl)-4-pyrimidineamine (250 mg, 0.89 mmol) and trimethoxyaniline (164 mg, 0.89 mmol) to give the title compound (61 mg) as a white solid m.p. 69°. MS m/z 427 (M+H)$^+$. The pyrimidineamine starting material was prepared (from 4-(3-hydroxypropoxy)aniline (267 mg, 1.60 mmol), 2,4-dichloropyrimidine (250 mg, 1.60 mmol) and triethylamine (0.25 ml, 1.80 mmol) to give the desired product (383 mg) as a pale orange solid m.p. 181°. MS m/z 280 (M+H)$^+$.

EXAMPLE 96

N4-(3,4-Dimethoxyphenyl)-N2-(3,4,5-trimethoxyphenyl)-2,4-pyrimidinediamine from 2-chloro-N-(3,4-dimethoxyphenyl)-4-pyrimidineamine (250 mg) and 3,4,5-trimethoxyaniline (189 mg, 1.0 mmol) to give the title compound (160 mg) as a light pink solid m.p. 86°. MS m/z 413 (M+H)$^+$. The pyrimidineamine starting material was prepared from aminoveratrole (257 mg, 1.60 mmol), 2,4-dichloropyrimidine (2.50 mg, 1.60 mmol) and triethylamine (0.25 ml, 1.80 mmol) to give the desired product (357 mg) as a purple solid m.p. 104° MS m/z 266 (M+H)$^+$.

EXAMPLE 97

N4-(4-(4-Methylpiperazin-1-yl)phenyl)-N2-(3,4,5-trimethoxyphenyl)-2,4-pyrimidinediamine from 2-chloro-N-(4-(4-methylpiperazin-1-yl)phenyl)-4-pyrimidineamine (110 mg, 0.40 mmol) and 3,4,5-trimethoxyaniline (66 mg, 0.40 mmol) to give the title compound (80 mg) as a white solid m.p. 104°. MS m/z 451 (M+H)$^+$. The pyrimidineamine starting material was prepared from 4-(4-methylpiperazin-1-yl)aniline (511 mg, 2.67 mmol), 2,4-dichloropyrimidine (398 mg, 2.67 mmol) and triethylamine (10.4 ml, 2.94 mmol) to give the desired product (110 mg) as a white solid m.p. 122°.

EXAMPLE 98

N4-(3,5-Dimethoxyphenyl)-N2-(3,4,5-trimethoxyphenyl)-2,4-pyrimidinediamine from 2-chloro-N-(3,5-dimethoxyphenyl)-4-pyrimidineamine (150 mg, 0.56 mmol) and 3,4,5- trimethoxyaniline (104 mg, 0.56 mmol) to give the title compound (162 mg) as a white solid m.p. 180°. MS m/z 413 (M+H)⁺. The pyrimidineamine starting material was prepared from 3,5-dimethoxyaniline (257 mg, 1.60 mmol), 2,4-dichloropyrimidine (250 mg, 1.60 mmol) and triethylamine (0.25 ml, 1.80 mmol) to give the desired product (237 mg) as a white solid m.p. 225°. MS m/z 266 (M+H)⁺.

EXAMPLE 99

N4-(4-Morpholinophenyl)-N2-(3,4,5-trimethoxyphenyl)-2,4-pyrimidinediamine from 2-chloro-N-(4-morpholinophenyl)-4-pyrimidineamine (300 mg, 1.03 mmol) and 3,4,5-trimethoxyaniline (1 89 mg, 1.03 mmol) to give the title compound (230 mg) as a white solid m.p. 214°. MS m/z 438 (M+H)⁺. The pyrimidineamine starting material was prepared from 4-morpholinoaniline (285 mg, 1.60 mmol), 2,4-dichloropyrimidine (205 mg, 1.60 mmol) and triethylamine (0.25 ml, 1.80 mmol) to give the desired product (322 mg) as a white solid m.p. 221°. MS m/z 291 (M+H)⁺.

EXAMPLE 100

N4-(3-Trifluoromethoxyphenyl)-N2-(3,4,5-trimethoxyphenyl)-2,4-pyrimidinediamine from 2-chloro-N-(3-trifluoromethoxyphenyl)-4-pyrimidineamine (230 mg, 0.79 mmol) and 3,4,5-trimethoxyaniline (145 mg, 0.79 mmol) to give the title compound (220 mg) as a white solid m.p. 154–156°. MS m/z 437 (M+H)⁺. The pyrimidineamine starting material was prepared from 3-trifluoromethoxyaniline (354 mg, 2.0 mmol) 2,4-dichloropyrimidine (218 mg, 2.0 mmol) and triethylamine (0.3 ml, 2.20 mmol) to give the desired product (240 mg) as a white solid m.p. 161–163°. MS m/z 290 (M+H)⁺.

EXAMPLE 101

N4-(2-Methylbenzimidazol-5-yl)-N2-(3,4,5-trimethoxyphenylamino)-2,4-pyrimidinediamine from 2-chloro-N-(2-methylbenzimidazol-5-yl)-4-pyrimidineamine (250 mg, 0.96 mmol) and 3,4,5-trimethoxyaniline (176 mg, 0.96 mmol) to give the title compound (36 mg) as a white solid m.p. 179°. MS m/z 407 (M+H). The pyrimidineamine starting material was prepared from 5-amino-2-methylbenzimidazole (2147 mg, 1.68 mmol), 2,4-dichloropyrimidine (250 mg, 1.68 mmol) and triethylamine (0.25 ml, 1.80 mmol) to give the desired product (344 mg) as a pale pink solid m.p. >300°. MS m/z 260 (M+H)⁺.

EXAMPLE 102

N4-(4-(Dimethylamino)phenyl)-N2-(3,4,5-trimethoxyphenylamino)-2,4-pyrimidinediamine from 2-chloro-N-(4-(dimethylamino)phenyl)-4-pyrimidineamine (250 mg, 1.0 mmol) and 2,3,4-trimethoxyaniline (184 mg, 1.0 mmol) to give the title compound (127 mg) as a grey solid m.p. 215°. MS m/z 396 (M+H)⁺. The pyrimidineamine starting material was prepared from N,N-dimethyl-1,4-phenylenediamine (228 mg, 1.68 mmol) 2,4-dichloroprimidine (250 mg, 1.68mol) and triethylamine (0.25 ml, 1.80 mmol) to give the desired product (402 mg) as a white solid m.p. 212°.

EXAMPLE 103

N4-(4-(Ethoxycarbonylmethyl)phenyl)-N2-(3,4,5-trimethoxyphenyl)-2,4-pyrimidinediamine from 2-chloro-N-(4-ethoxycarbonylmethyl)phenyl)-4-pyrimidineamine (1.74 g, 5.97 mmol) and 3,4,5-trimethoxyphenylaniline (1.09 g, 5.97 mmol) to give the title compound (1.0 g) as a white solid m.p. 143–144°. δH (CDCl₃) 8.04 (1H, d, J 5.8 Hz), 7.32 (2H, d, J 8.6 Hz), 7.26 (2H, d, J 8.6 Hz), 7.01 (1H, br s), 6.86 (2H, s), 6.64 (1H, br s), 6.15 (1H, d, J 5.8 Hz), 4.17 (2H, q, J 7.1 Hz), 3.82 (3H, s), 3.81 (6H, s), 3.60 (2H, s) and 1.27 (3H, t, J 7.1 Hz). MS m/z 439 (M+H)⁺. The pyrimidineamine starting material was prepared from ethyl 4-aminophenylacetate (1.79 g, 10.0 mmol) 2,4-dichloropyrimidine (1.49 g, 10.0 mmol) and triethylamine (2.8 ml, 20 mmol) to give the desired product (2.88 g) as a white solid, m.p. 151–152°.

EXAMPLE 104

N4-(4-Benzyloxyphenyl)-N2-(3,4,5-trimethoxyphenyl)-2,4-pyrimidinediamine from N-(4-benzyloxyphenyl)-2-chloro-4-pyrimidineamine (25.0 g, 80.0 mmol) and 3,4,5-trimethoxyaniline (14.7 g, 80.0 mmol) to give the title compound (18.6 g) as a white solid m.p. 161–164°. MS m/z 459 (M+H)⁺. The pyrimidineamine starting material was prepared from 4-benzyloxyaniline (20.0 g, 0.1mol), 2,4-dichloropyrimidine (15.0 g, 0.1mol) and triethylamine (15.0 ml, 0.11mol) to give the desired product (30.0 g) as a cream solid m.p. 198°. MS m/z 312 (M+H)⁺.

EXAMPLE 105

N4-(3-Ethoxyphenyl)-N2-(3,4,5-triemthoxyphenyl)-2,4-pyrimidinediamine from 2-chloro-N-(3-ethoxyphenyl)-4-pyrimidineamine (125 mg, 0.5 mmol) and 3,4,5-trimethoxyaniline (92 mg, 0.5 mmol) to give the title compound (157 mg) as a white solid m.p. 79°. MS m/z 397 (M+H). The pyrimidineamine starting material was prepared from metaphenetidine (0.15 ml, 1.68 mmol), 2,4-dichloropyrimidine (250 mg, 1.68 mmol) and triethylamine (0.25 ml, 1.80 mmol) to give the desired product (125 mg) as a cream solid m.p. 97°.

EXAMPLE 106

N4-(4-Benzyloxycarbonylmethylphenyl)-N2-(3,4,5-trimethoxyphenyl)-2,4-pyrimidinediamine from N-(4-(benzyloxy-carbonylmethyl)phenyl)-2-chloro-4-pyrimidineamine (3.14 g, 8.90 mmol) and 3,4,5-trimethoxyaniline (1.63 g, 8.90 mmol) to give the title compound (3,47 g) as a white solid m.p. 141–143°. δH (CDCl₃) 8.04 (1H, d, J 5.8 Hz), 7.36–7.24 (9H, m), 7.15 (1H, br s), 6.86 (2H, s), 6.74 (1H, br s), 6.15 (1H, d, J 5.8 Hz), 5.15 (2H, s), 3.82 (3H, s), 3.81 (6H, s) and 3.66 (2H, s). MS m/z 501 (M+H)⁺. The pyrimidineamine starting material was prepared from benzyl 4-aminophenylacetate (4.82 g, 20.0 mmol), 2,4-dichloropyrimidine (2.98 g, 20.0 mmol) and triethylamine (5.60 ml, 40.0 mmol) to give the desired product (3.24 g) as a white solid m.p. 149°. MS m/z 354 (M+H)⁺.

EXAMPLE 107

N4-(4-Methoxyphenyl)-N2-(3,4,5-trimethoxyphenyl)-2,4-pyrimidinediamine from 2-chloro-N-(4-methoxyphenyl)-4-pyrimidineamine (315 mg, 1.30 mmol) and 3,4,5-trimethoxyaniline (270 mg, 1.50 mmol) to give the title compound (470 mg) as a white solid m.p.210°. MS m/z 383 (M+H)⁺. The pyrimidineamine starting material was prepared from para-anisidine (616 mg, 5.0 mmol), 2,4-dichloropyrimidine (745 mg, 5.0 mmol) and triethylamine (0.77 ml, 5.5 mmol) to give the desired compound (450 mg) as a white solid m.p. 250°.

EXAMPLE 108

N4-(3-Benzyloxyphenyl)-N2-(3,4,5-trimethoxyphenyl)-2,4-pyrimidineamine from N-(3-benzyloxyphenyl)-2-chloro-4-pyrimidineamine (2.0 g, 6.4 mmol) and 3,4,5-trimethoxyaniline (1.18 g, 6.4 mmol) to give the title compound (2.60 g) as a white solid m.p. 186°. MS m/z 459 (M+H)$^+$. The pyrimidineamine starting material was prepared from 3-benzyloxyaniline (5.0 g, 25.0 mmol), 2,4-dichloropyrimidine (3.7 g, 25.0 mmol) and triethylamine (3.8 ml, 27.5 mmol) to give the desired compound (4.95 g) as a white solid m.p. 119°. MS m/z 312 (M+H)$^+$.

EXAMPLE 109

N4-(1-Phenylsulphonylindol-5-yl)-N2-(3,4,5-trimethoxyphenyl)-2,4-pyrimidinediamine from 2-chloro-N-(1-phenylsulphonylindol-5-yl)-4-pyrimidineamine (1.09 g, 2.70 mmol) and 3,4,5-trimethoxyaniline (496 mg, 2.70 mmol) to give the title compound (950 mg) as a white solid m.p. 127°. MS m/z 532 (M+H)$^+$. The pyrimidineamine starting material was prepared from 5-amino-1-phenylsulphonylindole (1.0 g, 3.9 mmol), 2,4-dichloropyrimidine (577 mg, 3.9 mmol) and triethylamine (0.61 ml) to give the desired product (1.20 g) as an orange solid m.p. 158°. MS m/z 385 (M+H)$^+$.

EXAMPLE 110

N4-Cyclohexyl-N2-(3,4,5-trimethoxyphenyl)-2,4-pyrimidinediamine from 2-chloro-N-cyclohexylamino-4-pyrimidineamine (200 mg, 0.9 mmol) and 3,4,5-trimethoxyaniline (173 mg, 0.9 mmol) to give the title compound (173 mg) as a white solid m.p. 160–161°. δH (CDCl$_3$) 7.91 (1H, d, J 5.9 Hz), 6.90 (1H, s), 6.87 (2H, s), 5.81 (1H, d, J 5.9 Hz), 4.63 (1H, br s), 3.86 (6H, s), 3.81 (3H, s), 2.00 (2H, m), 1.70 (4H, m) and 1.25 (4H, m). MS m/z 359 (M+H)$^+$. The pyrimidineamine starting material was prepared from cyclohexylamine (0.4 ml, 3.4 mmol), 2,4-dichloropyrimidine (500 mg, 3.4 mmol) and triethylamine (0.5 ml, 3.7 mmol) to give the desired product (270 mg) as a white solid m.p. 128°. MS m/z 212 (M+H)$^+$.

EXAMPLE 111

N4-(1-Benzylpiperid-4-yl)-N2-(3,4,5-trimethoxyphenyl)-2,4-pyrimidinediamine from N-(1-benzylpiperid-4-yl)-2-chloro-4-pyrimidineamine (390 mg, 1.3 mmol) and 3,4,5-trimethoxyaniline (236 mg, 1.3 mmol) to give the title compound (126 mg) as a white solid m.p. 147°. δH (CDCl$_3$) 7.90 (1H, d, J 5.8 Hz), 7.28 (5H, m), 6.94 (1H, s), 6.86 (2H, s), 5.81 (1H, d, J 5.8 Hz), 4.62 (1H, br s), 3.85 (6H, s), 3.81 (3H, s), 3.53 (2H, s), 2.83 (2H, m), 2.16 (2H, m), 2.01 (2H, m) and 1.52 (2H, m). The pyrimidineamine starting material was prepared from 4-amino-1-benzylpiperidine (0.7 ml, 3.4 mmol), 2,4-dichloropyrimidine (500 mg, 3.4 mmol) and triethylamine (0.5 ml, 3.7 mmol) to give the desired product (650 mg) as a white solid m.p. 136°. MS m/z 303 (M+H)$^+$.

EXAMPLE 112

N4-Benzyl-N2-(3,4,5-trimethoxyphenyl)-2,4-pyrimidinediamine from N-benzyl-2-chloro-4-pyrimidineamine (1.5 g, 6.83 mmol) and 3,4,5-trimethoxyaniline (1.31 g, 7.17 mmol) to give the title compound (2.30 g) as a white solid m.p. 167–168°. MS m/z 367 (M+H)$^+$. The pyrimidineanine starting material was prepared from benzylamine (3.67 ml, 33.56 mmol), 2,4-dichloropyrimidine (5.0 g, 33.56 mmol) and triethylamine (5.14 ml, 36.9 mmol) to give the desired product (4.21 g) as a white solid. m.p. 135–136°. MS m/z 220 (M+H)$^+$.

EXAMPLE 113

N2-(3,4-Dimethoxy-5-(methylthio)phenyl)-N4-(3-methoxyphenyl)-2,4-pyrimidinediamine from 2-chloro-N-(3-methoxy-phenyl)-4-pyrimidineamine (0.59 g, 2.51 mmol) [see Example 92] and 3,4-dimethoxy-5-(methylthio)aniline (0.50 g, 2.51 mmol) to give the title compound (0.91 g) as a white solid m.p. 68–70°. δH (CDCl$_3$) 8.02 (1H, d, J 5.8 Hz), 7.40 (1H, br, s), 7.26 (1H, m), 7.08 (1H, d, J 2.2 Hz), 6.90 (4H, m), 6.68 (1H, dd, J 8.2, 2.2 Hz), 6.20 (1H, d, J 5.8 Hz), 3.82 (3H, s), 3.79 (3H, s), 3.77 (3H, s) and 2.35 (3H, s), MS m/z 399 (M+H)$^+$. The aniline starting material was prepared by treating a solution of 1,2-dimethoxy-3-(methylsulphinyl)-5-nitrobenzene (1.64 g, 6.69 mmol) in methanol (20 ml) and concentrated hydrochloric acid (20 ml) was treated with anhydrous tin (II) chloride (7.15 g, 37.7 mmol) and the resulting mixture refluxed for 1.25 h. On cooling to room temperature the mixture was poured into excess 1M NaOH solution and extracted with CH$_2$Cl$_2$. The organic extract was dried (MgSO$_4$) and evaporated to afford the desired product (1.33 g) as an off-white solid m.p. 106–107°. MS m/z 199 (M+H)$^+$.

EXAMPLE 114

N2-(3,4-Dimethoxy-5-methylphenyl)-N4-(3-methoxyphenyl)-2,4-pyrimidinediamine from 2-chloro-N-(3-methoxyphenyl)-4-pyrimidineamine (1.93 g) [see Example 92] and 3,4-dimethoxy-5-methylaniline (1.50 g) to give the title compound (2.53 g) as a pale pink solid m.p. 66–68°. δH (CDCl$_3$) 8.02 (1H, d, J 5.8 Hz), 7.39 (1H, br s), 7.23 (1H, t, J 8.1 Hz), 7.08 (1H, m), 7.05 (1H, br s), 6.97–6.91 (2H, m), 6.86 (1H, d, J 2.0 Hz), 6.69–6.65 (1H, m), 6.18 (1H, d, J 5.8 Hz), 3.77 (3H, s), 3.75 (6H, s) and 2.22 (3H, s). MS m/z 367 (M+H)$^+$. The aniline used as starting material was prepared according to the methods of I Sanchez et al: Tetrahedron 41, 2355 (1985).

EXAMPLE 115

N2-(3,4-Dimethoxyphenyl)-N4-(3-methoxyphenyl)-2,4-pyrimidinediamine from 2-chloro-N-(3-methoxyphenyl)-4-pyrimidineamine (0.77 g, 3.27 mmol) [see Example 92] and 3,4-dimethoxyaniline (0.50 g, 3.27 mmol) to give the title compound (0.89 g) as a beige solid m.p. 135–138°. δH (CDCl$_3$) 8.03 (1H, d, J 5.8 Hz), 7.22 (2H, m), 7.13 (1H, br s), 7.02 (1 H. dd, J 8.6, 2.3 Hz), 6.97 (1H, m), 6.92 (1H, m), 6.82 (1H, d, J 87.6 Hz), 6.77 (1H, br s), 6.68 (1H, dd, J 8.2, 2.3 Hz), 6.18 (1H, d, J 5.8 Hz), 3.86 (3H, s), 3.83 (3H, s) and 3.77 (3H, s). MS m/z 353 (M+H)$^+$.

EXAMPLE 116

N2-(3-Chloro-4.5-dimethoxyphenyl)-N4-(3-methoxyphenyl)-2,4-pyrimidinediamine hydrochloride from 2-chloro-N-(3-methoxyphenyl)-4-pyrimidineamine (0.50 g, 2.13 mmol) [see Example 92] and 3-chloro-4,5- dimethoxyaniline (0.40 g, 2.13 mmol) to give the title compound (0.55 g) as a white soid m.p. 204–205°. δH (d⁶ DMSO) 11.19 (1H, br s),10.85 (1H, brs), 8.00 (1H, d, J 7.1 Hz), 7.23 (4H, m), 7.12 (1H, d, J 4.4 Hz), 6.75 (1H, m), 6.59 (1H, d, J 7.1 Hz), 3.74 (3H, s), 3.69 (3H, s) and 3.65 (3H, s). MS m/z 387 (M+H)⁺. The aniline starting material was prepared in a similar manner to the analogous aniline of Example 113, from 1-chloro-2,3-dimethoxy-5-nitrobenzene (1.08 g, 5.82 mmol), to give the desired product (0.85 g) as a white solid m.p. 66–68°. MS m/z 188 (M+H)⁺. The 1-chloro-2,3-dimethoxy-5-nitrobenzene was prepared by heating a solution of 3-chloro-4,5-dimethoxybenzoic acid (3.50 g, 16.2 mmol) in glacial acetic acid (15 ml) and 70% nitric acid (15 ml) at 600 for 1 h. The reaction was poured onto ice-water and the white precipitate which formed was filtered off, washed with water and dried in vacuo and washed thoroughly with hexane. The hexane washings were evaporated and the residue subjected to column chromatography [silica 20% ethyl acetate-hexane] to give the desired product (1.03 g) as a white solid m.p. 104–105°. MS m/z 217 (M+H)⁺. The acid used as starting material was prepared according to the method of Y. Ohtani et al. Acta. Chem. Scand., Ser B. B36, 613 (1982).

EXAMPLE 117

N2-(3-Benzyloxy-4,5-dimethoxyphenyl)-N4-(3-methoxyphenyl)-2,4-pyrimidinediamine from 2-chloro-N-(3-methoxyphenyl)-4-pyrimidineamine (1 62 mg, 0.69 mmol) [see Example 92] and 3-benzyloxy-4,5-dimethoxyaniline (180 mg, 0.69 mmol) to afford the title compound (255 mg) as an off-white solid m.p. 83–84°. δH (CDCl₃) 8.01 (1H, d, J 5.8 Hz), 7.45–7.22 (6H, m), 6.95 (3H, m), 6.90 (1H, d, J 7.6 Hz), 6.79 (1H, d, J 2.4 Hz), 6.68 (1H, d, J 7.6 Hz), 6.48 (1H, s), 6.17 (1H, d, J 5.8 Hz), 5.11 (2H, s), 3.86 (3H, s), 3.82 (3H, s) and 3.78 (3H, s). MS m/z 369 (M+H)⁺. The 3-benzyloxy-4,5-dimethoxyaniline was prepared by heating a solution of 1-benzyloxy-2,3-dimethoxy-5-nitrobenzene (1.80 g, 6.23 mmol) in ethanol (15 ml) with saturated aqueous sodium hydrosulphite (20 ml) at reflux for 2 h. An additional quantity of sodium hydrosulphite (20 ml) was added and reflux continued for a further 4 h. The reaction mixture was reduced to a small volume then diluted with water and extracted three times with ethyl acetate. The organic phase was dried (MgSO₄) and evaporated to give the crude product which was recrystallised from etherhexane to give the desired product (356 mg) as a white crystalline solid m.p. 118–120°. MS m/z 260 (M+H)⁺. The 1-benzyloxy-2,3-dimethoxy-5-nitrobenzene used as starting material was prepared by treating a solution of 1-benzoyl-2,3-dimethoxybenzene (7.25 g, 29.66 mmol) in glacial acetic acid (15 ml) portionwise with 70% nitric acid (2.84 ml) at room temperature. After 2 h, the reaction mixture was poured into ice-water and extracted with ethyl acetate. The organic phase was washed with 1 M NaOH, then brine, dried (MgSO₄) and evaporated. The crude product was purified by column chromatography [silica 20% ethyl acetate-hexane] to give, after recrystallisation from CH₂Cl₂-hexane, the desired product (1.89 g) as a white solid m.p. 101–102°. MS m/z (relative intensity) (M+H)⁺289 [(M+H),⁺2%] 91 [100%]. 1-Benzyloxy-2,3-dimethoxybenzene was prepared by the method of F Dietl et al Synthesis, 626 (1985).

EXAMPLE 118

N2-(3-Acetamido-4,5-dimethoxyphenyl)-N4-(3-methoxyphenyl)2,4-pyrimidinediamine from 2-chloro-N-(3-methoxyphenyl)-4-pyrimidineamine (0.81 g, 3.43 mmol) [see Example 92] and 3-acetamido-4,5-dimethoxyaniline (0.70 g, 3.43 mmol) to give the title compound (573 mg) as an off-white solid m.p. 195–197°. δH (d⁶ DMSO) 9.26 (1H, s) 9.10 (1H, s), 9.01 (1H, s), 7.97 (1H, d, J 5.7 Hz), 7.74 (1H, s), 7.46–7.25 (3H, m), 7.15 (1H, t, J 8.1 Hz), 6.54 (1H, d, J 8.1 Hz), 6.18 (1H, d, J 5.7 Hz), 3.67 (9H, m) and 2.06 (3H, s). MS m/z 410 (M+H)⁺. The 3-acetamido-4,5-dimethoxyaniline was prepared in an analogous manner to the compound of Example 38, from 1-acetamido-2,3-dimethoxy-5-nitrobenzene (1.65 g, 6.88 mmol) to afford the desired product (1.37 g) as a brown solid m.p. 158–160°. MS m/z 211 (M+H)⁺. The 1-acetamido-2,3-dimethoxy-5-nitrobenzene was prepared in an analogous manner to the nitrobenzene of Example 117 from 1-acetamido-2,3-dimethoxybenzene (1.91 g, 9.8 mmol) to give the desired product (1.70 g) as a white solid m.p. 83°. MS m/z 241 (M+H). The 1-acetamido-2,3-dimethoxybenzene was prepared by treating a solution of 2,3-dimethoxyaniline (1.70 g, 11.1 mmol) in carbon tetrachloride (25 ml) with methanol (0.2 ml) followed by acetic anhydride (3.67 g, 36.0 mmol) and heating the resulting mixture at reflux for 1 h. The cooled reaction mixture was diluted with CH₂Cl₂, washed with water, dried (MgSO₄) and evaporated to give the desired product (2.1 1 g) as a beige solid m.p. 164–165°. MS m/z 196 (M+H)⁺.

EXAMPLE 119

5-Bromo-N2N4-Bis(trimethoxyphenyl)-2,4-pyrimidinediamine from 5-bromo-2-chloro-N-(3,4,5-trimethoxyphenyl)-4-pyrimidineamine (936 mg, 2.5 mmol) and 3,4,5-trimethoxyaniline (459 mg, 2.5 mmol) to give the title compound (160 mg) as a white solid m.p. 186–191°. δH (CDCl₃) 8.16 (1H, s), 7.45 (1H, br s), 6.98 (1H, br s), 6.77 (2H, s), 6.74 (2H, s), 3.83 (3H, s), 3.80 (3H, s), 3.71 (6H, s), 3.66 (6H, s), MS m/z 523 [(M+H)⁺, ⁸¹Br,100%] 521 [(M+H)⁺, ⁷⁹Br, 100%]. The pyrimidineamine starting material was prepared from 5-bromo-2,4-dichloropyrimidine (1.14 g, 5.0 mmol), 3,4,5-trimethoxyaniline (916 mg, 5.0 mmol) and triethylamine (0.77 ml, 5.5 mmol) following the method used for the pyrimidineamine starting material in Example 89. This gave the desired compound as a white solid (1.71 g) m.p. 185–186°. MS m/z 378 [(M+H)⁺, 22%], 376 [(M+H)⁺, 100%], 374 [(M+H)⁺, 78%].

EXAMPLE 120

N4-(4-Hydroxyphenyl)-N2-(3,4,5-trimethoxyphenyl)-2,4-pyrimidinediamine

In a manner analogous to the preparation of the compound of Example 49 from the compound of Example 104 (3.0 g, 6.55 mmol), ammonium formate (1.20 g, 19.60 mmol) and 10% palladium on carbon (300 mg) to give the title compound (2.40 g) as a white solid m.p. 112–115°. δH (CDCl₃) 7/96)1 H. d, J 5.9 Hz), 7.16 (2H, d, J 8.7 Hz), 7.06 (1H, s), 6.83 (1H, s), 6.80 (3H, m), 6.68 (1H, s), 6.01 (1H, d, J 5.9 Hz), 3.79 (3H, s) and 3.78 (6H, s). MS m/z 369 (M+H)⁺.

EXAMPLE 121

N4-(4-(3-Aminopropoxy)phenyl)-N2-(3,4,5-trimethoxyphenyl)-2,4-pyrimidinediamine dihydrochloride In a manner analogous to the preparation of the compound of Example 48 from N4-(4-(3-phthalimidopropoxy)phenyl)-N2-(3,4,5-trimethoxyphenyl)-2,4-pyrimidinediamine (400 mg, 0.72 mmol) and hydrazine monohydrate (0.1 ml, 2.16 mmol) to give the title compound (108 mg) as a buff solid m.p. 258°. δH (d⁶ DMSO) 11.04 (1H, s), 10.54 (1H, s), 8.08 (3H, s), 7.91 (1H, d, J 7.3 Hz), 7.55 (2H, m), 6.86 (2H, d, J 8.7 Hz), 6.78 (2H, s), 6.49 (1H, s), 4.03 (2H, m), 3.65 (9H, s), 2.94 (2H, m) and 2.02 (2H, m). MS m/z 426 (M+H)⁺.

The pyrimidinediemine starting material was prepared according to the method of Example 45 from the compound of Example 120 and 3-bromopropylphthalimide

EXAMPLE 122

N4-(4-(Carboxymethyl)phenyl)-N2-(3,4,5-trimethoxyphenyl)-2,4-pyrimidinediamine

The compound of Example 103 (250 mg, 0.57 mmol) in a solution of ethanol (10 ml) containing 6N aqueous NaOH (2.0 ml) was heated a reflux for 2 h. On cooling the ethanol was removed under reduced pressure and the basic solution brought to pH 5 with 2M hydrochloric acid. The resulting solution was concentrated under reduced pressure, and the residue taken up in hot ethanol (20 ml). This solution was filtered and the filtrate evaporated under reduced pressure to give a residue which was crystalised from ethanol to give the title compound (89 mg) as a white solid m.p. 144–150°. MS m/z 411 (M+H)⁺.

EXAMPLE 123

N4-(4-(tert-Butoxycarbonylmethoxy)phenyl)-N2-(3,4,5-trimethoxyphenyl)-2,4-pyrimidinediamine In a manner analogous to the preparation of the compound of Example 50, from the compound of Example 120 (500 mg, 1.40 mmol), tert-butyl bromoacetate (0.2 ml, 1.40 mmol) and NaH (60% dispersion in oil) (60 ml, 1.50 mmol) to give the title compound (380 mg) as a green solid m.p.139°. MS m/z 483 (M+H)⁺.

EXAMPLE 124

N4-(4-(2-Hydroxyethyl)phenyl)-N2-(3,4,5-trimethoxyphenyl)-2,4-pyrimidinediamine

In a manner analogous to the preparation of the compound of Example 62 (267 mg, 0.5 mmol) from the compound of Example 106 and LiAlH₄ (40 mg, 1.1 mmol) to give the title compound (108 mg) as a light pink solid m.p. 172°. MS m/z 397 (M+H)⁺.

EXAMPLE 125

N4-(4-(Carboxymethoxy)phenyl)-N2-(3,4,5-trimethoxyphenyl)-2,4-pyrimidinediamine

A solution of the compound of Example 123 (300 mg, 0.62 mmol) in CH₂Cl₂ (20 ml) was treated with trifluoroacetic acid (3.0 ml) and stirred at room temperature for 5 h. After this time the reaction was concentrated under reduced pressure to give a brown oil, which was subjected to column chromatography [silica CH₂Cl₂/methanol/acetic acid/water 86.5:10:2:1.5] to give the title compound (123 mg) as a white solid m.p. 159° after recrystallisation from methanol. MS m/z 427 (M+H)⁺.

EXAMPLE 126

4-Phenoxy-N2-(3,4,5-trimethoxyphenyl)-2-pyrimidineamine

2-Methylsulphonyl-4-phenoxypyrimidine (0.76 g, 3.04 mmol) and 3,4,5-trimethoxyaniline (0.56 g, 4.0 mmol) were heated as a melt at 1400 for 2 h. On cooling the residue was partitioned between ethyl acetate (50 ml) and 2M hydrochloric acid (50 ml), and the organic layer was washed with water (50 ml), dried (MgSO₄) and concentrated under reduced pressure. The residue was subjected to column chromatography [silica 20% ethyl acetate-hexane] to give the title compound (18 mg) as a white solid m.p. 149° after recrystallisation from ethyl acetate. δH (CDCl₃) 8.26 (1H, d, J 5.6 Hz), 7.39 (2H, m), 7.26 (1H,m), 7.18–7.15 (2H, m), 6.73 (2H, s), 6.31 (1H, d, J 5.6 Hz), 3.77 (3H, s) and 3.64 (6H, s). MS m/z 354 (M+H)⁺. The pyrimidine used as starting material was prepared by the addition of 50% 3-chloroperoxybenzoic acid (15.19 g, 88.0 mmol) to a solution of 4-phenoxy-2-thiomethylpyrimidine (5.0 g, 22.9 mmol) in CH₂Cl₂ (100 ml) at 0°. The resulting mixture was allowed to rise to room temperature over 12 h, and was then washed with 2M aqueous NaOH (2×100 ml), saturated aqueous sodium sulphite (2×100 ml), dried (MgSO₄) and concentrated under reduced pressure. The residue was subjected to column chromatography to give the desired product (0.81 g) as a colourless oil. δH (CDCl₃) 8.49 (1H, d, J 5.5 Hz), 7.45 (2H, t, J 8.0 Hz), 7.33–7.26 (1H, m), 7.19–7.16 (2H, m), 6.85 (1H, d, J 5.5Hz) and 3.23 (3H, s). The 4-phenoxy-2-thiomethylpyrimidine used as starting material was prepared by heating a solution of 4-fluoro-2-thiomethylpyridine [N. Pléet al., J. Het. Chem. 31, 1311–1315 (1994)] (9.98 g, 69.3 mmol) and phenol (6.58 g, 70.0 mmol) in dry DMF (100 ml) in the presence of caesium carbonate (22.8 g, 70.0 mmol) at 400 for 6 h. The reaction was concentrated in vacuo and the residue was partitioned between ethyl acetate (100 ml) and water (100 ml). The organic layer was dried (MgSO₄), concentrated under reduced pressure and the residue subjected to column chromatography [silica 40% ethyl acetate-hexane] to give the desired product (7.01 g) as a colourless oil. δH (CDCl₃) 8.33 (1H, dd, J 4.7, 0.9 Hz), 7.40 (2H, dd, 8.0,1.1 Hz), 7.26 (1H, m), 7.23 (2H, m), 6.46 (1H, dd, J 4.7, 0.9Hz) and 2.37 (3H, s). MS m/z 219 (M+H)⁺.

EXAMPLE 127

N,N'-Bis(3,4,5-Trimethoxyphenyl)-2,4-pyrimidinediamine

A solution of 2,4-dichloropyrimidine (1.0 g, 6.7 mmol), 3,4,5-trimethoxyaniline (2.5 g, 13.4 mmol) and triethylamnine (1.8 ml, 12.6 mmol) was heated at reflux for 5 h. On cooling the resulting precipitate was collected and recrystallised from ethyl acetate to give the title compound (450 mg) as a purple solid m.p. 180°. MS m/z 443 (M+H)⁺.

EXAMPLE 128

4-Benzoyl-N-(3,4,5-trimethoxyphenyl)-2-pyrimidineamine

To a solution of N-methoxy-N-methyl-2-(3,4,5-trimethoxyphenylamino)-pyrimidine-4-carboxamide (0.82 g, 2.30 mmol) in THF (40 ml) cooled to −78° under a nitrogen atmosphere was added phenylmagnesium bromide [Aldrich 1M/THF] (6.90 ml, 6.90 mmol) dropwise. On completion of addition the reaction was left to warm to room temperature over 3 h and aqueous NH₄Cl solution (10 ml) was then added and the mixture concentrated under reduced pressure. The residue was partitioned between water (20 ml) and ethyl acetate (40 ml), the organic layer dried (MgSO₄) and evaporated. The residue was subjected to column chromatography [silica 50% hexane-ethyl acetate] and after recrystallisation from ethyl acetate-hexane the title compound (123 mg) was obtained as a yellow solid m.p 135°. δH (CDCl$_3$) 8.65 (1H, d, J 4.8 Hz), 8.05 (2H, dd, J 5.1, 2.0 Hz), 7.61 (1H, dd, J 5.3, 2.0 Hz), 7.46 (2H, m), 7.24 (1H, d, J 4.8 Hz), 3.79 (3H, m) and 3.63 (6H, m). MS m/z 366 (M+H)$^+$. The pyrimidine-4-carboxamide used as starting material was prepared by treating a solution of 4-carboxy-N-(3,4,5-trimethoxyphenyl)-2-pyrimidineamine hydrochloride (2.0 g, 5.86 mmol) and triethylamine (2.0 ml, 14.0 mmol) in CH$_2$Cl$_2$ (40 ml), cooled to −20° under a nitrogen atmosphere, with isobutylchloroformate (1.1 ml, 7.0 mmol). The resulting mixture was stirred for 20 min. before N,O-dimethylhydroxylamine hydrochloride (683 mg, 7.0 mmol) and triethylamine (1.0 ml, 7.0 mmol) were added and the reaction allowed to warm to room temperature over 3 h. After washing with 2M hydrochloric acid (1×50 ml) and 2M NaOH solution (1×5 ml), the reaction was dried (MgSO$_4$) and concentrated under reduced pressure. The residue was subjected to column chromatography [silica ethyl acetate] to give the desired product (1.02 g), as a yellow oil. δH (CDCl$_3$) 8.51 (1H, d, J 4.9 Hz), 7.21 (1H, br s), 6.92 (3H, br s), 3.86 (6H, s), 3.82 (3H, s), 3.69 (3H, br s) and 3.36 (3H, s). MS m/z 349 (M+H)$^+$. The 4-carboxy-N-(3,4,5-trimethoxyphenyl)-2-pyrimidineamine hydrochloride was prepared by heating a solution of 4-cyano-N-(3,4,5-trimethoxyphenyl)-N-pyrimidineamine (2.88 g, 10.49 mmol) in aqueous 2N NaOH (60 ml) and ethanol (10 ml) at reflux for 3 h. On cooling the reaction mixtrure was adjusted to pH 3 with 2M hydrochloric acid, and the resulting precipitate collected and dried to give the desired product (2.7 g) as an orange solid m.p. 241°. MS m/z 306 (M+H)$^+$. The 4-cyano-N-(3,4,5-trimethoxyphenyl)-2-pyrimidineamine was prepared by heating a solution of 2-chloro-4-cyanopyrimidine [G. Davies et al. J. Het. Chem. 1, 130–133, (1963)] (11.0 g, 78.8 mmol), 3,4,5-trimethoxy aniline (14.4 g, 79.4 mmol) and triethylamine (12.0 ml) in ethanol at reflux for 4 h. On cooling the resulting precipitate was collected and dried to give the desired product (13.70 g) as a yellow solid m.p. 165°. MS m/z 287 (M+H)$^+$.

EXAMPLE 129

N-Phenyl-2-(3,4,5-trimethoxyphenylamino) pyrimidine-4-carboxamide

In a manner analogous to the preparation of the pyrimidine-4-carbox amide intermediate of Example 128, from 4-carboxy-N-(3,4,5-trimethoxyphenyl)-2-pyrimidineamine hydrochloride (1.0 g, 2.92 mmol), isobutylchloroformate (0.4 ml, 3.07 mmol), aniline (0.28 ml, 3.07 mmol) and triethylamine (1.22 ml, 8.76 mmol) to give the title compound (655 mg) as a yellow solid m.p. 158–1590. 8H (CDCl$_3$) 9.66 (1H, br s), 8.67 (1H, d, J 4.9 Hz), 7.71–7.67 (2H, m), 7.58 (1H, d, J 4.9 Hz), 7.40–7.34 (3H, m), 7.19–7.14 (1H, m), 6.88 (2H, s), 3.87 (6H, s) and 3.86 (3H, s). MS m/z 381 (M+H)$^+$.

EXAMPLE 130

4-Phenylsulphonamido-N2-(3,4,5-trimethogyphenyl)-2-pyrimidineamine

A solution of 2-chloro-4-phenylsulphamidopyrimidine (250 mg, 0.93 mmol) and 3,4,5-trimethoxyaniline (187 mg, 1.02 mmol) in ethoxyethanol (5 ml) was heated at 140° for 12 h. After this time the solvent was evaporated under reduced pressure and the residue partitioned between ethyl acetate (10 ml) and water (10 ml). The organic layer was washed with water (2×25 ml), dried (MgSO$_4$) and evaporated and the resulting solid subjected to column chromatography [silica-ethyl acetate] to give the title compound (187 mg) as a buff solid, m. p. 222–223°. δH (CDCl$_3$) 8.11 (1H, d, J 5.9 Hz), 7.92 (3H, m), 7.57 (1H, m), 7.50 (3H, m), 6.80 (2H, s), 6.66 (1H, d, J 5.9 Hz), 3.81 (6H, s) and 3.21 (3H, s). MS m/z 417 (M+H)$^+$. The 2-chloro-4-phenylsulonamidopyrimidine was prepared by heating 2,4-dichloropyrimidine (1.42 g, 9.5 mmol), benzenesulphonamide (4.5 g, 29.0 mmol) and potassium, carbonate (3.3 g, 24.0 mmol) in DMA (25 ml) for 0.75 h). The reaction was cooled to 5°, water (20 ml) added, and adjusted to pH 2.5 with 2M HCl. The resulting precipitate was collected to give the desired product (1.8 g) as a light yellow solid m.p. 164°. MS m/z 270 (M+H)$^+$. cl EXAMPLE 131

N4-(tert-Butoxycarbonyl)-N2-(3,4,5-trimethoxyphenyl)-2,4-pyrimidinediamine

To a solution of diphenylphosphorylazide (0.92 ml, 4.3 mmol) in tertbutyl alcohol (10 ml), was added triethylamine (1,2 ml, 8.5 mmol) and 4-carboxy-N-(3,4,5-trimethoxyphenyl)-2-pyrimidineamine (1.0 g, 2.9 mmol), [see Example 121] and the mixture heated at reflux for 2 h. After this time the solvent was evaporated and the residue partitioned between ethyl acetate (100 ml) and water (100 ml). The organic layer was washed with water (100 ml), dried (MgSO$_4$) and concentrated under reduced pressure. Column chromatography [silica 2% methanol CH$_2$Cl$_2$] gave the title compound (850 mg) as a light yellow solid m.p. 124°. δH (CDCl$_3$) 8.27 (1H, d, J 5.8 Hz), 7.45 (1H, br s), 7.32 (1H, d, J 5.8 Hz), 7.20 (1H, br s), 6.81 (2H, s), 3.85 (6H, s), 3.81 (3H, s) and 1.53 (9H, s). MS m/z 377 (M+H)$^+$.

EXAMPLE 132

4-Phenylcarboxamido-N-(3,4,5-trimethoxyphenyl)-2-pyrimidineamine

In a manner analogous to the preparation of the pyrimidine-4-caboxamide intermediate of Example 128, from benzoic acid (66 mg, 0.54 mmol), isobutylchloroformate (0.078 ml, 0.6 mmol) N2-(3,4,5-trimethoxyphenyl)-2,4-pyrimidinediamine (150 mg, 0.54 mmol) to give the title compound (30 mg) as a white solid m.p. 88–89°. δH (CDCl$_3$) 8.39 (1H, d, J 5.6 Hz), 8.32 (1H, br s), 7.89–7.85 (2H, m), 7.74 (1H, d, J 5.6 Hz), 7.64–6.50 (3H, m) 6.99 (1H, br s), 6.85 (2H, s), 3.88 (6H, s) and 3.84 (3H, s), MS m/z 381 (M+H)$^+$. The N2-(3,4,5-trimethoxyphenyl)-2,4-pyrimidinediamine used as starting material was prepared by treating a solution of the compound of Example 131 (600 mg, 1.6 mmol) in methanol (10 ml) with 2M hydrochloric acid (10 ml), which was then heated at reflux for 2 h. On cooling the methanol was evaporated and the aqueous solution adjusted to pH 12 with 2N aqueous NaOH. The basic solution was extracted with CH$_2$Cl$_2$ (3×30 ml), then the combined organic extracts were washed with saturated brine (1×20 ml), dried (MgSO$_4$) and concentrated under reduced pressure to give the desired product (340 mg) as a light yelllow solid m.p. 89°. MS m/z 277 (M+H)$^+$.

EXAMPLE 133

N2-(3,4-Dimethoxy-5-hydroxy)-N4-(3-methoxyphenyl)-2,4-pyrimidinediamine

In a manner analogous to the preparation of the compound of Example 49, from the compound of Example 117 (200 mg, 0.44 mmol) to give the title compound (109 mg) as a white solid m.p. 94–97°. δH (d$^6$ DMSO) 9.24 (1H, s), 8.86 (1H, s), 8.84 (1H, s), 7.97 (1 H. d, J 6.0 Hz), 7.32 (1H, d, J 9.2 Hz), 7.26 (1H, s), 7.17 (1H, t, J 8.1 Hz), 6.89 (2H, m), 6.54 (1H, d, J 8.3 Hz), 6.17 (1H, d, J 5.7 Hz), 5.73 (3H, s), 5.69 (3H, s) and 3.63 (3H, s).

The compound of Examples 134–137 were prepared in a similar manner to the compound of Example 1 from the starting materials shown:

EXAMPLE 134

5-Methoxy-4-phenyl-N-(3,4,5-trimethoxyphenyl)-2-pyrimidineamine from 3,4,5-trimethoxyphenylguanidine nitrate (1.43 g, 5.0 mmol), 3-dimethylamino-2-methoxy-1-phenyl-2-propen-1-one (1.03 g, 5.0 mmol) and NaOH (220 mg) to give the title compound (200 mg) as straw coloured crystals m.p. 168–170°. $\delta$H (d$^6$ DMSO) 9.36 (1H, br s), 8.47 (1H, s), 8.09 (2H, m), 7.48 (3H, s), 7.26 (2H, s), 3.88 (3H, s), 3.75 (6H, s) and 3.59 (3H, s). MS m/z 368 (M+H)$^+$. The 3-dimethylamino-2-methoxy-1-phenyl-2-propen-1-one was prepared in a similar manner to the analogous starting material of Example 61, from 2-methoxyacetophenone (4.51 g, 30.0 mmol) to give the desired product (5.30 g) as an orange oil. MS m/z 206 (M+H)$^+$.

EXAMPLE 135

4-Phenyl-5-thiomethyl-N-(3,4,5-trimethoxyphenyl)-2-pyrimidineamine from 3,4,5-trimethoxyphenylguanidine nitrate (1.43 g, 5.0 mmol), 3-dimethylamino-1-phenyl-2-thiomethyl-2-propen-1-one (1.11 g, 5.0 mmol) and NaOH (220 mg, 5.5 mmol) to give the title compound (79.8 mg) as light yellow crystals m.p. 143°. $\delta$H (CDCl$_3$) 8.52 (1H, s), 7.88–7.85 (2H, m), 7.49 (3H, m), 7.16 (1H, br s), 7.02 (2H, s), 3.86 (6H, s), 3.82 (3H, s) and 2.26 (3H, s). MS m/z 384 (M+H)$^+$. The 3-dimethylamino-1-phenyl-2-thiomethyl-2-propen-1-one was prepared in a similar manner to the analogous starting material of Example 61, from 2-thiomethylacetophenone (4.28 g, 25.7 mmol) to give the desired product (3.41 g) as an orange oil. 5H (CDCl$_3$) 7.49–7.47 (2H, m), 7.46 (1H, s), 7.41–7.34 (3H, s), 3.27 (6H, s) and 2.12 (3H, s) MS m/z 222 (M+H)$^+$.

EXAMPLE 136

5-Nitro-4-phenyl-N-(3,4,5-trimethoxyphenyl)-2-pyrimidineamine from 3,4,5-trimethoxyphenylguanidine nitrate (1.14 g, 4.0 mmol), 3-dimethylamino-2-nitro-1-phenyl-2-propen-1-one (0.88 g, 4.0 mmol) and NaOH (176 mg, 4.4 mmol) to give the title compound (1.33 g) as an orange powder m.p. 188–189°. $\delta$H (d$^6$ DMSO) 10.60 (1H, br s), 9.16 (1H, s), 7.61 (2H, m), 7.56–7.46 (3H, m), 7.25 (2H, br s), 3.74 (6H, s) and 3.63 (3H, s), MS m/z 383 (M+H)$^+$. The 3-dimethylamino-2-nitro-1-phenyl-2-propen-1-one was prepared in a similar manner to the analogous starting material of Example 61 from benzoylnitromethane (4.12 g, 25.0 mmol) to give the desired product (1.27 g) as yellow crystals m.p. 103–105°. MS m/z 243 [(M+Na)$^+$, 70%] 221 [(M+H)$^+$, 100%].

EXAMPLE 137

5-Ethoxycarbonyl-4-phenyl-N-(3,4,5-trimethoxyphenyl)-2-pyrimidineamine from 3,4,5-trimethoxyphenylguanidine nitrate (2.86 g, 10.0 mmol), 3-dimethylamino-2-ethoxycarbonyl-1-phenyl-2-propen-1-one (2.47 g, 1 0.0 mmol) and NaOH (440 mg, 11 .0 mmol) to give the title compound (3.10 g) as straw coloured crystals m.p. 160–161°. $\delta$H (d$^6$ DMSO) 10.12 (1H, br s), 8.87 (1H, s), 7.59 (2H, m), 7.50–7.45 (3H, m), 7.28 (2H, s), 4.11 (2H, q. 1 7.1 Hz), 3.74 (6H, s), 3.61 (3H, s) and 1.06 (3H, t, J 7.1 Hz). The 3-dimethylamino-2-ethoxycarbonyl-1-phenyl-2-propen-1-one was prepared in a similar manner to the analogous starting material of Example 61, from ethylbenzoylacetate (5.77 g, 30.0 mmol) to give the desired product (6.01 g) as a yellow solid m.p. 64–65°. MS m/z 248 (M+H)$^+$.

EXAMPLE 138

5-Amino-4-phenyl-N-(3,4,5-trimethoxyphenyl)-2-pyrimidineamine

In a manner analogous to the preparation of the compound of Example 38, from the compound of Example 136 (500 mg, 1.32 mmol) to give the title compound (260 mg) as a yellow solid m.p. 149–150°. $\delta$H (CDCl$_3$) 8.09 (1H, s), 7.87–7.84 (2H, m), 7.51–7.47 (3H, m), 7.00 (2H, s), 6.87 (1H, br s 3.86 (6H, s), 3.81 (3H, s) and 3.52 (2H, br s). MS m/z 353 (M+H)$^+$.

EXAMPLE 139

4-Phenylsulphonyl-N-(3,4,5-trimethoxyphenyl)-2-pyrimidineamine

In a manner analogous to the preparation of the compound of Example 89, from 2-chloro-4-phenyl-sulphanylpyrimidine (1.41 g, 6.35 mmol) and 3,4,5-trimethoxyphenylaniline (1.16 g, 6.35 mmol) to give the title compound (1.43 g) as an off-white solid m.p. 110°. $\delta$H (CDCl$_3$) 8.04 (1H, d, J 5.4 Hz), 7.59 (2H,m), 7.47 (3H, m), 7.22 (1H, br s), 6.88 (2H, s), 6.18 (1H, d, J 5.4 Hz), 3.83 (6H, s) and 3.81 (3H, s). MS m/z 370 (M+H)$^+$. The 2-chloro-4-phenylsulphanylpyrimidine was prepared by treating a solution of thiophenol (4.7 ml, 45.4 mmol) in THF (30 ml) at 0°, with a 1.0M solution of sodium bis(trimethylsilyl)amide in THF (45.4 ml) and the mixture stirred for 0.5 h. After a thick white precipitate had formed, 2,4-dichloropyrimidine (6.83 g, 45.4 mmol) and DMA (70 ml) were added and the mixture heated at 1200 for 2 h. The reaction was then concentrated under reduced pressure and the residue partitioned between water and ethyl acetate. The aqueous layer was further extracted with ethyl acetate and the combined organic layers were dried (MgSO$_4$) and evaporated. The residue was subjected to column chromatography (silica 20% ethyl acetate-hexane) to give the desired product (2.66 g) as a white solid. $\delta$H 8.17 (1H, d, J 5.5 Hz), 7.59 (2H, m), 7.53 (3H, m) and 6.62 (1H, d, J 5.5 Hz). MS m/z 223 (M+H)$^+$.

EXAMPLE 140

N-(4-(2-(3,4,5-Trimethoxyphenylamino)pyrimidin-4-yl)-2-aminoacetamide

A solution of N-(4-(2-(3,4,5-trimethoxyphenylamino) pyrimidin-4-yl)phenyl)-2-N-(9-fluorenylmethoxycarbonyl) aminoacetamide (210 mg, 0.33 mmol) and piperidine (0.5 ml, 5 mmol) in DMF (2.5 ml) was stirred at room temperature for 0.5 h. The sovlent was evaporated and the residue triturated with hot ethyl acetate to give the title compound (25 mg) as an off-white solid m.p. 213°. $\delta$H (d$^6$ DMSO) 9.47 (1H, s), 8.49 (1H, d, J 5.4 Hz), 8.11 (2H, d, J 8.3Hz), 7.75 (2H, d, J 8.2Hz), 7.29 (3H,m), 3.80 (6H, s) and 3.61 (3H, s). MS m/z 410 (M+H)$^+$. The starting material for the above process was obtained by treating a solution of the compound of Example 39 (250 mg, 0.71 mmol) in $CH_2Cl_2$ (10 ml) with N-FMOCglycyl chloride (337 mg, 1.07 mmol) and 5% aqueous $Na_2CO_3$ solution (8 ml). After the mixture had been stirred for 1 h at room temperature, the aqueous phase was discarded and the organic layer dried ($MgSO_4$) and evaporated. The residue was subjected to column chromatography [silica 10% methanol-$CH_2Cl_2$] to give the desired product (235 mg) as an off-white solid. m.p. 102° (decomp.). $\delta H$ ($d^6$ DMSO) 10.23 (1H, s), 9.48 (1H, s), 8.48 (1H, d, J 5.1 Hz), 8.15 (2H, d, J 8.3 Hz), 7.88 (2H, d, J 7.3 Hz), 7.73 (4H, m), 7.64 (1H, m), 7.43–7.30 (7H, m), 4.34–4.20 (3H, m), 3.79 (8H, m) and 3.62 (3H, s).

EXAMPLE 141

6-Methyl-4-phenoxy-N-(3,4,5-trimethoxyphenyl) pyrimidine-2-amine

4-Chloro-6-methyl-N-(3,4,5-trimethoxyphenyl) pyrimidine-2-amine (0.30 g, 0.97 mmol) was added to a solution of sodium phenoxide (0.97 mmol) [prepared from phenol (0.091 g, 0.97 mmol) and NaH (60% in mineral oil; 0.039 g, 0.97 mmol)], and heated to 80° for 17 h with stirring. Water was added and the mixture was extracted with $CH_2CH_2$ (2×30 ml), the organic phases were dried ($MgSO_4$) and evaporated to a yellow oil. The residue was subjected to chromatography (silica, 2% methanol/$CH_2CH_2$) to give the title compound (0.046 g). A portion was recrystallised from methanol to give an off white crystalline solid m.p. 175°. $\delta_H$ ($CDCl_3$) 2.38 (3H, s), 3.64 (6H, s), 3.77 (3H, s), 6.19 (1H, s), 6.78 (2H, s), 6.95 (1H, s), 7.15 (2H, d, J 7.5 Hz), 7.23 (1H, m) and 7.39 (2H, t, J 7.5 Hz).

The amine starting material for this reaction was prepared from the following:

4-Chloro-6-methyl-N-(3,4,5-trimethoxyphenyl) pyrimidine-2-amine (b)

6-Methyl-2-(3,4,5-trimethoxyphenylamino)-4(3H) pyrimidinone (1.0 g, 3.63 mmol) was dissolved in phosphoryl chloride and heated to 100° for 2 h. The mixture was cooled to room temperature and evaporated in vacuo to a viscous oil. The oil was dissolved in $CH_2CH_2$ (50 ml) and washed twice with saturated aqueous $NaHCO_3$, the organic phases dried ($MgSO_4$) and concentrated in vacuo. The residue was subjected to column chromatography (silica, 2% methanol/$CH_2CH_2$) to afford the title compound as an off white solid (1.03 g). A small amount was recrystallised from ethyl acetate to give fine off-white needles. m.p. 195–196°. $\delta_H$ ($CDCl_3$) 2.40 (3H, s), 3.82 (3H, s), 3.88 (6H, s), 6.64 (1H, s), 6.95 (2H, s), and 7.07 (1H, br s).

The pyrimidinone starting material for this reaction was prepared as follows:

6-Methyl-2-(3,4,5-trimethoxyphenylamino)-4-(3H) pyrimidinone

To a solution of sodium methoxide (0.96 g, 1.79 mmol) in methanol was added ethyl-3-oxo-butanoate (0.23 g, 1.79 mmol) and 3,4,5-trimethoxyphenylguanidinium nitrate (0.5 g, 1.79 mmol). The mixture was stirred at reflux for 17 h. The reaction mixture was cooled to room temperature and evaporated in vacuo to give a dark grey solid. Recrystallisation from ethanol gave the title compound (0.25 g, 49%) as a light grey solid, m.p. 228–230° (dec). $\delta_H$ ($d^6$DMSO) 2.12 (3H, s), 3.61 (3H, s), 3.74 (6H, s), 5.69 (1H, s), 7.02 (2H, s), 8.70 (1H, br s) and 10.47 (1H, br s).

BIOLOGICAL ACTIVITY

The following assays were used to demonstrate the activity and selectivity of compounds according to the invention:

$p56^{lck}$ kinase assay

The tyrosine kinase activity of $p56^{lck}$ was determined using a RR-src peptide (RRLIEDNEYTARG) and [$\gamma$-$^{33}$P] ATP as substrates. Quantitation of the $^{33}$P-phosphorylated peptide formed by the action of $p56^{lck}$ was achieved using an adaption of the method of Geissler et al (J. Biol. Chem. (1990) 265, 22255–22261).

All assays were performed in 20 mM HEPES pH 7.5 containing 10 mM $MgCl_2$, 10 mM $MnCl_2$, 0.05% Brij, 1 $\mu$M ATP (0.5 $\mu$Ci[$\gamma$-$^{33}$P]ATP) and 0.8 mg/ml RR-src. Inhibitors in dimethylsulphoxide (DMSO) were added such that the final concentration of DMSO did not exceed 1%, and enzyme [human $p56^{lck}$] such that the consumption of ATP was less than 10%. After incubation at 30° C. for 15 min, the reaction was terminated by the addition of one-third volume of stop reagent (0.25 mM EDTA and 33 mM ATP in $dH_2O$). A 15 $\mu$l aliquot was removed, spotted onto a P-30 filtermat (Wallac, Milton Keynes, UK), and washed sequentially with 1% acetic acid and $dH_2O$ to remove ATP. The bound $^{33}$P-RR-src was quantitated by scintillation counting of the filtermat in a Betaplate scintillation counter (Wallac, Milton Keynes, UK) after addition of Meltilex scintillant (Wallac, Milton Keynes, UK). The dpm obtained, being directly proportional to the amount of $^{33}$P-RR-src produced by $p56^{lck}$, were used to determine the $IC_{50}$ for each compound.

$p59^{fyn}$ kinase assay

Compounds of the invention were assayed for $p59^{fyn}$ inhibitory activity in a similar manner to the $p56^{lck}$ assay, using human $p59^{fyn}$.

EGFr kinase assay

The tyrosine kinase activity of the EGF receptor (EGFr) was determined using a similar methodology to the $p56^{lck}$ kinase assay, except that the RR-src peptide was replaced by a peptide substrate for EGFr obtained from Amersham International plc (Little Chalfont, UK) and used at the manufacturers recommended concentration. $IC_{50}$ values for each test inhibitor were determined as described previously in the $p56^{lck}$ assay.

ZAP-70 kinase assay

The tyrosine kinase activity of ZAP-70 was determined using a capture assay based on that employed above for $p56^{lck}$. The RR-src peptide was replaced with polyGlu-Tyr (Sigma; Poole, UK) at a final concentration of 17 $\mu$g/ml. After addition of the stopped reaction to the filtermat, trichloroacetic acid 10% (w/v) was employed as the wash reagent instead of acetic acid and a final wash in absolute ethanol was also performed before scintillation counting. $IC_{50}$ values for each test inhibitor were determined as described above in the $p56^{lck}$ assay.

Csk kinase assay

Compounds of the invention were assayed for csk kinase inhibitory activity in a similar manner to the ZAP-70 assay using human csk kinase.

Protein kinase C assay

Inhibitor activity against protein kinase C (PKC) was determined using PKC obtained from Sigma Chemical Company (Poole, UK) and a commercially available assay system (Amersham International plc, Little Chalfont, UK). Briefly, PKC catalyses the transfer of the $\gamma$-phosphate ($^{32}$p) of ATP to the threonine group on a peptide specific for PKC. Phosphorylated peptide is bound to phosphocellulose paper, subsequently quantified by scintillation counting and $IC_{50}$ values determined as before.

In the above assays, compounds according to the invention, including the compounds of the Examples inhibit the protein kinase $p56^{lck}$, $p59^{fyn}$, ZAP-70 or protein kinase C at concentrations at which they have little or no effect on the remaining kinases, including EGFr kinase and Csk kinase. Thus, for example the compounds of Example 96 and 103 have $IC_{50}$ values in the $p56^{lck}$ assay of 215 nM and 40 nM respectively. The compounds are also active against $p59^{fyn}$ but have $IC_{50}$ values at least 10× greater against the remaining kinases described above. In another example the compounds of Example 64 and 66 have $IC_{50}$ values in the ZAP-70 assay of 124 nM and 68 nM respectively. The compounds are also active in the protein kinase C assay, but have $IC_{50}$ values at least 10× greater against the remaining kinases. In a further example, the compounds of Examples 48 and 81 have $IC_{50}$ values in the protein kinase C assay of 22 nM and 92 nM respectively, but have $IC_{50}$ values at least 10× greater against the remaining kinases.

We claim:
1. A compound of formula (1)

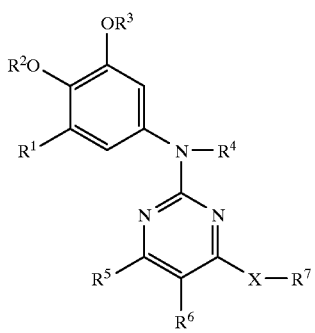

(1)

wherein:
$R^1$ is —$OR^8$;

$R^2$ and $R^3$, which may be the same or different, is each an optionally substituted straight or branched chain $C_{1-6}$alkyl, $C_{2-6}$alkenyl or $C_{2-6}$alkynyl group;

$R^4$ is a hydrogen atom or a straight or branched chain $C_{1-6}$alkyl group;

$R^5$ is a hydrogen atom;

$R^6$ is a hydrogen or halogen atom, amino (—$NH_2$), —$NHR^9$, —$NR^9R^{10}$, nitro, carboxyl (—$CO_2H$), esterified carboxyl or —$X^1R^{6a}$;

X and $X^1$, which may be the same or different, is each a direct bond or a linker atom or group selected from —O—, —S—, —C(O)—, —C(S)—, —S(O)—, —S(O)$_2$—, —N($R^{11}$)—, —CON($R^{11}$)—, —OC(O)N($R^{11}$)—, —CSN($R^{11}$)—, —N($R^{11}$)CO—, —N($R^{11}$)C(O)O—, —N($R^{11}$)CS—, —SON($R^{11}$)—, —SO$_2$N($R^{11}$)—, —N($R^{11}$)SO$_2$—, —N($R^{11}$)CON($R^{11}$)—, —N($R^{11}$)CSN($R^{11}$)—, —N($R^{11}$)SON($R^{11}$)— and —N($R^{11}$)SO$_2$N($R^{11}$)—;

$R^7$ is an optionally substituted $C_{1-10}$aliphatic group optionally containing one to four $X^2$ heteroatoms or heteroatom containing groups, an optionally substituted $C_{3-10}$cycloaliphatic group optionally containing one to four $X^2$ heteroatoms or heteroatom containing groups, an optionally substituted monocyclic or bicyclic $C_{6-12}$aryl group or an optionally substituted monocyclic or bicyclic $C_{5-13}$ heteroaryl group containing one to four heteroatoms selected from oxygen, sulfur or nitrogen atoms, wherein said optional substituents on $R^7$ are from one to about three $R^{12}$ groups;

$X^2$ is —O—, —S—, —C(O)—, —C(S)—, —S(O)—, —S(O)$_2$—, —N($R^{11}$)—, —CON($R^{11}$)—, —OC(O)N($R^{11}$)—, —CSN($R^{11}$)—, —N($R^{11}$)CO—, —N($R^{11}$)C(O)O—, —N($R^{11}$)CS—, —SON($R^{11}$)—, —SO$_2$N($R^{11}$)—, —N($R^{11}$)SO$_2$—, —N($R^{11}$)CON($R^{11}$)—, —N($R^{11}$)CSN($R^{11}$)—, —N($R^{11}$)SON($R^{11}$)— or —N($R^{11}$)SO$_2$N($R^{11}$)—;

$R^{6a}$ and $R^8$, which may be the same or different, is each an optionally substituted straight or branched chain $C_{1-6}$alkyl, $C_{2-6}$alkenyl or $C_{2-6}$alkynyl group;

$R^9$ and $R^{10}$, which may be the same or different, is each $R^8$ or —$COR^8$;

$R^{11}$ is a hydrogen atom or a $C_{1-6}$alkyl group;

$R^{12}$ is $R^{13}$, -Alk($R^{13}$)$_m$, optionally substituted heteroC$_{3-6}$ cycloalkyl or optionally substituted -Alk-heteroC$_{3-6}$ cycloalkyl, wherein said optional substituents on $R^{12}$ are one or two groups selected from $C_{1-6}$alkyl, hydroxyl (—OH), hydroxyC$_{1-6}$alkyl and $C_{6-1}$alkyoxy groups;

$R^{13}$ is a halogen atom, amino (—$NH_2$), —$NHR^{14}$, —$N(R^{14})_2$, nitro, cyano, hydroxyl (—OH), —$OR^{14}$, formyl, carboxyl (—$CO_2H$), —$CO_2Alk^1$, thiol (—SH), $SR^{14}$, —$COR^{14}$, —$CSR^{14}$, —$SO_3H$, —$SO_2R^{14}$, —$SO_2NH_2$, —$SO_2NHR^{14}$, —$SO_2N(R^{14})_2$, —$CONH_2$, —$CSNH_2$, —$CONHR^{14}$, —$CSNHR^{14}$, —$CON(R^{14})_2$, —$CSN(R^{14})_2$, —$NHSO_2H$, —$NHSO_2R^{14}$, —$N(SO_2R^{14})_2$, —$NHSO_2NH_2$, —$NHSO_2NHR^{14}$, —$NHSO_2N(R^{14})_2$, —$NHCOR^{14}$, —$NHCONH_2$, —$NHCONHR^{14}$, —$NHCON(R^{14})_2$, —$NHCSR^{14}$, —$NHCSNH_2$, —$NHCSNHR^{14}$, —$NHCSN(R^{14})_2$, —$NHC(O)OR^{14}$, optionally substituted $C_{5-7}$cycloalkyl, optionally substituted monocyclic or bicyclic $C_{6-12}$aryl or optionally substituted monocyclic or bicyclic $C_{5-13}$ heteroaryl, wherein said cycloalkyl, aryl and heteroaryl substituents are one or two groups selected from $C_{1-6}$alkyl, hydroxyl (—OH), hydroxyC$_{1-6}$alkyl and $C_{1-6}$alkyoxy groups;

$R^{14}$ is -Alk($R^{13}$)$_m$, optionally substituted heteroC$_{3-6}$ cycloalkyl, optionally substituted -Alk-heteroC$_{3-6}$ cycloalkyl, optionally substituted monocyclic or bicyclic $C_{6-12}$aryl or optionally substituted monocyclic or bicyclic $C_{5-13}$heteroaryl;

Alk is a straight or branched chain $C_{1-6}$alkylene, $C_{2-6}$alkenylene or $C_{2-6}$alkynylene group optionally interrupted by one, two or three —O— or —S— atoms or —SO—, —S(O)$_2$— or —N($R^{11}$)— groups;

m is zero or an integer 1, 2 or 3; wherein said optional substituents on $R^1$, $R^2$, $R^3$, and $R^{6a}$ are one to three groups selected from halogen, hydroxyl, $C_{1-6}$alkoxy, thiol, $C_{1-6}$alkylthio, amino, $C_{1-6}$alkylamino and $C_{1-6}$dialkylamino, and said optional substituents on $R^8$ are a phenyl group or one to three groups selected from halogen, hydroxyl, $C_{1-6}$alkoxy, thiol, $C_{1-6}$alkylthio, amino, $C_{1-6}$alkylamino and $C_{1-6}$dialkylamino;

and the salts, solvates, hydrates and N-oxides thereof; with the proviso that when $R^{12}$ is a heterocycloalkyl group, then X is other than a direct bond or X is a direct bond and $R^7$ is other than a pyridyl group.

2. Anilinopyrimidines, processes for their preparation, pharmaceutical compositions containing them, their use in medicine. In a preferred embodiment, the compounds have the general formula (1):

51

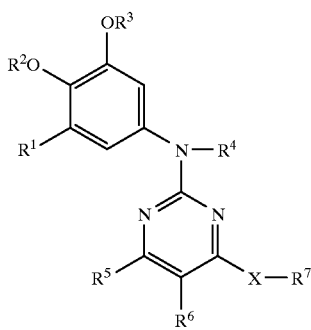

(1)

wherein $R^1$ is preferably methoxy; $R^2$ and $R^3$ are preferably methyl; $R^4$ is preferably a hydrogen atom; $R^5$ is a hydrogen atom or an optionally substituted straight or branched chain alkyl, alkenyl or alkynyl group; $R^6$ is a hydrogen or halogen atom or an amino (—NH$_2$), substituted amino, nitro, carboxyl (—CO$_2$H), esterified carboxyl or —X$^1$R$^{6a}$ where X$^1$ is a direct bond or a linker atom or group and R$^{6a}$ is an optionally substituted straight or branched chain alkyl, alkenyl or alkynyl group; X is a direct bond or a linker atom or group; and R$^7$ is an optionally substituted aliphatic, cycloaliphatic, heteroaliphatic, heterocycloaliphatic, aromatic or heteroaromatic group. Compounds of the invention are selective protein kinase inhibitors, particularly the kinases p56$^{lck}$, p59$^{fyn}$, ZAP-70 and protein kinase C and are of use in the prophylaxis and treatment of immune diseases, hyperproliferative disorders and other diseases in which inappropriate protein kinase action is believed to have a role.

3. A compound according to claim 2 wherein $R^6$ is a hydrogen atom.

4. A compound according to claim 3 wherein $R^1$ is an optionally substituted methoxy group and $R^2$ and $R^3$ is each an optionally substituted methyl or ethyl group.

5. A compound according to claim 4 wherein $R^1$ is a methoxy group and $R^2$ and $R^3$ is each a methyl group.

6. A compound according to claim 1 wherein X is a direct bond, an oxygen or sulphur atom or a —N(R$^{11}$)— group.

7. A compound according to claim 6 wherein X is a direct bond, a sulphur atom or a —NH— group.

8. A compound according to claim 7 wherein $R^7$ is an optionally substituted monocyclic or bicyclic C$_{6-12}$aryl group or an optionally substituted monocyclic or bicyclic C$_{5-13}$ heteroaryl group containing one to four heteroatoms selected from oxygen sulfur or nitrogen atoms.

9. A compound according to claim 8 wherein $R^7$ is an optionally substituted phenyl, 2-pyridyl, 3-pyridyl or 4-pyridyl group.

52

10. A compound of formula 1(a)

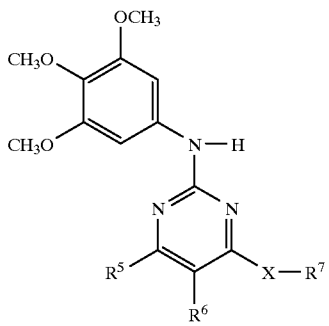

(1a)

wherein:
$R^5$ is a hydrogen atom;
$R^6$ is a hydrogen or halogen atom or an amino (—NH$_2$), —NHR$^9$, —NR$^9$R$^{10}$, nitro, carboxyl (—CO$_2$H), esterified carboxyl or —X$^1$R$^{6a}$ group;
X$^1$ is a direct bond or a linker atom or group selected from —O—, —S—, —C(O)—, —C(S)—, —S(O)—, —S(O)$_2$—, —N(R$^{11}$)—, —CON(R$^{11}$)—, —OC(O)N(R$^{11}$)—, —CSN(R$^{11}$)—, —N(R$^{11}$)CO—, —N(R$^{11}$)C(O)O—, —N(R$^{11}$)CS—, —SON(R$^{11}$)—, —SO$_2$N(R$^{11}$)—, —N(R$^{11}$)SO$_2$—, —N(R$^{11}$)CON(R$^{11}$)—, —N(R$^{11}$)CSN(R$^{11}$)—, —N(R$^{11}$)SON(R$^{11}$)— and —N(R$^{11}$)SO$_2$N(R$^{11}$)—;
X is a direct bond, an oxygen or sulphur atom, or a group —N(R$^{11}$)—; and
$R^7$ is an optionally substituted monocyclic or bicyclic C$_{6-12}$aryl group or an optionally substituted monocyclic or bicyclic C$_{5-13}$ heteroaryl group containing one to four heteroatoms selected from oxygen, sulfur or nitrogen atoms, wherein said optional substituents on R$^7$ are from one to about three R$^{12}$ groups;
$R^9$ and $R^{10}$, which may be the same or different is each R$^a$ or —COR$^a$;
$R^a$ and $R^{6a}$, which may be the same or different, is each an optionally substituted straight or branched chain C$_{1-6}$alkyl, C$_{2-6}$alkenyl or C$_{2-6}$alkanyl group;
$R^{11}$ is a hydrogen atom or a C$_{1-6}$alkyl group;
$R^{12}$ is R$^{13}$,-Alk(R$^{13}$)$_m$, optionally substituted heteroC$_{3-6}$cycloalkyl or optionally substituted -Alk-heteroC$_{3-6}$cycloalkyl, wherein said optional substituents on R$^{12}$ are one or two groups selected from C$_{1-6}$alkyl, hydroxyl (—OH), hydroxyC$_{1-6}$alkyl and C$_{1-6}$alkyoxy groups;
$R^{13}$ is a halogen atom, amino (—NH$_2$), —NHR$^{14}$, —N(R$^{14}$)$_2$, nitro, cyano, hydroxyl (—OH), —OR$^{14}$, formyl carboxyl (—CO$_2$H), —CO$_2$Alk$^1$, thiol (—SH), SR$^{14}$, —COR$^{14}$, —CSR$^{14}$, —SO$_3$H, —SO$_2$R$^{14}$, —SO$_2$NH$_2$, —SO$_2$NHR$^{14}$, —SO$_2$N(R$^{14}$)$_2$, —CONH$_2$, —CSNH$_2$, —CONHR$^{14}$, —CSNHR$^{14}$, —CON(R$^{14}$)$_2$, —CSN(R$^{14}$)$_2$, —NHSO$_2$H, —NHSO$_2$R$^{14}$, —N(SO$_2$R$^{14}$)$_2$, —NHSO$_2$NH$_2$, —NHSO$_2$NHR$^{14}$, —NHSO$_2$N(R$^{14}$)$_2$, —NHCOR$^{14}$, —NHCONH$_2$, —NHCONHR$^{14}$, —NHCON(R$^{14}$)$_2$, —NHCSR$^{14}$, —NHCSNH$_2$, —NHCSNHR$^{14}$, —NHCSN(R$^{14}$)$_2$, —NHC(O)OR$^{14}$, optionally substituted C$_{5-7}$cycloalkyl optionally substituted monocyclic or bicyclic C$_{6-12}$aryl or optionally substituted monocyclic or bicyclic C$_{5-13}$ heteroaryl wherein, said cycloalkyl, aryl and heteroaryl substituents are one or two groups selected from $C_{1-6}$alkyl, hydroxyl (—OH), hydroxy$C_{1-6}$alkyl and $C_{1-6}$alkyoxy groups;

$R^{14}$ is -Alk$(R^{13})_m$, optionally substituted hetero$C_{3-6}$ cycloalkyl, optionally substituted -Alk-hetero$C_{3-6}$ cycloalkyl, optionally substituted monocyclic or bicyclic $C_{6-12}$aryl or optionally substituted monocyclic or bicyclic $C_{5-13}$ heteroaryl;

Alk is a straight or branched chain $C_{1-6}$alkylene, $C_{2-6}$alkenylene or $C_{2-6}$alkynylene group optionally interrupted by one, two or three —O— or —S— atoms or —SO—, —S(O)$_2$- or —N($R^{11}$)— groups;

m is zero or an integer 1, 2 or 3; wherein said optional substituents on $R^5$, $R^a$ and $R^{6a}$ are one to three groups selected from halogen, hydroxyl, $C_{1-6}$alkoxy thiol, $C_{1-6}$alkylthio, amino $C_{1-6}$alkylamino and $C_{1-6}$dialkylamino;

and the salts, solvates, hydrates and N-oxides thereof with the provisos that when $R^{12}$ is a heterocycloalkyl group, then X is other than a direct bond or X is a direct bond and $R^7$ is other than a pyridyl group, and when X is a direct bond and $R^7$ is an optionally substituted $C_{1-10}$aliphatic group optionally containing one to four $X^2$ heteroatoms or heteroatom containing groups or an optionally substituted $C_{3-10}$cycloaliphatic group optionally containing one to four $X^2$ heteroatoms or heteroatom containing groups, then $R^1$ is other than a hydrogen atom.

11. A compound according to claim 10 wherein $R^6$ is a hydrogen atom.

12. A compound according to claim 11 wherein X is a direct bond or a sulphur atom or —NH— group.

13. A compound according to claim 12 wherein $R^7$ is an optionally substituted phenyl, 2-pyridyl, 3-pyridyl or 4-pyridyl group.

14. A compound which is selected from the group consisting of

N,N'-Bis(3,4,5-Trimethoxyphenyl)-2,4-pyrimidinediamine;

4-(2-(2-Dimethylaminoethylamino)pyridin-5-yl)-N-(3,4,5-trimethoxyphenyl)-2-pyrimidineamine;

4-(2-(4-Hydroxybutylamino)pyridin-5-yl)-N-(3,4,5-trimethoxyphenyl)-2-pyrimidineamine;

4-(3-(3-Aminopropoxy)phenyl)-N-(3,4,5-trimethoxyphenyl)-2-pyrimidineamine;

N4-(3,4-Dimethoxyphenyl)-N2-(3,4,5-trimethoxyphenyl)-2,4-pyrimidinediamine;

4-(4-(2-Hydroxyethoxy)phenyl)-N-(3,4,5-trimethoxyphenyl)-2-pyrimidineamine;

4-(2-(3-(Morpholino)propylamino)pyridin-5-yl)-N-(3,4,5-trimethoxyphenyl)-2-pyrimidineamine;

4-(2-(2-(1-Methylpyrrolidin-2-yl)ethylamino)pyridin-5-yl)-N-(3,4,5-trimethoxyphenyl)-2-pyrimidineamine;

N4-(4-(Ethoxycarbonylmethyl)phenyl)-N2-(3,4,5-trimethoxyphenyl)-2,4-pyrimidinediamine;

N4-(4-Hydroxyphenyl)-N2-(3,4,5-trimethoxyphenyl)-2,4-pyrimidinediamine and

N4-(4-(3-Aminopropoxy)phenyl)-N2-(3,4,5-trimethoxyphenyl)-2,4-pyrimidinediamine;

and the salts, solvates, hydrates and N-oxides thereof.

15. A compound according to claim 1 wherein $R^2$, $R^3$ and $R^8$ are $C_{1-6}$alkyl.

16. A compound according to claim 15 wherein $R^2$, $R^3$ and $R^8$ are methyl or ethyl.

17. A compound according to claim 16 wherein $R^2$, $R^3$ and $R^8$ are methyl.

18. A pharmaceutical composition comprising, in combination with one or more pharmaceutically acceptable carriers, excipients or diluents, an effective amount of a compound according to claim 1.

19. A pharmaceutical composition comprising, in combination with one or more pharmaceutically acceptable carriers, excipients or diluents, an effective amount of a compound according to claim 10.

20. A method for the prophylaxis or treatment of a disease or disorder in a mammal in which inappropriate protein tyrosine kinase action plays a role, which comprises administering to a mammal suffering from such a disease or disorder a therapeutically effective amount of a compound according to claim 1.

21. A method according to claim 20 wherein said disease or disorder is selected from the group consisting of autoimmune diseases, transplant rejection, grant versus host disease, hyperproliferative disorders, and diseases in which cells receive pro-inflammatory signals.

22. A method for the prophylaxis or treatment of a disease or disorder in a mammal in which inappropriate protein tyrosine kinase action plays a role, which comprises administering to a mammal suffering from such a disease or disorder a therapeutically effective amount of a compound according to claim 10.

23. A method according to claim 22 wherein said disease or disorder is selected from the group consisting of autoimmune diseases, transplant rejection, grant versus host disease, hyperproliferative disorders, and diseases in which cells receive pro-inflammatory signals.

* * * * *